US010765754B2

(12) United States Patent
Welch et al.

(10) Patent No.: US 10,765,754 B2
(45) Date of Patent: Sep. 8, 2020

(54) COMPOSITIONS AND METHODS RELATED TO INHIBITION OF RESPIRATORY SYNCYTIAL VIRUS ENTRY

(71) Applicants: Navigen, Inc., Salt Lake City, UT (US); University of Utah Research Foundation, Salt Lake City, UT (US)

(72) Inventors: Brett D. Welch, Salt Lake City, UT (US); Michael S. Kay, Salt Lake City, UT (US); Debra Muir Eckert, Salt Lake City, UT (US); Rena McKinnon, Herriman, UT (US); Michael Thomas Jacobsen, Norfolk, NE (US)

(73) Assignees: Navigen, Inc., Salt Lake City, UT (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/753,950

(22) PCT Filed: Aug. 26, 2016

(86) PCT No.: PCT/US2016/049155
§ 371 (c)(1),
(2) Date: Feb. 20, 2018

(87) PCT Pub. No.: WO2017/040350
PCT Pub. Date: Mar. 9, 2017

(65) Prior Publication Data
US 2018/0280520 A1 Oct. 4, 2018

Related U.S. Application Data

(60) Provisional application No. 62/211,624, filed on Aug. 28, 2015.

(51) Int. Cl.
| | | |
|---|---|---|
| *C07K 7/06* | (2006.01) | |
| *C07K 7/08* | (2006.01) | |
| *C07K 14/00* | (2006.01) | |
| *A61K 38/08* | (2019.01) | |
| *A61K 38/10* | (2006.01) | |
| *A61K 38/16* | (2006.01) | |
| *A61K 47/42* | (2017.01) | |
| *A61P 31/14* | (2006.01) | |
| *A61K 38/02* | (2006.01) | |
| *G01N 33/50* | (2006.01) | |

(52) U.S. Cl.
CPC .............. *A61K 47/42* (2013.01); *A61K 38/02* (2013.01); *A61K 38/08* (2013.01); *A61K 38/10* (2013.01); *A61K 38/16* (2013.01); *A61K 38/162* (2013.01); *A61P 31/14* (2018.01); *C07K 7/06* (2013.01); *C07K 7/08* (2013.01); *C07K 14/00* (2013.01); *G01N 33/5008* (2013.01)

(58) Field of Classification Search
CPC ........ A61K 38/02; A61K 38/03; A61K 38/08; A61K 38/10; A61K 38/16; C07K 2/00; C07K 4/00; C07K 7/06; C07K 7/08; C07K 14/00
See application file for complete search history.

(56) References Cited

U.S. PATENT DOCUMENTS

| | | | |
|---|---|---|---|
| 3,610,795 A | 10/1971 | Jacques | |
| 6,586,403 B1 * | 7/2003 | Mathison | C07K 5/06078 514/2.4 |
| 9,381,226 B2 | 7/2016 | Kay et al. | |
| 10,189,878 B2 | 1/2019 | Clinton et al. | |
| 10,406,229 B2 | 9/2019 | Francis et al. | |
| 10,487,121 B2 | 11/2019 | Welch et al. | |
| 10,512,665 B2 | 12/2019 | Kay et al. | |
| 2005/0221294 A1 * | 10/2005 | Eckert | C07K 14/005 435/5 |
| 2014/0323392 A1 | 10/2014 | Francis et al. | |

FOREIGN PATENT DOCUMENTS

| | | | |
|---|---|---|---|
| EP | 0 045 665 A1 | 2/1982 | |
| WO | 2008/098182 A1 | 8/2008 | |
| WO | WO-2008098182 A1 * | 8/2008 | ............. A61K 38/10 |
| WO | 2012/135385 A1 | 10/2012 | |
| WO | WO-2012135385 A1 * | 10/2012 | ............... C07K 7/06 |

OTHER PUBLICATIONS

Welch et al. Potent D-peptide inhibitors of HIV-1 entry. Proceedings of the National Academy of Sciences USA. Oct. 23, 2007, vol. 104, No. 43, pp. 16828-16833. (Year: 2007).*
Lambert et al. Peptides from conserved regions of paramyxovirus fusion (F) proteins are potent inhibitors of viral fusion. Proceedings of the National Academy of Sciences USA. Jan. 1, 1996, vol. 93, pp. 2186-2191. (Year: 1996).*
Beeler et al., "Influenza and respiratory syncytial virus (RSV) vaccines for infants: Safety, immunogenicity, and efficacy," *Microbial Pathogenesis* 55:9-15, 2013.
Broughton et al., "Drugs for the management of respiratory syncytial virus infection," *Curr. Opin. Investig. Drugs* 5(8):862-865, 2004. (Abstract Only).
Hashem et al., "Respiratory syncytial virus in healthy adults: the cost of a cold," *Journal of Clinical Virology* 27:14-21, 2003.
Rizo et al., "Constrained Peptides: Models of Bioactive Peptides and Protein Substructures," *Annu. Rev. Biochem.* 61:387-418, 1992.
The IMpact-RSV Study Group, "Palivizumab, a Humanized Respiratory Syncytial Virus Monoclonal Antibody, Reduces Hospitalization From Respiratory Syncytial Virus Infection in High-risk Infants," *Pediatrics* 102(3):531-537, 1998.

(Continued)

*Primary Examiner* — Jeffrey E. Russel
(74) *Attorney, Agent, or Firm* — Seed Intellectual Property Law Group LLP

(57) ABSTRACT

Disclosed herein are compositions and methods for inhibiting respiratory syncytial virus (RSV) entry into a host cell. Also provided herein are methods of identifying a peptide that interacts with the N-trimer of RSV F protein.

**36 Claims, 18 Drawing Sheets
Specification includes a Sequence Listing.**

(56) References Cited

OTHER PUBLICATIONS

Andabaka et al., "Monoclonal antibody for reducing the risk of respiratory syncytial virus infection in children (Review)," *Cochrane Database of Systematic Review* 4:CD006602, 2013 (134 pages).
Andries et al., "Substituted benzimidazoles with nanomolar activity against respiratory syncytial virus," *Antiviral Research* 60(3):209-219, 2003.
Baggiolini et al., "Interleukin-8, a chemotactic and inflammatory cytokine," *FEBS* 307(1):97-101, 1992.
Benner, "Expanding the Genetic lexicon: incorporating non-standard amino acids into proteins by ribosome-based synthesis," *Trends in Biotechnology* 12(5):158-163, 1994.
Bonfanti et al., "Selection of a Respiratory Syncytial Virus Fusion Inhibitor Clinical Candidate. 2. Discovery of a Morpholinopropylaminobenzimidazole Derivative (TMC353121)," *J. Med. Chem.* 51(4):875-896, 2008.
Carbonell-Estrany et al., "Motavizumab for Prophylaxis of Respiratory Syncytial Virus in High-Risk Children: A Noninferiority Trial," *Pediatrics* 125(1):35-e51, 2010.
Chi et al., "Molecular Epidemiology and Phylodynamics of the Human Respiratory Syncytial Virus Fusion Protein in Northern Taiwan," *PLOS ONE* 8(5):e64012, 2013. (9 pages).
Clark-Lewis et al., "Structural Requirements for Interleukin-8 Function Identified by Design of Analogs and CXC Chemokine Hybrids," *The Journal of Biological Chemistry* 269(23):16075-16081, 1994.
Dawson et al., "Synthesis of Proteins by Native Chemical Ligation," *Science* 266:776-779, 1994.
Denton et al., "One Percent Tenofovir Applied Topically to Humanized BLT Mice and Used According to the CAPRISA 004 Experimental Design Demonstrates Partial Protection from Vaginal HIV Infection, Validating the BLT Model for Evaluation of New Microbicide Candidates," *Journal of Virology* 85(15):7582-7593, 2011.
Dintzis et al., "A comparison of the immunogenicity of a pair of enantiomeric proteins," *Proteins* 16(3):306-308, 1993.
Domachowske et al., "Respiratory Syncytial Virus Infection: Immune Response, Immunopathogenesis, and Treatment," *Clinical Microbiology Reviews* 12(2):298-309, 1999.
Douglas et al., "Small Molecules VP-14637 and JNJ-2408068 Inhibit Respiratory Syncytial Virus Fusion by Similar Mechanisms," *Antimicrob. Agents Chemother.* 49(6):2460-2466, 2005.
Eckert et al., "Design of potent inhibitors of HIV-1 entry from the gp41 N-peptide region," *Proceedings of the National Academy of Sciences of the United States of America* 98(20):11187-11192, 2001.
Eckert et al., "Inhibiting HIV-1 Entry: Discovery of D-Peptide Inhibitors that Target the gp41 Coiled-Coil Pocket," *Cell* 99(1):103-115, 1999.
Eckert et al., "Mechanisms of Viral Membrane Fusion and Its Inhibition," *Annu. Rev. Biochem.* 70:777-810, 2001. (36 pages).
Falsey et al., "Respiratory Syncytial Virus Infection in Elderly and High-Risk Adults," *The New England Journal of Medicine* 352(17):1749-1759, 2005.
Francis et al., "Design of a modular tetrameric scaffold for the synthesis of membrane-localized D-peptide inhibitors of HIV-1 entry," *Bioconjugate Chemistry* 23(6):1252-1258, 2012. (15 pages).
Gem, "Viral Respiratory Infection and the Link to Asthma," *Pediatr Infect Dis J.* 27(10 0):S97-S103, 2008.
Hall et al., "The Burden of Respiratory Syncytial Virus Infection in Young Children," *The New England Journal of Medicine* 360:6:588-598, 2009.
Huntley et al., "RFI-641, a Potent Respiratory Syncytial Virus Inhibitor," *Antimicrobial Agents and Chemotherapy* 46(3):841-847, 2002.
Ibba et al., "Towards Engineering Proteins by Site-Directed Incorporation In Vivo of Non-Natural amino Acids," *Bio/Technology* 12:678-682, 1994.
Ibba, "Strategies for in vitro and in vivo translation with non-natural amino acids," *Biotechnology and Genetic Engineering Reviews* 13(1):197-216, 1996.
International Search Report and Written Opinion, dated Jan. 16, 2017, for International Application No. PCT/US2016/049155, 12 pages.
Lamb et al., "Structural basis of viral invasion: lessons from paramyxovirus F," *Curr. Opin. Struct. Biol.* 17(4):427-436, 2007.
Lambert et al., "Peptides from conserved regions of paramyxovirus fusion (F) proteins are potent inhibitors of viral fusion," *Proc. Natl. Acad. Sci. USA* 93:2186-2191, 1996.
Makari et al., "Impact of RSV: Implications for Managed Care," *Managed Care* 81(1):Supplement, 2009, 8 pages.
Milton et al., "Total Chemical Synthesis of a D-Enzyme: The Enantiomers of HIV-1 Protease Show Demonstration of Reciprocal Chiral Substrate Specificity," *Science* 256(5062):1445-1448, 1992.
Nair et al., "Global burden of acute lower respiratory infections due to respiratory syncytial virus in young children: a systematic review and meta-analysis," *Lancet* 375(9725):1545-1555, 2010.
Olszewska et al., "Antiviral and lung protective activity of a novel respiratory syncytial virus fusion inhibitor in a mouse model," *Eur. Respir. J.* 38(2):401-408, 2011.
Papenburg et al., "Molecular Evolution of Respiratory Syncytial Virus Fusion Gene, Canada, 2006-2010," *Emerging Infectious Diseases* 18(1):120-124, 2012.
Razinkov et al., "RFI-641 inhibits entry of respiratory syncytial virus via interactions with fusion protein," *Chemistry & Biology* 8:645-659, 2001.
Roymans et al., "Binding of a potent small-molecule inhibitor of six-helix bundle formation requires interactions with both heptad-repeats of the RSV fusion protein," *PNAS* 107(1):308-313, 2010.
Rudraraju et al., "Respiratory Syncytial Virus: Current Progress in Vaccine Development," *Viruses* 5:577-594, 2013.
Sadowski et al., "A Synthetic Peptide Blocking the Apolipoprotein E/β-Amyloid Binding Mitigates β-Amyloid Toxicity and Fibril Formation in Vitro and Reduces β-Amyloid Plaques in Transgenic Mice," *American Journal of Pathology* 165(3):937-948, 2004.
Schnölzer et al., "Constructing Proteins by Dovetailing Unprotected Synthetic Peptides: Backbone-Engineered HIV Protease," *Science* 256:221-225, 1992.
Schumacher et al., "Identification of $_D$-Peptide Ligands Through Mirror-Image Phage Display," *Science* 271:1854-1857, 1996.
Welch et al., "Design of a Potent d-Peptide HIV-1 Entry Inhibitor with a Strong Barrier to Resistance," *Journal of Virology* 84(21):11235-11244, 2010. (11 pages).
Welch et al., "Potent D-peptide inhibitors of HIV-1 entry," *Proceedings of the National Academy of Sciences of the United States of America* 104(43):16828-16833, 2007.
Welch et al., "Discovery and Design of Potent D-Peptide Inhibitors of HIV-1 Entry," West Coast Retrovirus Meeting, Palm Springs, California, Oct. 2007. (20 pages).
Welch, "D-Peptide inhibitors of RSV entry," *From Flu to Paraflu and Beyond: Honoring Four Decades of RNA Virus Research and Teaching*, Northwestern University, Aug. 29, 2015. (25 pages).
Zhao et al., "Structural characterization of the human respiratory syncytial virus fusion protein core," *PNAS* 97(26):14172-14177, 2000.

\* cited by examiner

COMPOSITIONS AND METHODS RELATED TO INHIBITION OF RESPIRATORY SYNCYTIAL VIRUS ENTRY

STATEMENT OF GOVERNMENT INTEREST

This invention was made with government support under Grant numbers GM066521 and AI076168 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690181_404USPC_SEQUENCE_LISTING.txt. The text file 85.8 KB, was created on Mar. 26, 2020, and is being submitted electronically via EFS-Web.

BACKGROUND

Respiratory syncytial virus (RSV) is an enveloped, negative-sense RNA virus that is one of many serious pathogens in the Paramyxoviridae family. RSV is a leading cause of serious lower respiratory tract infections in infants. 2-3% of children with RSV require hospitalization, making it the most frequent cause of hospitalization in children under age 2 in the US and age 5 worldwide (Hall et al., 2009, N. Eng. J. Med. 360:588-98; Nair et al., 2010, Lancet 375:1545-1555). Nearly everyone contracts RSV by 2 years of age, and reinfection occurs throughout life because immunity after infection is neither complete nor durable (Domachowske & Rosenberg, 1999, Clin. Microbiol. Rev. 12:298-309; Glezen et al., 1981, J. Pediatr. 98:708-15). Severe RSV early in life may have long-term sequelae, as it is a risk factor for asthma in adolescence (Gem, 2008, Pediatr. Infect. Dis. 27:S97-103). Recent studies show that RSV commonly causes severe cold-like symptoms in healthy adults (Hashem, 2003, J. Clin. Virol. 27:14-21). Furthermore, RSV is a significant cause of morbidity and mortality in the elderly, with mortality rates as high as 8% in elderly with congestive heart failure or chronic pulmonary disease (Falsey et al., 2005, N. Engl. J. Med. 352:1749-59). The overall RSV burden on the US healthcare system is estimated to be ~$2 billion annually (Falsey et al., 2005, N. Engl. J. Med. 352:1749-59; Makari et al., 2009, Manag. Care 18:2-7).

Currently, no vaccines or safe and effective RSV therapeutics are available, and treatment is limited to supportive care and, for the most desperate cases, administration of ribavirin, a broad antiviral with questionable efficacy and known toxicity (Broughton & Greenough, 2004, Curr. Opin. Investig. Drugs 5:862-5). Synagis (palivizumab), a monoclonal antibody (mAb) given prophylactically throughout RSV season, is partially effective at preventing the severe complications associated with RSV infection in the lower respiratory tract (Andabaka et al., 2013, Cochrane Database Syst. Rev. 4:CD006602). However, Synagis is only available to the highest risk infants and certain children <2 years old with chronic lung or congenital heart disease. Synagis is dosed at 15 mg/kg of body weight and a typical 5-month course for premature infants costs ~$6,000. The high cost of Synagis prohibits its use in broader patient populations. Furthermore, it only reduces hospitalizations by 55% among high-risk infants (Palivizumab. Pediatrics, 1998, 102:531-7). Despite addressing only a small subset of potential RSV patients and its moderate efficacy, sales of Synagis in 2012 were >$1 billion. The FDA recently rejected a more potent follow-up antibody (motavizumab) due to increased toxicity and only "non-inferior" efficacy (trials were not designed to demonstrate superiority) (Carbonell-Estrany et al., 2010, Pediatrics 125:e35-51).

Several vaccine candidates are in early clinical development, but they must overcome the problems of early vaccine efforts that substantially exacerbated RSV infection by a still unclear mechanism (Rudraraju et al., 2013, Viruses 5:577-594). Additionally, since primary infection and maternal antibodies are often insufficient to provide adequate and lasting protection, it is clear that an effective vaccine would have to produce a superior immune response than natural infection. This goal is especially challenging in young infants with underdeveloped immune responses. Indeed, no vaccines for respiratory viruses are approved for use in infants <6 months old (Beeler & Eichelberger 2013, Microb. Pathog. 55:9-15).

There is a need for improved approaches to RSV treatment, for example, inhibitors of RSV entry into cells. The present disclosure provides approaches and embodiments addressing such needs and further provides other related advantages.

BRIEF SUMMARY

Embodiment 1

An isolated D-peptide that is capable of interacting with the N-trimer groove of respiratory syncytial virus (RSV) F protein.

Embodiment 2

The isolated D-peptide of embodiment 1, wherein the D-peptide is capable of inhibiting RSV entry into a host cell.

Embodiment 3

The isolated D-peptide of any preceding embodiment, wherein the D-peptide is capable of interacting with the N-trimer groove of RSV-A and RSV-B.

Embodiment 4

The isolated D-peptide of any preceding embodiment, wherein the D-peptide is capable of inhibiting entry of RSV-A and RSV-B into a host cell.

Embodiment 5

The isolated D-peptide of any preceding embodiment, wherein the D-peptide is linked to an identical D-peptide.

Embodiment 6

The isolated D-peptide of any preceding embodiment, wherein the D-peptide is linked to two identical D-peptides.

Embodiment 7

The isolated D-peptide according to any preceding embodiment, wherein the D-peptide comprises an amino acid sequence as set forth in SEQ ID NO:1 or SEQ ID NO:41.

Embodiment 8

The isolated D-peptide according to any one of embodiments 1-6, wherein the D-peptide comprises an amino acid sequence as set forth in SEQ ID NO:65.

Embodiment 9

The isolated D-peptide according to any one of embodiments 1-6, wherein the D-peptide comprises an amino acid sequence as set forth in SEQ ID NO:2 or SEQ ID NO:42.

Embodiment 10

The isolated D-peptide according to any one of embodiments 1-6, wherein the D-peptide comprises an amino acid sequence as set forth in SEQ ID NO:66.

Embodiment 11

The isolated D-peptide according to any one of embodiments 7-10, wherein the D-peptide comprises an amino acid sequence selected from Table 2 (SEQ ID NOS:3-31).

Embodiment 12

The isolated D-peptide according to any one of embodiments 7-11, wherein the D-peptide comprises RSVP7 (SEQ ID NO:16), RSVP11 (SEQ ID NO:17), RSVP24 (SEQ ID NO:23), RSVP25 (SEQ ID NO:24), RSVP26 (SEQ ID NO:25), RSVP27 (SEQ ID NO:26), RSVP28, (SEQ ID NO:27) RSVP29 (SEQ ID NO:28), RSVP30 (SEQ ID NO:29), RSVP31 (SEQ ID NO:30), or RSVP32 (SEQ ID NO:31).

Embodiment 13

The isolated D-peptide according to any one of embodiments 1-6, wherein the D-peptide comprises an amino acid sequence selected from Table 8 (SEQ ID NOS:147-159).

Embodiment 14

The isolated D-peptide according to any one of embodiments 1-6, wherein the D-peptide comprises an amino acid sequence selected from Table 9 (SEQ ID NOS:167, 168, 173, 200, 202, 207, and 217-219).

Embodiment 15

The isolated D-peptide according to any one of embodiments 1-6, wherein the D-peptide comprises an amino acid sequence selected from Table 10 (SEQ ID NOS:160-213).

Embodiment 16

The isolated D-peptide according to embodiment 15, wherein the D-peptide comprises an amino acid sequence as set forth in SEQ ID NOS:160-166.

Embodiment 17

The isolated D-peptide of any one of embodiments 1-16, wherein the N-terminus of the D-peptide is capped with an acetyl group.

Embodiment 18

The isolated D-peptide of any one of embodiments 1-17, wherein the C-terminus of the D-peptide is capped with an amide group.

Embodiment 19

The isolated D-peptide of any one of embodiments 1-6, wherein the D-peptide comprises an amino acid sequence selected from Table 7 (SEQ ID NOS:73-146 and 214-216).

Embodiment 20

The isolated D-peptide of any one of embodiments 1-6, wherein the D-peptide comprises the amino acid sequence Ac-K(PEG4)-DDG-GECVNRPEWLLDWCGT-NH2 (SEQ ID NO:142).

Embodiment 21

The isolated D-peptide of any one of embodiments 1-6, wherein the D-peptide comprises the amino acid sequence Ac-K(PEG4)-EEG-GECVNRPEWLLDWCGT-NH2 (SEQ ID NO:214).

Embodiment 22

An isolated composition comprising a first D-peptide that is capable of interacting with the N-trimer groove of respiratory syncytial virus (RSV) F protein.

Embodiment 23

The isolated composition of embodiment 21, wherein the first D-peptide is capable of inhibiting RSV entry into a host cell.

Embodiment 24

The isolated composition according to any one of embodiment 22 or embodiment 23, wherein the first D-peptide is capable of interacting with the N-trimer groove of RSV-A and RSV-B.

Embodiment 25

The isolated composition according to any one of embodiments 22-24, wherein the first D-peptide is capable of inhibiting entry of RSV-A and RSV-B into a host cell.

Embodiment 26

The isolated composition according to any one of embodiments 22-25, wherein the first D-peptide is linked to a second D-peptide.

Embodiment 27

The isolated composition according to embodiment 26, wherein the second D-peptide is identical to the first D-peptide.

Embodiment 28

The isolated composition according to any one of embodiments 26 or embodiment 27, wherein the first D-peptide is linked to a third D-peptide.

Embodiment 29

The isolated composition to embodiment 28, wherein the third D-peptide is identical to the first D-peptide.

Embodiment 30

The isolated composition according to any one of embodiments 26-29, wherein the first D-peptide and the second D-peptide, or the first D-peptide, the second D-peptide, and the third D-peptide, are multimerized through a cross-linker.

Embodiment 31

The isolated composition of embodiment 30, wherein the cross-linker is a polyethylene glycol (PEG) linker.

Embodiment 32

The isolated composition according to any one of embodiments 30-31, wherein the N-termini of the D-peptides are cross-linked.

Embodiment 33

The isolated composition according to any one of embodiments 30-31, wherein the C-termini of the D-peptides are cross-linked.

Embodiment 34

The isolated composition according to any one of embodiments 30-31, wherein the N-terminus or C-terminus of each D-peptide is cross-linked.

Embodiment 35

The isolated composition according to any one of embodiments 26-29, wherein the first D-peptide and the second D-peptide, or the first D-peptide, the second D-peptide, and the third D-peptide, are multimerized through a scaffold having the following structure:

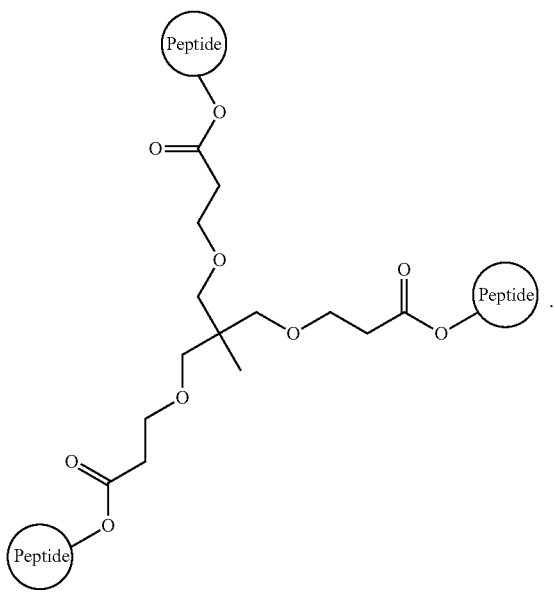 [SMILES: COC(=O)CCOCC(C)(COCCC(=O)OC)COCCC(=O)OC]

Embodiment 36

The isolated composition according to any one of embodiments 26-29, wherein the first D-peptide and the second D-peptide, or the first D-peptide, the second D-peptide, and the third D-peptide, are multimerized through a scaffold having the following structure:

Embodiment 37

The isolated composition according to any one of embodiments 26-29, wherein the first D-peptide and the second D-peptide, or the first D-peptide, the second D-peptide, and the third D-peptide, are multimerized through a scaffold having the following structure:

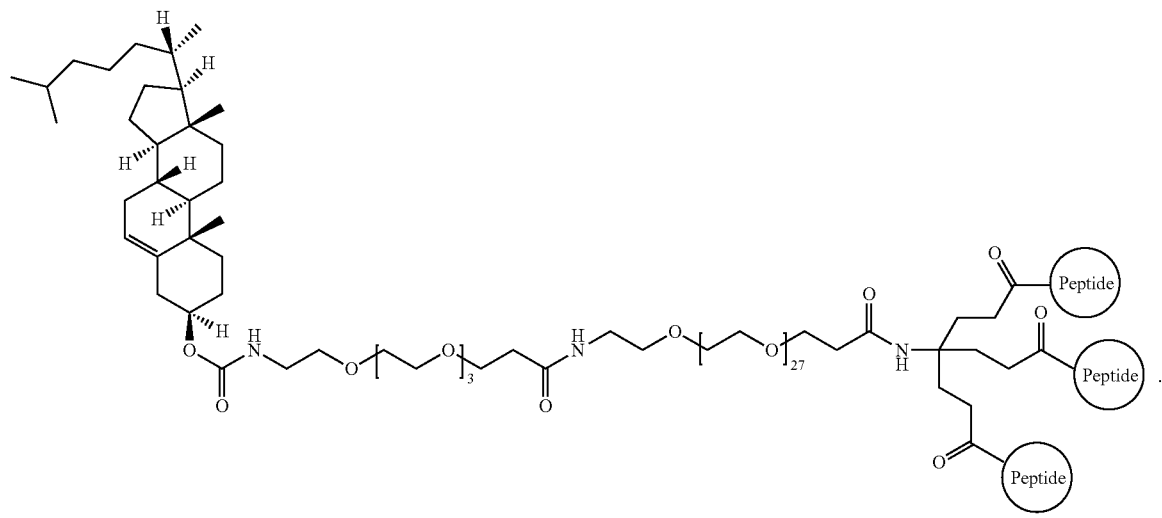

Embodiment 38

The isolated composition according to any one of embodiments 26-29, wherein the first D-peptide and the second D-peptide, or the first D-peptide, the second D-peptide, and the third D-peptide, are multimerized through the following structure:

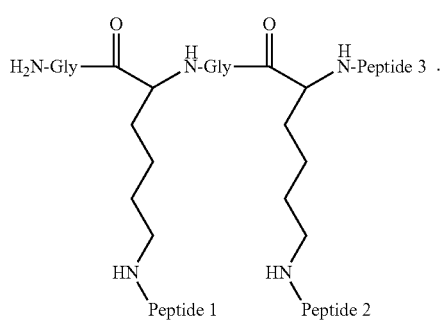

Embodiment 39

The isolated composition according to any one of embodiments 26-29, wherein the first D-peptide and the second D-peptide, or the first D-peptide, the second D-peptide, and the third D-peptide, are multimerized through the following structure:

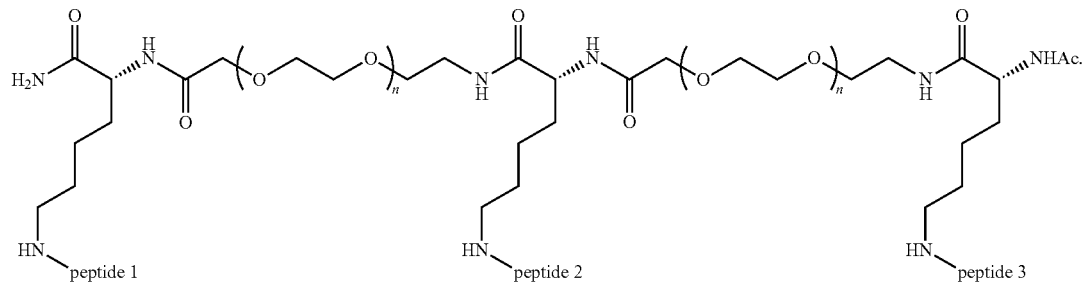

Embodiment 40

The isolated composition according to any one of embodiments 35-37, wherein the N-termini of the D-peptides are attached to the scaffold.

Embodiment 41

The isolated composition according to any one of embodiments 35-39, wherein the C-termini of the D-peptides are attached to the scaffold.

Embodiment 42

The isolated composition according to any one of embodiments 35-37, wherein the N-terminus or C-terminus of each D-peptide is attached to the scaffold.

Embodiment 43

The isolated composition according to any one of embodiments 22-42, wherein the first D-peptide comprises an amino acid sequence as set forth in SEQ ID NO:1 or SEQ ID NO: 41.

Embodiment 44

The isolated composition according to any one of embodiments 22-42, wherein the first D-peptide comprises an amino acid sequence as set forth in SEQ ID NO:65.

Embodiment 45

The isolated composition according to any one of embodiments 22-42, wherein the first D-peptide comprises an amino acid sequence as set forth in SEQ ID NO:2 or SEQ ID NO:42, wherein X is any amino acid except cysteine.

Embodiment 46

The isolated composition according to any one of embodiments 22-42, wherein the first D-peptide comprises an amino acid sequence as set forth in SEQ ID NO:66.

Embodiment 47

The isolated composition according to any one of embodiments 43-46, wherein the first D-peptide comprises an amino acid sequence selected from Table 2 (SEQ ID NOS: 3-31).

Embodiment 48

The isolated composition of embodiment 43 or embodiment 45, wherein the first D-peptide comprises RSVP7 (SEQ ID NO:16), RSVP11 (SEQ ID NO:17), RSVP24 (SEQ ID NO:23), RSVP25 (SEQ ID NO:24), RSVP26 (SEQ ID NO:25), RSVP27 (SEQ ID NO:26), RSVP28, (SEQ ID NO:27) RSVP29 (SEQ ID NO:28), RSVP30 (SEQ ID NO:29), RSVP31 (SEQ ID NO:30), or RSVP32 (SEQ ID NO:31).

Embodiment 49

The isolated composition of any one of embodiments 43-48, wherein the N-terminus of the D-peptide is capped with an acetyl group.

Embodiment 50

The isolated composition of any one of embodiments 43-49, wherein the C-terminus of the D-peptide is capped with an amide group.

Embodiment 51

The isolated composition of any one of embodiments 22-50, wherein the first D-peptide comprises an amino acid sequence selected from Table 7 (SEQ ID NOS:73-146, and 214-216).

Embodiment 52

The isolated composition of embodiment 51, wherein the first D-peptide comprises the amino acid sequence Ac-K(PEG4)-DDG-GECVNRPEWLLDWCGT-NH2 (SEQ ID NO:142).

Embodiment 53

The isolated composition of embodiment 51, wherein the first D-peptide comprises the amino acid sequence Ac-K(PEG4)-EEG-GECVNRPEWLLDWCGT-NH2 (SEQ ID NO:214).

Embodiment 54

The isolated composition of embodiment 37, wherein each of the first, second, and third D-peptide comprises the amino acid sequence Ac-K(PEG4)-DDG-GECVNRPEWLLDWCGT-NH2 (SEQ ID NO:142).

Embodiment 55

The isolated composition of embodiment 37, wherein each of the first, second, and third D-peptide comprises the amino acid sequence Ac-K(PEG4)-EEG-GECVNRPEWLLDWCGT-NH2 (SEQ ID NO:214).

Embodiment 56

The isolated composition of any one of embodiments 22-50, wherein the first D-peptide comprises an amino acid sequence selected from Table 8 (SEQ ID NOS:147-159).

Embodiment 57

The isolated composition of any one of embodiments 2-50, wherein the first D-peptide comprises an amino acid sequence selected from Table 10 (SEQ ID NOS:160-213).

Embodiment 58

The isolated composition of any one of embodiments 21-49, wherein the first D-peptide comprises an amino acid sequence selected from Table 9 (SEQ ID NOS: 167, 168, 173, 200, 202, 207, 217, 218, and 219).

Embodiment 59

The isolated composition of any one of embodiments 21-49, wherein the first D-peptide comprises an amino acid sequence selected from Table 10 (SEQ ID NOS:160-213).

Embodiment 60

The isolated composition of according to any one of embodiments 22-59, wherein at least one D-peptide is linked to a potency enhancing cargo molecule.

Embodiment 61

The isolated composition of embodiment 60, wherein the potency enhancing cargo molecule is a cholesterol, sterol, sugar, maltose binding protein, ubiquitin, streptavidin, immunoglobulin domain, keyhole limpet hemacyanin, sperm whale myoovalbumin, bovine pancreatic trypsin inhibitor, green fluorescent protein, gold particle, magnetic particle, agarose bead, lactose bead, fatty acid, a high molecular weight PEG, or serum albumin.

Embodiment 62

The isolated composition of embodiment 60 or 61, wherein the potency enhancing cargo molecule is linked to the at least one D-peptide with a PEG linker.

Embodiment 63

The isolated composition according to any one of embodiments 28-62, wherein a trimer of D-peptides exhibits enhanced binding affinity or anti-viral activity as compared with the binding affinity or anti-viral activity of an isolated composition comprising the first D-peptide as a monomer.

Embodiment 64

The isolated composition according to any one of embodiments 28-63, wherein the composition further comprises a pharmaceutically acceptable carrier.

Embodiment 65

The isolated composition according to embodiment 54, wherein the composition further comprises a pharmaceutically acceptable carrier.

Embodiment 66

The isolated composition according to embodiment 55, wherein the composition further comprises a pharmaceutically acceptable carrier.

Embodiment 67

A method for inhibiting entry of respiratory syncytial virus (RSV) into a host cell, comprising exposing the RSV virus to the D-peptide according to any one of embodiments 1-20, or the composition according to any one of embodiments 22-66, thereby inhibiting entry of the virus into the host cell.

Embodiment 68

The method according to embodiment 67, wherein the pharmaceutical composition comprises an amino acid sequence as set forth in SEQ ID NO:142.

Embodiment 69

The method according to embodiment 67, wherein the pharmaceutical composition comprises an amino acid sequence as set forth in SEQ ID NO:214.

Embodiment 70

The method according to embodiment 67, wherein a first D-peptide, a second D-peptide, and a third D-peptide, are multimerized through a scaffold having the following structure:

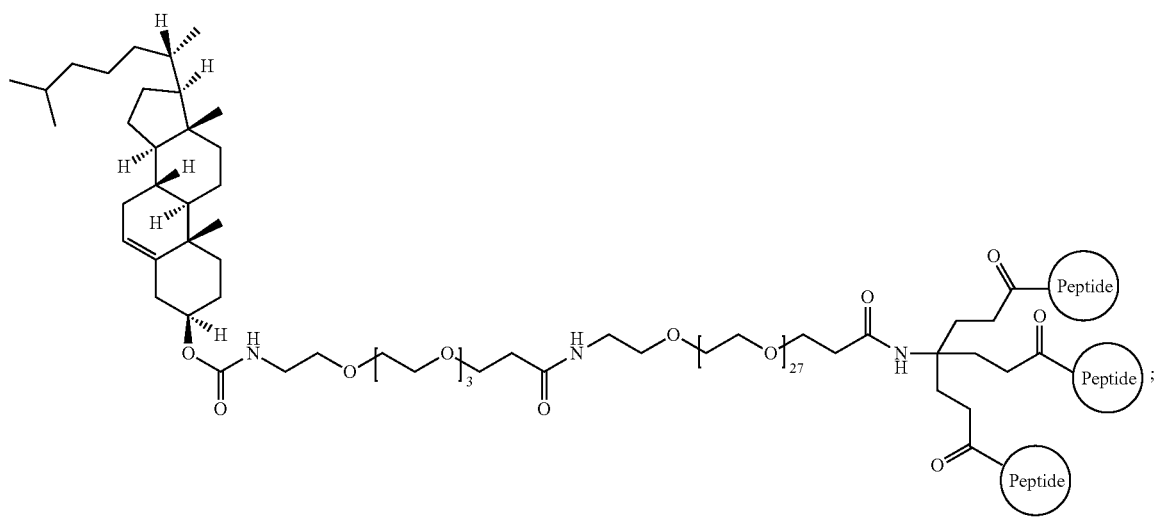

and each of the first, second, and third D-peptides comprises an amino acid sequence as set forth in SEQ ID NO:142.

Embodiment 71

The method according to embodiment 67, wherein a first D-peptide, a second D-peptide, and a third D-peptide, are multimerized through a scaffold having the following structure:

and each of the first, second, and third D-peptides comprises an amino acid sequence as set forth in SEQ ID NO:214.

Embodiment 72

A method of treating respiratory syncytial virus (RSV) infection in a subject, comprising administering to the subject a therapeutically effective amount of the D-peptide according to any one of embodiments 1-21, or the composition according to any one of embodiments 22-66.

Embodiment 73

The method according to embodiment 72, comprising administering to the subject a therapeutically effective amount of a D-peptide according to embodiment 20.

Embodiment 74

The method according to embodiment 72, comprising administering to the subject a therapeutically effective amount of a D-peptide according to embodiment 21.

Embodiment 75

The method according to embodiment 72, comprising administering to the subject a therapeutically effective amount a composition according to embodiment 54.

Embodiment 76

The method according to embodiment 72, comprising administering to the subject a therapeutically effective amount a composition according to embodiment 55.

Embodiment 77

The method according to any one of embodiments 67-76, wherein the D-peptide or composition is administered concurrently or sequentially with at least one additional anti-viral agent.

Embodiment 78

The method of embodiment 77, wherein the at least one additional anti-viral agent is a viral fusion inhibitor, viral attachment inhibitor, viral replication inhibitor, a viral protease inhibitor, an inhibitor antibody, a biologic, an antisense molecule, an RNA interference agent, a peptide, or a small molecule.

Embodiment 79

A method of identifying a peptide that interacts with the N-trimer groove of respiratory syncytial virus (RSV) F protein comprising: (a) exposing at least one test peptide to an N-trimer mimic of the RSV F protein, and (b) identifying which test peptide interacts with the N-trimer mimic of the RSV F protein, wherein a test peptide that interacts with the N-trimer mimic is identified as a peptide that interacts with the N-trimer groove.

Embodiment 80

The method of embodiment 79, wherein the N-trimer mimic comprises a portion of the N-trimer groove of RSV F protein.

Embodiment 81

The method of embodiment 79, wherein the N-trimer mimic comprises the entire N-trimer groove of RSV F protein.

Embodiment 82

The method according to any one of embodiments 79-81, wherein the N-trimer mimic comprises a homotrimer of an amino acid sequence selected from Table 3 (SEQ ID NOS: 32-40).

Embodiment 83

The method according to any one of embodiments 79-81, wherein the N-trimer mimic is fused to a soluble trimeric coiled-coil peptide.

Embodiment 84

The method of embodiment 82, wherein the soluble trimeric coiled-coil peptide is an isoleucine zipper trimer.

Embodiment 85

The method of embodiment 73 or embodiment 84, wherein the N-trimer mimic is fused at its N-terminus to the soluble trimeric coiled-coil.

Embodiment 86

The method according to any one of embodiments 79-83, wherein a library of test peptides is exposed to the N-trimer mimic.

Embodiment 87

The method of embodiment 86, wherein mirror image phage display is used to identify the peptide that interacts with the N-trimer groove.

Embodiment 88

The method of embodiment 86 or embodiment 87, wherein steps (a) and (b) are repeated one or more times with the library of test peptides.

Embodiment 89

The method of embodiment 87, wherein the test peptide identified as interacting with the N-trimer groove is synthesized as a D-peptide.

Embodiment 90

A multimer having the formula:

Embodiment 91

The multimer according to embodiment 90, wherein Peptide 1, Peptide 2, and Peptide 3 are identical.

Embodiment 92

The multimer according to embodiment 90 or embodiment 91, wherein one or more of Peptide 1, Peptide 2, and Peptide 3 is a D-peptide.

Embodiment 93

A multimer having the formula:

Embodiment 94

The multimer according to embodiment 93, wherein peptide 1, peptide 2, and peptide 3 are identical.

Embodiment 95

The multimer according to embodiment 93 or embodiment 94, wherein one or more of peptide 1, peptide 2, and peptide 3 is a D-peptide.

Embodiment 96

A method for preparing a multimeric molecule having two or more monomer peptides, comprising:

(1) protecting primary amines on the sidechain of one or more lysine residues;

(2) preparing a peptide or polymer that incorporates the one or more lysine residues;

(3) deprotecting the one or more lysine residues to reveal free primary amines on each lysine sidechain; and (4) growing peptide monomers at each free primary amine.

Embodiment 97

The method according to embodiment 98, wherein preparing the peptide or polymer that incorporates the lysine residues further comprises protecting the N-terminal amino group prior to deprotecting the lysine residues.

Embodiment 98

The method according to embodiment 96 or 97, wherein preparing the peptide or polymer that incorporates the lysine residues further comprises adjusting the spacing between peptide monomers by introducing variable numbers of glycine or flexible PEG units between the lysines.

BRIEF DESCRIPTION OF THE DRAWINGS

FIG. 5 depicts the crystal structure of the RSV N-trimer groove. Side chains of residues that differ between RSV A and B subtypes are displayed. The hydrophobic pocket, into which two phenylalanines and an isoleucine from the C-peptide (black coil) pack, is shown (indicated by area shaded with triangles). Different N-trimer mimics were designed comprising the entire groove, the segments indicated in the figure with crosshatch and triangle patterns, or the segment indicated with triangles.

FIG. 6 depicts another crystal structure of the RSV N-trimer groove. C-peptides are shown as black coils binding in the grooves of the N-trimer (surface). The locations of engineered disrupting mutations in RSV N-trimer mimic IZN45_Mut are shown in crosshatched shaded areas, and the scheme for 3 partial mutants used for mapping RSV peptide binding (IZN45_WT-Top, -Mid, and -Bot) is indicated. IZN45 and all 4 mutant versions were helical by CD with the characteristic spectra of coiled-coils (not shown). IZN45 target and mutants were initially constructed based on the RSV-B sequence. RSV-A versions were made later to confirm cross-reactivity of discovered D-peptides.

FIG. 7 depicts an embodiment of an RSV N-trimer mimic (or target) used to screen the mirror-image phage display library. IZN21 comprises a portion of the N-trimer groove, the hydrophobic pocket near the base of the N-trimer. A designed soluble trimeric coiled-coil IZ (isoleucine zipper) with high stability and solubility is fused in helical frame to various segments of the RSV N-trimer.

DETAILED DESCRIPTION

The instant disclosure provides D-peptides that can interact with the N-trimer groove of an RSV F protein, and, in some embodiments, inhibit RSV entry into a host cell. In certain aspects, the present disclosure provides pharmaceutical compositions and methods for treating RSV infection.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

Unless the context requires otherwise, throughout the present specification and claims, the word "comprise" and variations thereof, such as "comprises" and "comprising," are to be construed in an open, inclusive sense, that is, as "including, but not limited to". The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have," and "comprise" are used synonymously, which terms and variants thereof are intended to be construed as non-limiting.

Disclosed herein are novel, synthetic protease-resistant D-peptides (peptides composed of D-amino acids, the mirror images of natural L-amino acids) that inhibit RSV entry. D-peptides cannot be digested by natural proteases in the body, and therefore, possess potentially significant therapeutic advantages (Milton et al., 1992, Science 256:1445-8; Sadowski et al., 2004, Am. J. Pathol. 165:937-48), such as extended in vivo half-life and reduced immunogenicity since they are not digested for MHC presentation (Dintzis et al., 1993, Proteins 16:306-8). Another advantage is that D-peptides can be produced at a dramatically lower cost than monoclonal antibodies, such as SYNAGIS®.

Figure 1:
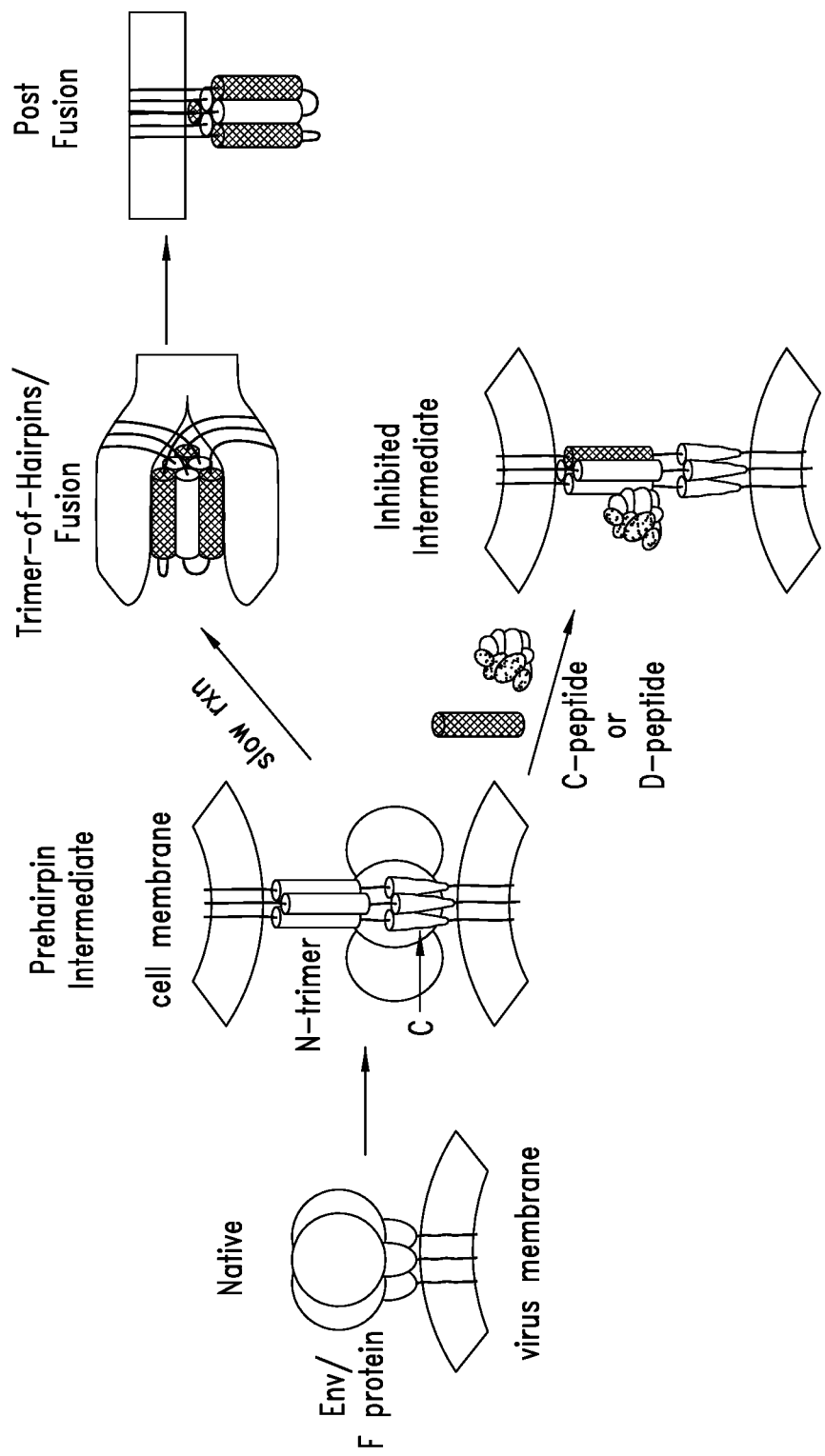
FIG. 1 depicts an RSV entry pathway. Fusion between RSV and host cell membranes is mediated by a glycoprotein on the surface of RSV (F protein). Host cell recognition by the RSV G protein leads to a transient conformation of the glycoprotein that is embedded in both the RSV and host cell membranes. This "prehairpin intermediate" exposes a trimeric coiled-coil formed by the N-terminal region (N-trimer) and a C-terminal region (C-peptide). Slow collapse of the intermediate into a high stable trimer-of-hairpins structure, with the C-peptides binding into the grooves on the N-trimer, juxtaposes the virus and cell membranes, leading to membrane fusion. Exogenous C-peptides, derived from the viral glycoprotein sequences of RSV, can bind the exposed N-trimer of RSV during the pre-hairpin intermediate phase and inhibit entry in a dominant-negative manner (Lambert et al., 1996, Proc. Natl. Acad. Sci. USA 93:2186-2191).

RSV mechanism of viral entry is depicted in FIG. 1 (also reviewed in Eckert & Kim, 2001, Annu. Rev. Biochem. 70:777-810; Lamb & Jardetzky, 2007, Curr. Opin. Struct. Biol. 17:427-36). To initiate viral infection, fusion between the viral and host cell membranes is mediated by a glycoprotein on the viral surface (F protein in RSV). Host cell recognition by distinct G protein of RSV leads to the formation of a transient conformation of the glycoprotein that is embedded in both the virus and host cell membranes. This "pre-hairpin intermediate" exposes a trimeric coiled-coil formed by the N-terminal region (N-trimer) and the unstructured C-terminal region (C-peptide). Slow collapse of the intermediate into a highly stable trimer-of-hairpins structure, with the C-peptide binding into the grooves on the N-trimer, juxtaposes the virus and cell membranes, leading to membrane fusion.

Exogenous C-peptides derived from the viral glycoprotein sequences of RSV can bind the pre-hairpin intermediate N-trimer of RSV and inhibit entry in a dominant-negative manner (Lambert et al., 1996, Proc. Natl. Acad. Sci. USA 93:2186-91). Without wishing to be bound by theory, RSV entry, the first step in RSV lifecycle is an ideal target for both prevention and treatment since intervention at this phase will likely protect against cytopathic effects, (e.g., syncytia formation or cell-cell fusion) seen in RSV-infected cells that would not be blocked by inhibitors that target phases after viral entry.

Figure 2:
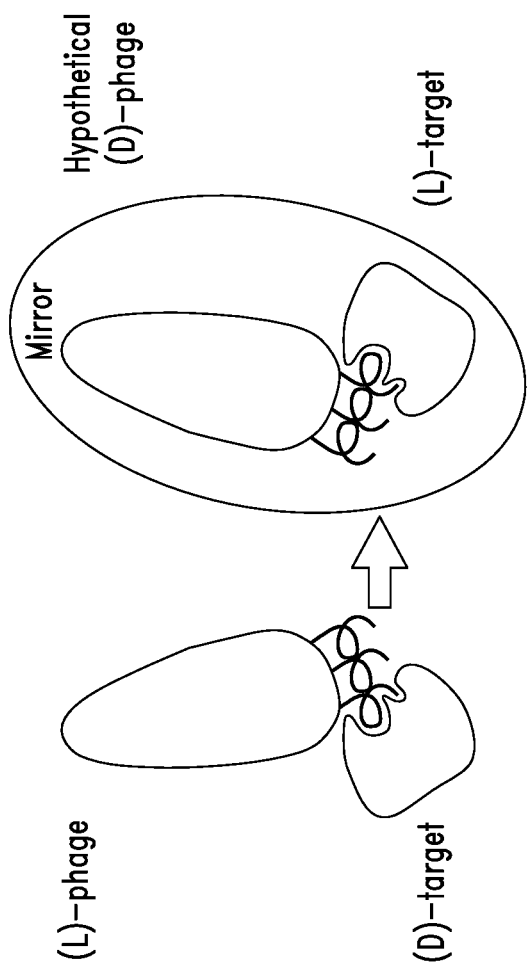
FIG. 2 depicts mirror-image phage display which may be used in identification of peptide ligands that bind to the RSV N-trimer. In mirror-image phage display, the screening target is made with D-amino amino acids using standard chemical synthesis and therefore folds into the mirror-structure of the natural target (made from L-amino acids). The phage library is screened against the mirror-image target to identify natural L-peptides on the phage that bind the D-target. These peptides are then chemically synthesized using D-amino acids. By law of symmetry, these D-peptides bind the natural L-target.
Figure 3:
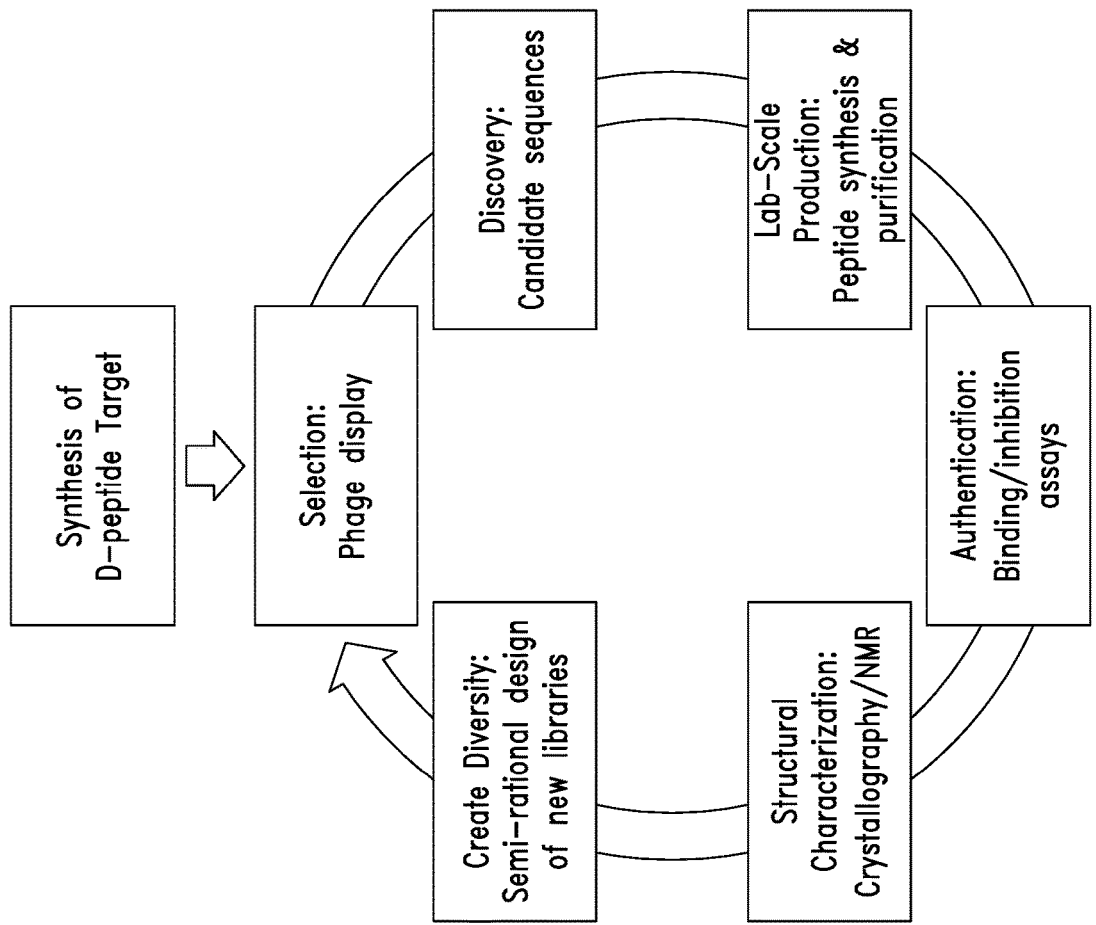
FIG. 3 depicts an embodiment of the D-peptide discovery/design cycle.

The present disclosure describes an innovative approach to drug discovery to identify novel, protease-resistant D-peptide inhibitors of RSV entry into host cells. These RSV D-peptide inhibitors are also referred to herein as RSVPs. Traditional phage display involves a process of screening a library of phage, each with a unique peptide displayed on its surface, against a target molecule in order to identify peptides that bind to the target. The phage links phenotype (target binding) to genotype (the genomic DNA encoding the surface peptide). The RSVPs described herein were discovered using a modification of traditional phage display called mirror-image phage display (see, FIG. 2) (see, Schumacher et al., 1996, Science 271:1854-7). In mirror-image phage display, the screening target molecule is chemically synthesized with D-amino acids and therefore forms the mirror-image structure of the natural L-target molecule. Phage display using the D-target molecule is performed, and L-peptides that bind the D-target molecule are then chemically synthesized with D-amino acids. By the law of symmetry, these D-peptides bind the natural L-target molecule. A scheme depicting the peptide discovery and design cycle is presented in FIG. 3.

As described herein, mirror-image phage display has been used to identify novel, synthetic, protease-resistant D-peptide inhibitors of the F protein. Small molecule inhibitors that were proposed to bind to the RSV F protein N-trimer pocket and inhibit membrane fusion with high pM to high nM potency have been reported (Andries et al., 2003, Antiviral Res. 60:209-19; Bonfanti et al., 2008, J. Med. Chem. 51:875-96; Douglas et al., 2005, Antimicrob Agents Chemother 49:2460-6; Razinkov et al., 2001, Chem. Biol. 8:645-59). Some of these compounds have shown efficacy post-exposure in animal models, providing proof of principle of the therapeutic potential of RSV entry inhibitors (Huntley et al., 2002, Antimicrob. Agents Chemother. 46:841-7; Olszewska et al., 2010, Eur. Respir. J., 2011, 38:401-8). However, viral resistance to these compounds was easily achieved in vitro, with mutations in the C-peptide region of the F protein leading to ~1000-fold loss in potency (Douglas et al., 2005, Antimicrob. Agents Chemother. 49:2460-6; Roymans et al., 2010, Proc. Natl. Acad. Sci. USA 107:308-13). High-resolution structural information and the surprising result that none of the resistance mutations were found in the pocket revealed that these inhibitors bind not only to the N-trimer pocket, but also to the C-peptide region of the F-protein and likely inhibit by distorting the trimer-of-hairpins structure, rather than preventing its formation. Only one of the three compounds remains under development and is still in the preclinical stage (Olszewska et al., 2011, Eur. Respir. J. 38:401-8).

The D-peptide inhibitors of RSV entry of the present disclosure have several important potential advantages over small molecule candidates. In some embodiments, the D-peptide prevents the large protein/protein interaction between the N-trimer and C-peptide (i.e., an undruggable target for small molecules). Therefore, it will have the potential of being highly potent (greater clinical efficacy) and specific (less toxicity). Since D-peptide inhibitors are protease resistant, they may have longer in vivo half-life, making it potentially feasible as a preventative drug and more convenient as a therapeutic drug. A long half-life provides benefits such as small and infrequent dosing as well as low cost. D-peptides inhibitors are also suited for mucosal delivery (e.g., inhalation) or extended release formulations for a long-acting preventative/therapeutic. Additionally, in some embodiments, the D-peptides described herein will target only the N-trimer, which is highly conserved and appears to be more resistant to mutation. The D-peptide inhibitors are specifically designed to combat the emergence of viral resistance, a challenge in developing effective antivirals. A similar D-peptide with a similar mechanism of action to some embodiments described herein, but designed to act against HIV instead of RSV, has been shown to possess a novel 'resistance capacitor,' which takes advantage of the transient exposure of the pre-hairpin intermediate that uncouples the inhibitor's affinity and potency (see, e.g., Welch et al., 2010, J. Virol. 84:11235-44, Welch et al., 2007, Proc. Natl. Acad. Sci. USA 104:16828-33; *PIE12 D-peptide trimer having an extraordinarily robust resistance profile*). For example, in standard viral passaging studies in the presence of escalating D-peptide inhibitor, PIE12 trimer resistance develops in 65 weeks vs. 2-3 weeks for the FDA-approved HIV entry inhibitor, Fuzeon.

Compositions

Disclosed herein are components to be used to prepare the disclosed compositions, as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular peptide is disclosed in a multimer, and a number of modifications that can be made to a number of molecules including the peptide are discussed, specifically contemplated is each and every combination and permutation of the peptide in the multimer with other peptides in the multimer, as well as the modifications to the peptides that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including steps in methods of making and using the disclosed compositions. Thus, if there are a variety of additional steps that can be performed it is understood that each of these additional steps can be performed with any specific embodiment or combination of embodiments of the disclosed methods.

Peptides

Disclosed herein are peptides and multimers of those peptides. For example, disclosed is a peptide which interacts with the N-trimer groove of a RSV transmembrane F protein. For example, in some embodiments, a peptide as disclosed herein binds to a cavity on the surface of the N-helix coiled-coil of RSV glycoprotein F (e.g., RSV-A, RSV-B). In some embodiments, the peptide interacts with the N-trimer pocket of RSV. Such peptides can be of any length, provided that they are of sufficient length to bind the N-trimer groove in such a manner that they interfere with the interaction of the N-helix coiled-coil cavity and amino acid residues of the C-peptide region of RSV F protein and prevent, or inhibit, RSV entry into the cells. For example, a D-peptide monomer of the present disclosure can comprise at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues in length. In certain embodiments, the D-peptide monomer comprises 10-25 amino acids in length, or 12-23 amino acids in length. The amino acid residues can be naturally occurring or non-naturally occurring or modified, as described below. The peptides can be linear or circular.

The term "D-amino acid residue", as used herein, refers to an α-amino acid residue having the same absolute configuration as D-glyceraldehyde. When the amino acid residue includes a first non-hydrogen α-substituent and a second α-substituent selected from methyl and halogen, the absolute configuration is the same as that of D-glyceraldehyde with the second α-substituent taking the place of the hydrogen atom at the glyceraldehyde α-carbon.

The term "D-peptide," as used herein, refers to peptide composed of D-amino acid residues.

The term "host cell," as used herein, refers to cells of human or non-human primates.

By "inhibit RSV entry" is meant a reduction in the number of RSV particles that are capable of entering a cell. It can mean complete inhibition, in other words no viral particles are capable of entering a cell, or it can mean a partial inhibition, meaning that in a given system there is a reduction in the number of viral particles capable of entering a cell when compared with a non-treated system, or a control. There can be a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96, 97%, 98%, 99%, or 100% reduction in the number of viral particles that are capable of entering a cell, or any amount greater, less, or in between these amounts.

In some embodiments, D-peptides comprising a consensus sequence disclosed in Table 1 (SEQ ID NOS:1, 2, or 41) are used with the compositions and methods disclosed herein. In further embodiments, D-peptides comprising an amino acid sequence disclosed in Table 2 (SEQ ID NOS:3-31) are used with the compositions and methods disclosed herein. In yet further embodiments, D-peptides as set forth in Table 7 (SEQ ID NOS:73-146), Table 8 (SEQ ID NOS: 147-159), Table 9 (SEQ ID NOS:167, 168, 173, 200, 202, 207, and 217-219), or Table 10 (SEQ ID NOS: 160-213) are used with the compositions and methods disclosed herein.

In one aspect, the present disclosure provides an isolated D-peptide that is capable of interacting with the N-trimer groove of RSV F protein. In one embodiment, the D-peptide is capable of inhibiting RSV entry into a host cell. In another embodiment, the D-peptide is capable of interacting with the N-trimer groove of RSV-A and RSV-B subtypes. In yet another embodiment, the D-peptide is capable of inhibiting entry of RSV-A and RSV-B into a host cell.

The isolated D-peptide may be a monomer. In other embodiments, the isolated D-peptide is linked to a second D-peptide, for example an identical D-peptide to form a homodimer. In yet other embodiments, the isolated D-peptide is linked to a second and a third D-peptide (for example, two D-peptides that are identical to the first D-peptide) to form a homotrimer.

In another embodiment, an isolated D-peptide according to any of the aforementioned embodiments comprises a consensus sequence of LPXPXWW (SEQ ID NO:41), wherein X is any amino acid except cysteine; a consensus sequence of LPXPXWW (SEQ ID NO:1) or XXXXLPXPXWW (SEQ ID NO:65), wherein X is any amino acid; a consensus sequence of (R/E)X(H/E/Y)WLLDW (SEQ ID NO:2) or XXCXN(R/E/G/K)X(H/E/Y/D/Q)WLLDWCXX (SEQ ID NO:66), wherein X is any amino acid except cysteine; or a consensus sequence as in XXCXXTGYFXWCXX (SEQ ID NO:160), XHCXXHWXXDWCXX (SEQ ID NO:161), XXCXXTGYFXWCXX (SEQ ID NO:162), ALXKKDXE(D/E)LKKFXEWXG (SEQ ID NO:163), AHXKIXXEXWKKXXEHXG (SEQ ID NO:164), AWDKKXXEXXKKFXEXXG (SEQ ID NO:165), or XXCDWSHYXGCXX (SEQ ID NO:166), wherein X is any amino acid. In a further embodiment, a D-peptide comprises an amino acid sequence as set forth in any one of the sequences in Table 2 (SEQ ID NOS:3-31). In yet a further embodiment, a D-peptide comprises an amino acid sequence as set forth in any one of the sequences in Table 7 (SEQ ID NOS:73-146). In another embodiment, a D-peptide consists of any one of the sequences in Table 7. In a specific embodiment, a D-peptide comprises an amino acid sequence of RSVP7 (SEQ ID NO:16), RSVP11 (SEQ ID NO:17), RSVP24 (SEQ ID NO:23), RSVP25 (SEQ ID NO:24), RSVP26 (SEQ ID NO:25), RSVP27 (SEQ ID NO:26), RSVP28, (SEQ ID NO:27) RSVP29 (SEQ ID NO:28), RSVP30 (SEQ ID NO:29), RSVP31 (SEQ ID NO:30), or RSVP32 (SEQ ID NO:31). In a further embodiment, a D-peptide comprises an amino acid sequence as set forth in any one of the sequences in Table 8 (SEQ ID NOS:147-159). In a further embodiment, a D-peptide comprises an amino acid sequence as set forth in any one of the sequences in Table 9 (SEQ ID NOS:167, 168, 173, 200, 202, 207, and 217-219). In a further embodiment, a D-peptide comprises an amino acid sequence as set forth in any one of the sequences in Table 10 (SEQ ID NOS:167-213). In any of the aforementioned embodiments, the D-peptide may have an N-terminus capped with an acetyl group and a C-terminus capped with an amide group. Additionally, in any of the aforementioned embodiments, the D-peptide may have an N-terminus capped with an acetyl group and a C-terminus capped with an amide group, and the D-peptide may be linked to other D-peptides to form a trimer.

In certain embodiments, the N-terminus of the D-peptide is capped with an acetyl group. Having the N-terminus of the D-peptide capped with an acetyl group may be preferred in the context of a D-peptide trimer where a single unique amine is to be provided by a lysine residue for attachment of the D-peptide to a scaffold.

In certain embodiments, the C-terminus of the D-peptide is capped with an amide group.

In certain embodiments, the D-peptide has an N-terminus capped with an acetyl group and a C-terminus capped with an amide group. In particular embodiments, a D-peptide has an N-terminus capped with an acetyl group and a C-terminus capped with an amide group, and the D-peptide is linked to other D-peptides via a scaffold to form a trimer.

In certain embodiments, the D-peptide is linked to a potency enhancing cargo molecule. A potency enhancing cargo molecule may be cholesterol, sterol, sugar, maltose binding protein, ubiquitin, streptavidin, immunoglobulin domain, keyhole limpet hemacyanin, sperm whale myooovalbumin, bovine pancreatic trypsin inhibitor, green fluorescent protein, gold particle, magnetic particle, agarose bead, lactose bead, fatty acid, a high molecular weight PEG, or serum albumin. The potency enhancing cargo molecule may be linked to the D-peptide with a PEG linker (e.g., $PEG_{12}$, $PEG_{16}$, $PEG_{24}$, $PEG_{25}$, $PEG_{26}$, $PEG_{27}$, $PEG_{28}$, $PEG_{29}$, $PEG_{30}$, $PEG_{31}$, $PEG_{32}$, $PEG_{33}$, $PEG_{34}$, $PEG_{35}$, or $PEG_{36}$). Potency enhancement of D-peptide trimers using cargo molecules has been described in U.S. Patent Publication 2014/0323392 and Francis et al., 2012, Bioconjug. Chem. 23:1252-8 (each of which is incorporated by reference in its entirety).

TABLE 1

RSV D-Peptide Inhibitor Consensus Sequences

| Library Name | Consensus Sequence | SEQ ID NO: |
|---|---|---|
| X16 | LPXPXWW | 41 |
| X12 | LPXPXWW | 1 |
| CX10C | (R/E)X(H/E/Y)WLLDW | 2 |

"X" in the X12 naive library represents all 20 natural amino acids.
"X" in the X16 and CX10C naive libraries represents all 20 natural amino acids except Cys.

TABLE 2

Amino acid sequences of RSV D-peptide inhibitors (RSVPs)

| D-peptide Name | Sequence | SEQ ID NO: |
|---|---|---|
| X16-16 | DYLPLPEPRWWFPEYQ | 3 |
| X16-18 | SLKYWWMEELPLPKWW | 4 |
| X16-20 | HWLPLQPWWDDIPVWH | 5 |
| G12 | KVWTIQKPLTLY | 6 |
| H11 | TMHHKVWLIPKA | 7 |
| X12-31 | ALTYTLPVPHWW | 8 |
| X12-45 | ISLPTPTWWPST | 9 |
| X12-47 | SKVILPEPFWWP | 10 |
| RSVP1 | RWFELPEPDWW | 11 |
| RSVP3 | SWFYLPEPDWW | 12 |
| RSVP4 | KYFWLPEPDWW | 13 |
| RSVP5 | EWFYLPEPRWW | 14 |
| RSVP6 | QWYFLPEPNWW | 15 |
| RSVP7 | RWFELPEPEWW | 16 |
| RSVP11 | VDHRWQRWFELPDPEWW | 17 |
| CXC10C-86 | GACHTWDLNHLDVCAA | 18 |
| CXC10C-119 | GACKIHDLFHWHDCAA | 19 |
| RSVP20 | GACRNEPHWLLDWCAA | 20 |
| RSVP21 | GACTNRAEWLIDWCAA | 21 |
| RSVP22 | GACKQRTEWYFDWCAA | 22 |
| RSVP24 | SMCVNRPEWLLDWCGT | 23 |
| RSVP25 | EDCVNRSYWLLDWCNI | 24 |
| RSVP26 | HACVNRPEWLLDWCGR | 25 |
| RSVP27 | HECVNRPEWLLDWCEH | 26 |
| RSVP28 | HACVNRPEWLLDWCDH | 27 |
| RSVP29 | SACVNRPEWLLDWCGT | 28 |
| RSVP30 | SSCVNRPEWLLDWCGT | 29 |
| RSVP31 | AECVNRPEWLLDWCGT | 30 |
| RSVP32 | GECVNRPEWLLDWCGT | 31 |

Because of library design for the CX10C circular library, peptides derived therefrom, in addition to the amino acid residues shown, may be flanked by GA on the N-terminus and AA on the C-terminus. N-terminal lysine residues may also be added to improve water solubility.

In some embodiments, the peptides, portions of the peptides, variations/derivatives of the peptides, or portions of the variations/derivatives described are used as inhibitors of RSV entry into host cells. In some embodiments, the peptides disclosed herein, or a portion of a peptide sufficient to bind to the N-trimer groove of the coiled-coil and prevent interaction of the C-peptide region with the N-peptide region of F protein, are useful to inhibit RSV infection. A portion of any of the peptides represented or of a derivative thereof can be from 2 to 8 (any number of residues from 2 to 8) amino acid residues in size. In particular embodiments, D-peptides which comprise the consensus sequence LPXPXWW (SEQ ID NO: 1) or the sequence (R/E)X(H/E/Y)WLLDW (SEQ ID NO: 2), described herein, and additional residues, can be used. In still other particular embodiments, D-peptides which comprise the consensus sequence XXXX-LPXPXWW (SEQ ID NO: 65) or the sequence XXCXN(R/E/G/K)X(H/E/Y/D/Q)WLLDWCXX (SEQ ID NO: 66), described herein, and additional residues, can be used. The other residues present in such D-peptides and the size of the D-peptides can be selected with reference to peptides described herein or can be designed independent of those peptides, provided that these other residues are positioned in such a manner that the peptide can fit into the hydrophobic pocket and act as an inhibitor. Additional amino acid residues can also be present at the N-terminus, the C-terminus or both of the D-peptides described herein, thus producing a larger peptide. Alternatively, there can be other amino acid residues selected, for example, to enhance binding affinity. Alternatively, a peptide which comprises the conserved amino acid residues of the D-peptides disclosed herein can be used. For example, such a peptide can include the conserved amino acid residues, which can be at the same positions as those at which they occur in the peptides disclosed herein.

In some embodiments, the intervening amino acid residues (between conserved amino acid residues) can be different from the amino acid residues at these positions in any of the peptides disclosed herein or can be substituted for or replaced by an amino acid residue represented at a specific position in another peptide. Amino acid residues other than the D-versions of the 20 L-amino acids found in natural proteins can be used. Such changes can be made, for example, to enhance bioavailability, binding affinity, or other characteristic of the peptide. A D-peptide can comprise the conserved amino acid residues present in the peptides disclosed herein, but they can be separated by fewer (or more) amino acid residues than the number of intervening amino acid residues shown in Table 2. For example, a D-peptide may comprise the consensus sequence of SEQ ID NO:2 and have fewer than ten amino acid residues present between the first cysteine and second cysteine residues. Alternatively, a D-peptide may comprise the consensus sequence of SEQ ID NO:2 and the two cysteine residues may be separated by more than ten amino acid residues. Internal modifications can also be made (e.g., to enhance binding or increase solubility of a peptide). For example, an amino acid may be substituted to increase solubility. A D-peptide can have additional moieties or amino acids at its N-terminus. For example, a moiety which blocks the N terminus or gets rid of the charge otherwise present at the N-terminus can be added. The moiety can be, for example, a blocking moiety, such as an acetyl group linked directly to the N-terminal amino acid residue. In one embodiment, one or two lysine residues are linked to the N-terminal amino acid residue, for example to increase the solubility of the peptide; a blocking moiety, such as an acetyl group, can be linked to the terminal amino acid residue. In another embodiment, four lysine residues are linked to the N-terminal amino acid residue. In addition, a D-peptide can have additional and/or altered moieties or amino acids at its C-terminus. For example, one or both of the residues at the C-terminus can be altered and/or one or more residues can be added at the C-terminus, for example to enhance binding. Alternatively, functional (chemical) groups other than amino acid residues can be included to produce an inhibitor of the present invention. For example, these additional chemical groups can be present at the N-terminus, the C-terminus, both termini, or internally. In other embodiments one or two aspartic acid or glutamic acid residues are added to the N- or C-terminus.

Two or more D-peptides can be linked via an appropriate linker (e.g., a linker of amino acid residues or other chemical moieties) to increase the effectiveness of inhibition. Alternatively, one or more D-peptides can be linked via an appropriate linker to a molecule (drug) that binds to RSV G protein, HSP90, L protein, N protein, P protein, M2-1 protein, or a non-groove region of RSV F protein to increase the effectiveness of inhibition.

Regarding the nomenclature of the peptides disclosed herein, different families of peptides are referred to as x-mers, where x is considered the number of residues between the cysteine residues. The x-mers are referred to as the "core peptides." For example, SEQ ID NO: 31 (GECVNRPEWLLDWCGT) is comprised of 16 residues, and so in the standard art would be referred to as a 16-mer. However, in the context of peptides derived from CX10C library screening, the length of residues between the cysteines (C) is 10, so it would be considered an 10-mer (and referred to as having 10 core residues), and referred to as such throughout the application. Amino acids outside of the two Cys residues are referred to as "flanking" sequences. This naming scheme allows different families of peptides that differ in the number of residues between the two Cys residues, but can vary in total peptide length due to differences in their flanking sequences, to be distinguished. For example, SEQ ID NO: 30 (AECVNRPEWLLDWCGT) has a length of 16 residues, is a member of the 10-mer peptide family (as it has 8 core residues), and has an N-terminal flanking sequence of AE and a C-terminal flanking sequence of GT.

As described above, the D-peptides derived from the CX10C library can be flanked by GA at the N-terminus and AA at the C-terminus, due to the design of the library used in identifying the D-peptides. Some or all of these four amino acid residues may be altered, replaced or deleted in order to produce D-peptides with, for example, altered absorption, distribution, metabolism, or excretion. In one embodiment, the C-terminus is modified by the addition of a glycine residue immediately before the C-terminal amide. In another embodiment, the most C-terminal A is altered/modified or replaced by a different amino acid residue or deleted.

D-peptides, which are of the opposite handedness from the handedness of naturally-occurring peptides, do not serve as efficient substrates for enzymes, such as proteases, and, therefore, are not as readily degraded as L-peptides. In addition, there is no effective immune response which targets D-peptides and therefore, they do not elicit an immune response comparable to that elicited by L amino acid peptides.

The peptides disclosed herein can also be present at multimers, such as dimers or trimers. Such multimers are discussed in more detail below. When the multimer is a dimer, the dimer can be comprised of two identical peptides (homodimer), or can be comprised of two different peptides (heterodimer). The multimer can also be a trimer. When the multimer is a trimer, the trimer can be comprised of two identical peptides and one different peptide (heterotrimer), or three identical peptides, (homotrimer) or three different peptides (heterotrimer), each of which are distinct from each other. The D-peptides disclosed herein can also be present as pharmaceutical compositions comprising a pharmaceutically acceptable carrier. This is discussed in more detail below.

In another embodiment, an isolated D-peptide comprises a consensus sequence of LPXPXWW (SEQ ID NO:41), wherein X is any amino acid except cysteine; a consensus sequence of LPXPXWW (SEQ ID NO:1) or XXXXLPXPXWW (SEQ ID NO:65), wherein X is any amino acid; a consensus sequence of (R/E)X(H/E/Y)WLLDW (SEQ ID NO:2) or XXCXN(R/E/G/K)X(H/E/Y/D/Q)WLLDWCXX (SEQ ID NO:66), wherein X is any amino acid except cysteine; a consensus sequence of XXCXXTGYFXWCXX (SEQ ID NO:160), XHCXXHWXXDWCXX (SEQ ID NO:161), XXCXXTGYFXWCXX (SEQ ID NO:162), ALXKKDXE(D/E)LKKFXEWXG (SEQ ID NO:163), AHXKIXXEXWKKXXEHXG (SEQ ID NO:164), AWDKKXXEXXKKFXEXXG (SEQ ID NO:165), or XXCDWSHYXGCXX (SEQ ID NO:166), wherein X is any amino acid; an amino acid sequence as set forth in any one of the sequences in Table 2 (SEQ ID NOS:3-31); an amino acid sequence as set forth in any one of the sequences in Table 7 (SEQ ID NOS:73-146); an amino acid sequence of RSVP7 (SEQ ID NO:16), RSVP11 (SEQ ID NO:17), RSVP24 (SEQ ID NO:23), RSVP25 (SEQ ID NO:24), RSVP26 (SEQ ID NO:25), RSVP27 (SEQ ID NO:26), RSVP28, (SEQ ID NO:27) RSVP29 (SEQ ID NO:28), RSVP30 (SEQ ID NO:29), RSVP31 (SEQ ID NO:30), or RSVP32 (SEQ ID NO:31); an amino acid sequence as set forth in any one of the sequences in Table 8 (SEQ ID NOS:147-159); an amino acid sequence as set forth in any one of the sequences in Table 9 (SEQ ID NOS:167, 168, 173, 200, 202, 207, and 217-219); or an amino acid sequence as set forth in any one of the sequences in Table 10 (SEQ ID NOS:167-213). In any of the aforementioned embodiments, the D-peptide may have an N-terminus capped with an acetyl group and a C-terminus capped with an amide group. Additionally, in any of the aforementioned embodiments, the D-peptide may have an N-terminus capped with an acetyl group and a C-terminus capped with an amide group, and the D-peptide may be linked to other D-peptides to form a trimer.

In one embodiment, a D-peptide comprises an amino acid sequence as set forth in SEQ ID NO: 31. In yet another embodiment, a D-peptide comprises an amino acid sequence as set forth in SEQ ID NO: 31, and the N-terminus is capped with an acetyl group and the C-terminus is capped with an amide group. In a further embodiment, a D-peptide comprises the amino acid sequence Ac-K(PEG4)-DDG-GECVNRPEWLLDWCGT-NH2 (SEQ ID NO:142). In still another embodiment, a D-peptide comprises an amino acid sequence as set forth in any one of SEQ ID NOS: 147-159. In any of the aforementioned embodiments, the D-peptide may be present as a monomer or a multimer, such as a dimer or trimer. Furthermore, in any of the aforementioned embodiments, the peptides, portions of the peptides, variations/derivatives of the peptides, or portions of the variations/derivatives may be used as inhibitors of RSV entry into host cells. Additionally, in any of the aforementioned embodiments, the peptide, or a portion of the peptide sufficient to bind to the N-trimer groove of the coiled-coil and prevent interaction of the C-peptide region with the N-peptide region of F protein, may be used to inhibit RSV infection.

Multimers

The present disclosure also provides multimers of the D-peptides which are disclosed herein. A multimer can comprise at least one D-peptide which interacts with the N-trimer groove of a RSV F protein. A multimer can be a dimer, trimer, or higher order multiples. Multimers may be cross-linked by methods known to those of skill in the art. An example of a cross-linker is polyethylene glycol (PEG) derivatized with NETS-ester (reacts with Lys) or maleimide (reacts with Cys). Cross-linkers can also contain two distinct linkage chemistries (e.g., NETS-ester on one end and maleimide on the other end). D-peptides may also be linked by direct disulfide bond formation between two Cys residues.

The D-peptides that are linked can be any of those disclosed herein, and the D-peptides can be identical to each other or can each be different. When a dimer is present, the N-termini of both of the peptides can be cross-linked to each other. Alternatively, the C-termini of the peptides can be cross-linked. In yet another embodiment, the N-terminus of one peptide and the C-terminus of the other peptide are cross-linked. When a trimer is present, the N-termini and C-termini of the three peptides can be linked in any combination. For example, they can be linked in any of the following arrangements:

N—N/C—C—peptide 1's N-terminus links to peptide 2's N-terminus; peptide 2's C-terminus links to peptide 3's C-terminus. Using this naming, there are 16 possible trimer linages:

X/Y where

X and Y=N—N, N—C, C—N, or C—C

The naming scheme for multimers indicates which PEG spacer is used to connect the monomers. For example, Ac-K(PEG6)-RSVP21-trimer comprises three D-peptides monomers, wherein each RSVP21 D-peptide comprises an N-terminal lysine that is capped with an acetyl group. In this embodiment, a PEG6 spacer is incorporated into the peptide backbone between the N-terminal lysine and the rest of the monomer sequence; the monomers are connected by reacting the unique primary amine with a scaffold containing NHS or PFP ester. Further examples of D-peptide multimers and binding affinity and inhibitory data are described in Table 7. For example, Ac-KG-RSVP20 (SEQ ID NO:123) does not contain a PEG spacer in the peptide backbone but can be crosslinked to a PEG spacer. The resulting peptide with spacer could be further crosslinked to form a dimer or trimer using a scaffold. Note: The zero length spacers can be any of a variety of short cross-linkers (e.g., BS3, DSG, or DST). The structure of DSG is as follows:

DSG
(Disuccinimidyl Glutarate)
MW 326.26
Spacer Arm Length 7.72Å

In certain embodiments, cross-linking of the N-termini is preferred for making multimers.

The multimers disclosed herein can be made of any combination of peptides, including those disclosed above (e.g., peptides shown in Table 1, 2, 5, 7, 8, 9, or 10) or variants thereof. In some embodiments, the multimers can be made up of one of the peptides disclosed herein, two of the peptides disclosed herein, or three or more of the peptides disclosed herein. All of the peptides can be identical, or they can be any combination of peptides, including those disclosed and those which are not specifically disclosed. In one embodiment, at least one of the peptides in a multimer as disclosed herein comprises the sequence of SEQ ID NO:1, SEQ ID NO:2, SEQ ID NO:41, SEQ ID NO:65, SEQ ID NO:66, or any one of SEQ ID NOS:160-166, as discussed above. In some embodiments, the multimer can inhibit RSV entry into a cell. The multimer can be made up of at least one D-peptide, and can comprise all D-peptides, or other components as well.

In some embodiments, a 'Tricasso' strategy is used for producing diverse multimeric peptides using an automated peptide synthesizer during solid-phase peptide synthesis (SPPS). The Tricasso method may offer several advantages compared to traditional chemical cross-linking. For example, the Tricasso method can be used to rapidly explore multimer geometry, including optimal spacing between monomers, by automating production of the oligomer and eliminating the need for intermediate purification of monomers before cross-linking. The Tricasso method also allows multimers to be produced in the absence of unique chemical functionality that traditionally enables specificity of chemical cross-linking. For example, amine coupling to a specific site cannot traditionally be accomplished in instances when the peptide sequence contains one or more lysine residues plus a free (unblocked) N-terminus. In contrast, production of Tricasso oligomers with a specific defined geometry is independent of the peptide sequence. Another advantage of the Tricasso method is that it does not require high solubility. Traditional cross-linking often requires high solubility since performing cross-linking reactions at high concentration is commonly used to drive the efficiency of the reaction. Furthermore, intermediates can have limited solubility despite good solubility of the final product (e.g., the cross-linker itself can aid solubility of a peptide). Because Tricasso multimers avoid the need for cross-linking reactions, high solubility is not required for their production.

To produce a Tricasso multimer, a peptide 'hub' incorporating specially protected lysine residues (e.g., Fmoc-Lys (Dde)), at desired positions is synthesized. The number of protected lysine residues should match the order of the multimer (e.g., a hub with three lysines should be synthesized to make a trimer). The spacing between peptides can be fine-tuned by altering the hub (e.g., by introducing variable numbers of glycine or flexible PEG units between the lysines). In this approach, the N-term of the hub should be capped (e.g., with an acetyl group). Once the hub is synthesized and capped at the N-terminus, the protected lysine residues are deprotected (e.g., by incubation with hydrazine to cleave Dde) revealing free primary amines at each lysine sidechain. Subsequently, identical peptides are simultaneously "grown" onto each lysine sidechain, as shown below.

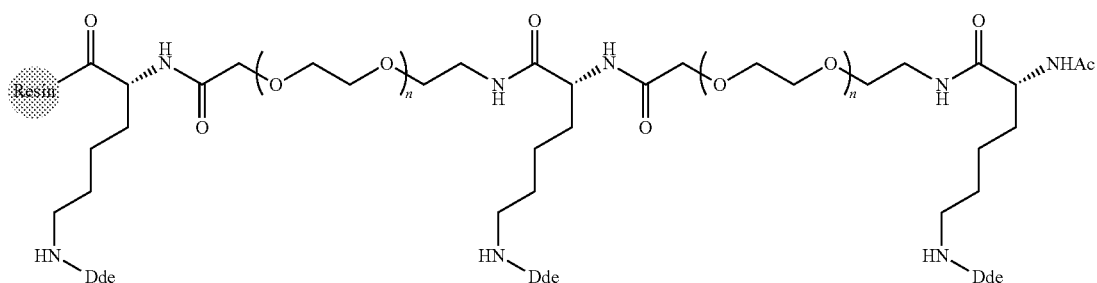

↓ 1. Cleave Dde groups
2. Grow D-Peptides
3. Cleave resin

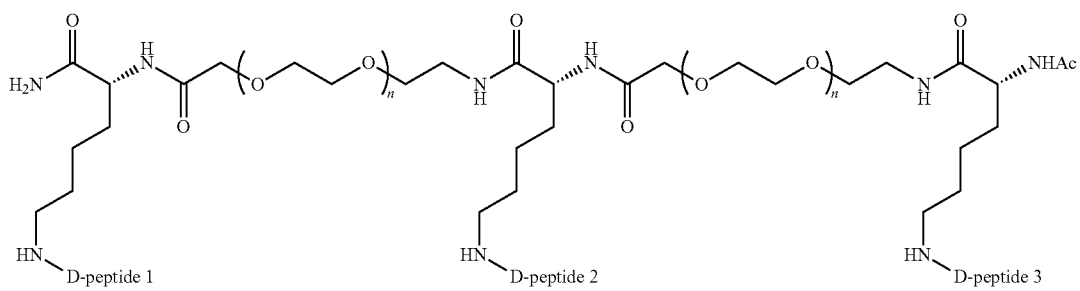

In the above figure, D-peptides are shown. However, in another embodiment, the same method is used to multimerize L-peptides.

Alternately, the N-terminus of the peptide hub could be left uncapped. In this instance, the number of specially protected lysine residues in the hub should be one less than the order of the multimer (e.g., two protected lysines for a trimer). After deprotection of the lysines identical peptides are simultaneously grown onto each lysine sidechain as well as the N-terminus of the peptide hub, to provide the following structure (I):

I

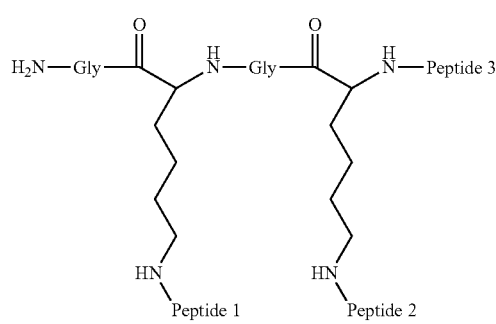

Either Tricasso strategy described (capped or free N-terminus) may be used to produce L- or D-peptide multimers.

In one embodiment, each peptide monomer is connected to a Tricasso hub at its C-terminus.

In one embodiment, a 'hub' used to produce a Tricasso multimer (e.g., a compound of formula I) comprises a peptide or polymer comprising one or more protected lysine residues.

As an alternate strategy for making multimers, such as trimers, a central scaffold (such as TSAT, which contains three NHS ester groups) can be used to attach three or more D-peptides. This geometry is referred to as 'the claw', since it looks like an eagle claw. Two examples of this strategy are (1) a short claw (which directly links TSAT to the peptides) and (2) a long claw (which uses an extended form of TSAT (LC-TSAT) that contains an additional six-atom spacer between TSAT and the peptides). Other spacer lengths or compositions (e.g., PEG) can also be used.

Below is a representation of LC-TSAT:
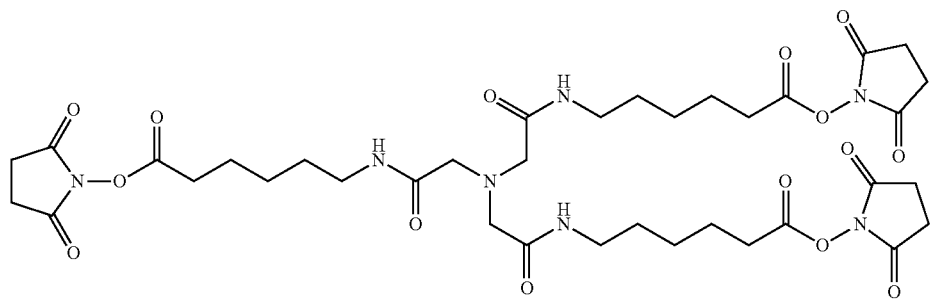 [SMILES: O=C(CN(CC(=O)NCCCCCC(=O)ON1C(=O)CCC1=O)CC(=O)NCCCCCC(=O)ON1C(=O)CCC1=O)NCCCCCC(=O)ON1C(=O)CCC1=O]
And the following is a representation of TSAT:
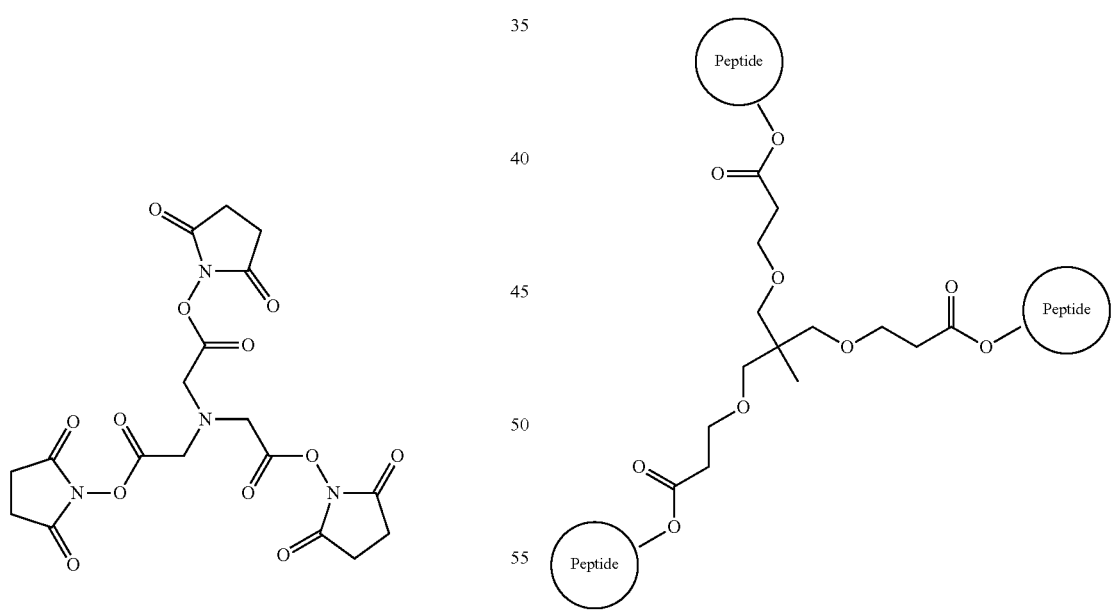
II
In another embodiment, a multimer comprises three peptides connected via a scaffold as in the following structure (II):
In a further embodiment, a multimer comprises three peptides connected via a scaffold as in the following structure (III):

In still a further embodiment, a multimer comprises three peptides connected via a scaffold as in the following structure (IV):

Such inhibitors do not show improved potency, but have a reserve of binding energy that acts as a 'resistance capacitor' to defend against potential resistance mutations (i.e., resistance mutations that moderately affect binding would have no effect on potency). Of particular importance, this property discourages the stepwise accumulation of multiple subtle mutations that combine to confer resistance. Individual mutations may have no effect on inhibitor potency and may not confer a growth advantage in the presence of inhibitors. This resistance capacitor may be especially beneficial for trimeric inhibitors, because resistance mutations simultaneously affect all three pockets. As a further defense against the development of resistance, in some embodiments, the trimeric D-peptides disclosed herein can also be constructed by using three different D-peptide sequences, each with a distinct resistance profile. Such a heterotrimer would present a significant additional barrier to the development of resistance (see, Welch et al. Proc Natl Acad Sci USA. 2007 Oct. 23; 104(43):16828-33).

In some embodiments disclosed herein, a multimer has improved binding affinity compared to the corresponding monomer. For example, as disclosed in Example 4 and Table 7, the trimeric inhibitor RSVP20 has $K_g$'s of 0.3 nM as compared to 3.7 µM. This value represents a dramatic 10,000-fold improvement over the corresponding monomer. These data also indicate that modest improvements in the potency of monomeric inhibitors are magnified by avidity in the trimer, as also observed in the phage display.

In some embodiments, the multimer can exhibit about a 1-fold, 2-fold, 3-fold, 4-fold, 5-fold, 10-fold, 20-fold, 25-fold, 30-fold, 40-fold, 50-fold, 100-fold, 200-fold, 300-fold, 400-fold, 500-fold, 1000-fold, 2000-fold, 3000-fold, 4000-fold, 5000-fold, or 10,000-fold increase in affinity for the N-trimer when compared with the affinity of one of the components of the multimer alone (e.g., one of the peptides as a monomer).

The multimers disclosed herein can have any of the characteristics or properties that are disclosed above. Any of the multimers disclosed herein may be capable of having avidity as described herein, and any of them can be used with the methods disclosed herein for increasing inhibition of viral entry.

In some embodiments, over-engineering future D-peptides improves affinity even after reaching the potency limit.

In one embodiment, a D-peptide as described herein is multimerized using any of the cross-linking, Tricasso, or scaffold structures described herein. For example, in one embodiment, a composition comprises a multimer, wherein the multimer comprises two or more D-peptides each comprising a consensus sequence of LPXPXWW (SEQ ID NO:41), wherein X is any amino acid except cysteine; a consensus sequence of LPXPXWW (SEQ ID NO:1) or XXXXLPXPXWW (SEQ ID NO:65), wherein X is any amino acid; a consensus sequence of (R/E)X(H/E/Y)WLLDW (SEQ ID NO:2) or XXCXN(R/E/G/K)X(H/E/Y/D/Q)WLLDWCXX (SEQ ID NO:66), wherein X is any amino acid except cysteine; a consensus sequence as in XXCXXTGYFXWCXX (SEQ ID NO:160), XHCXXH-WXXDWCXX (SEQ ID NO:161), XXCXXTGYFXWCXX (SEQ ID NO:162), ALXKKDXE(D/E)LKKFXEWXG (SEQ ID NO:163), AHXKIXXEXWKKXXEHXG (SEQ ID NO:164), AWDKKXXEXXKKFXEXXG (SEQ ID NO:165), or XXCDWSHYXGCXX (SEQ ID NO:166), wherein X is any amino acid; an amino acid sequence as set forth in any one of the sequences in Table 2 (SEQ ID NOS:3-31); an amino acid sequence as set forth in any one of the sequences in Table 7 (SEQ ID NOS:73-146); an amino acid sequence of RSVP7 (SEQ ID NO:16), RSVP11 (SEQ ID NO:17), RSVP24 (SEQ ID NO:23), RSVP25 (SEQ ID NO:24), RSVP26 (SEQ ID NO:25), RSVP27 (SEQ ID NO:26), RSVP28, (SEQ ID NO:27) RSVP29 (SEQ ID NO:28), RSVP30 (SEQ ID NO:29), RSVP31 (SEQ ID NO:30), or RSVP32 (SEQ ID NO:31); an amino acid sequence as set forth in any one of the sequences in Table 8 (SEQ ID NOS:147-159); an amino acid sequence as set forth in any one of the sequences in Table 9 (SEQ ID NOS:167, 168, 173, 200, 202, 207, and 217-219); or an amino acid sequence as set forth in any one of the sequences in Table 10 (SEQ ID NOS:167-213); and the two or more D-peptides are linked by a structure of formula I, II, III, or IV. In any of the aforementioned embodiments, the D-peptide may have an N-terminus capped with an acetyl group and a C-terminus capped with an amide group.

In one embodiment, the present disclosure provides an isolated composition comprising a multimer having the structure of formula IV, wherein each "peptide" is a D-peptide comprising an amino acid sequence as set forth in SEQ ID NO: 31, wherein the N-terminus of the D-peptide is capped with an acetyl group and the C-terminus of the D-peptide is capped with an amide group.

In one embodiment, the present disclosure provides an isolated composition comprising a multimer having the structure of formula IV, wherein each "peptide" is a D-peptide comprising the amino acid sequence Ac-K(PEG4)-DDG-GECVNRPEWLLDWCGT-NH2 (SEQ ID NO:142). In another embodiment the amino acid sequence is Ac-K (PEG4)-EEG-GECVNRPEWLLDWCGT-NH2 (SEQ ID NO:214).

In a further embodiment, the present disclosure provides an isolated composition comprising a multimer having the structure of formula IV, wherein each "peptide" is a D-peptide comprising a consensus amino acid sequence as recited in SEQ ID NO:2 or SEQ ID NO:66.

Peptide Variants

As discussed herein there are numerous variants of the peptides disclosed herein that are herein contemplated. Peptide variants and derivatives are well understood to those of skill in the art and in can involve amino acid sequence modifications. Those peptides disclosed herein that can be used to inhibit viral entry can comprise such amino acid sequence modifications. One of skill in the art would be able to readily determine which modifications can be made in order to retain the activity of the peptide.

Analogs of the peptides disclosed herein are also contemplated. These analogs include one or more D-amino acids of the peptidic structure which are substituted with a homologous amino acid such that the properties of the original peptide are maintained. Preferably conservative amino acid substitutions are made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Non-limiting examples of homologous substitutions that can be made in the peptidic structures of the peptides disclosed herein include substitution of D-phenylalanine with D-tyrosine, D-pyridylalanine, or D-homophenylalanine; substitution of D-leucine with D-valine, other natural amino acid, or non-natural amino acid having an aliphatic side chain; or substitution of D-valine with D-leucine, other natural amino acid, or non-natural amino acid having an aliphatic side chain. This is given as an example and is not intended to be limiting. One of skill in the art would be capable of making conservative substitutions to a D-peptide.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

The opposite stereo-isomers of naturally occurring peptides are disclosed, as well as the stereo-isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include —$CH_2NH$—, —$CH_2S$—, —$CH_2$—$CH_2$—, —CH=CH— (cis and trans), —$COCH_2$—, —$CH(OH)CH_2$—, and —$CHH2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int. J. Pept. Prot. Res. 14:177-185 (1979) (—CH2NH—, CH2CH2—); Spatola et al. Life Sci 38:1243-1249 (1986) (—CHH2-S); Hann J. Chem. Soc. Perkin Trans. 1307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH) $CH_2$—); Holladay et al. Tetrahedron. Lett 24:4401-4404 (1983) (—C(OH)$CH_2$—); and Hruby Life Sci. 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as β-alanine, γ-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by proteases and peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

The present disclosure also provides an isolated composition comprising any of the embodiments of D-peptides and multimers disclosed herein.

Pharmaceutical Compositions and Delivery Thereof

In other aspects, the present disclosure provides D-peptides and multimers (alternatively referred to as 'compositions') that can be administered in vivo in a pharmaceutically acceptable carrier. By "pharmaceutically acceptable" is meant a material that is not biologically or otherwise undesirable, i.e., the material may be administered to a subject, along with the peptide disclosed herein, without causing significant undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by subcutaneous injection, by intraperitoneal injection, transdermally, extracorporeally, topically, or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight, and general condition of the subject, the severity of the disease, its mode of administration, and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The compositions, including peptides and multimers thereof, can be used therapeutically in combination with a pharmaceutically acceptable carrier.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, saline, Ringer's solution, and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes, or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents, and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal, or intramuscular injection. The disclosed peptides and multimers thereof can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases, and the like.

Formulations for topical administration may include ointments, lotions, creams, gels, drops, suppositories, sprays, liquids, and powders. Conventional pharmaceutical carriers, aqueous, powder or oily bases, thickeners, and the like may be necessary or desirable.

Compositions for oral administration include powders or granules, suspensions or solutions in water or non-aqueous media, capsules, sachets, or tablets. Thickenings, flavorings, diluents, emulsifiers, dispersing aids, or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Therapeutic Uses

In another aspect, the instant disclosure provides D-peptides and multimers thereof for use treating a disease or disorder. Effective dosages and schedules for administering the compositions such as peptides and multimers thereof may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex, and extent of the disease in the patient, route of administration, or whether other drugs are included in the regimen, and can be determined by one of skill in the art. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products, particularly for D-peptides. Examples of such guidance can be found throughout the literature. In one embodiment, the typical daily dosage of the peptides or multimers thereof used alone might range from about 1 µg/kg to up to 100 mg/kg of body weight or more per day, depending on the factors mentioned above. Furthermore, the peptides disclosed herein can be administered several times daily, daily, weekly, monthly, or yearly, depending on the condition of the subject, other modes of therapy, etc. One of skill in the art could readily ascertain an appropriate dosing schedule.

Following administration of a disclosed composition, such as a peptide or multimer, for treating, inhibiting, or preventing a viral infection, such as RSV, the efficacy of the peptide or multimer thereof can be assessed in various ways well known to the skilled practitioner. For instance, one of ordinary skill in the art will understand that a composition, such as a D-peptide, disclosed herein is efficacious in treating or inhibiting a RSV infection in a subject by observing that the composition inhibits RSV entry. Efficacy of the administration of the disclosed composition may also be determined by measuring the number of uninfected cells in the infected subject. A treatment that inhibits an initial or further decrease in uninfected cells in a subject or patient, or that results in an increase in the number of uninfected cells in, for example, the RSV-positive subject, is an efficacious treatment. The efficacy can also be evaluated using indirect measures of infection, such as, levels of anti-RSV antibodies, and PCR to detect viral RNA levels.

The compositions that inhibit viral entry disclosed herein may be administered prophylactically to patients or subjects who are at risk for being exposed to a virus such as RSV (pre-exposure prophylaxis, PrEP) or who have been newly exposed to RSV (post-exposure prophylaxis, PEP). In subjects who have been newly exposed to a virus such as RSV but who have not yet displayed the presence of the virus (as measured by PCR or other assays for detecting the virus) in blood or other body fluid, efficacious treatment with a peptide or multimer thereof partially or completely inhibits the ability of the virus to infect cells.

The disclosed compositions and methods can also be used for example as tools to isolate and test new drug candidates for a variety of viral-related diseases.

In one embodiment, a method of treating RSV infection in a subject is provided, comprising administering a D-peptide comprising a consensus sequence as recited in SEQ ID NO:2 or SEQ ID NO:66; an amino acid sequence as set forth in SEQ ID NO: 31; or the amino acid sequence Ac-K(PEG4)-DDG-GECVNRPEWLLDWCGT-NH2 (SEQ ID NO:142). In the aforementioned embodiment, the N-terminus of the D-peptide may be capped with an acetyl group and the C-terminus of the D-peptide may be capped with an amide group. In one embodiment, the D-peptide is present in a multimer having the structure of formula IV.

In one embodiment, a method of treating RSV infection in a subject is provided, comprising administering a composition, wherein the composition comprises a multimer having the structure of formula IV, wherein each "peptide" is a D-comprising a consensus sequence as recited in SEQ ID NO:2 or SEQ ID NO:66; an amino acid sequence as set forth in SEQ ID NO: 31; the amino acid sequence of Ac-K(PEG4)-DDG-GECVNRPEWLLDWCGT-NH2 (SEQ ID NO:142); or the amino acid sequence of Ac-K(PEG4)-EEG-GECVNRPEWLLDWCGT-NH2 (SEQ ID NO:214).

Compositions Identified by Screening with Disclosed Compositions/Combinatorial Chemistry The disclosed peptides can be used as targets for any combinatorial technique to identify molecules or macromolecular molecules that interact with the disclosed compositions in a desired way. The peptides and related molecules disclosed herein can be used as targets for the combinatorial approaches. Also disclosed are the compositions that are identified through combinatorial techniques or screening techniques in which the compositions disclosed in SEQ ID NOS: 1-31, 41, Table 6, Table 7, Table 8, Table 9, or Table 10, for example, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation of F protein interactions. The molecules identified and isolated when using the disclosed compositions, such as other peptides, are also disclosed. Thus, the products produced using the combinatorial or screening approaches that involve the disclosed compositions, such as peptides, are also considered herein disclosed.

It is understood that the disclosed methods for identifying molecules that inhibit viral entry, for example, can be performed using high throughput means. The methods for screening are discussed in more detail below.

The disclosed peptides and multimers thereof can be used as targets for any molecular modeling technique to identify either the structure of the disclosed peptides or multimers or to identify potential or actual molecules, such as small molecules, which interact in a desired way with the disclosed compositions. The peptides and related molecules disclosed herein can be used as targets in any molecular modeling program or approach.

It is understood that when using the disclosed compositions in modeling techniques, molecules, such as macromolecular molecules, will be identified that have particular desired properties such as viral inhibition. The molecules identified and isolated when using the disclosed compositions, such as peptides and multimers thereof, are also disclosed. Thus, the products produced using the molecular modeling approaches that involve the disclosed compositions are also considered herein disclosed.

Generally, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 Acta Pharmaceutica Fennica 97, 159-166; Ripka, New Scientist 54-57 (Jun. 16, 1988); McKinaly and Rossmann, 1989 Annu. Rev. Pharmacol. —Toxiciol. 29, 111-122; Perry and Davies, QSAR: Quantitative Structure-Activity Relationships in Drug Design pp. 189-193 (Alan R. Liss, Inc. 1989); Lewis and Dean, 1989 Proc. R. Soc. Lond. 236, 125-140 and 141-162; and, with respect to a model enzyme for nucleic acid components, Askew, et al., 1989 J. Am. Chem. Soc. 111, 1082-1090. Other computer programs that screen and graphically depict chemicals are available from companies such as BioDesign, Inc., Pasadena, Calif., Allelix, Inc., Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include a pharmaceutical composition comprising a peptide or multimer thereof as disclosed herein. For example, disclosed is a kit for treating RSV, comprising a pharmaceutical composition comprising a peptide or multimer thereof as disclosed herein.

Compositions with Similar Functions

It is understood that the peptides disclosed herein may have certain functions, such as inhibiting viral entry. Disclosed herein are certain structural requirements for performing the disclosed functions, and it is understood that there are a variety of structures which can perform the same function that are related to the disclosed structures, and that these structures will ultimately achieve the same result, for example, inhibiting viral entry.

Methods of Making the Compositions

The compositions disclosed herein and the compositions necessary to perform the disclosed methods can be made using any method known to those of skill in the art for that particular reagent or compound unless otherwise specifically noted.

The peptides disclosed herein can be linked, for example, by disulfide cross-links. For example, the D-peptides disclosed herein have two Cys residues connected by a disulfide bond, which circularizes the peptide and creates a more compact and structured peptide. This disulfide is known to have enhanced antiviral properties. There are many alternative methods for circularizing peptides known to those of skill in the art. For example, a peptide can be circularized using lactam or other chemical bridges, PEG or other chemical cross-linkers, peptide ligation, or selenocysteine disulfides.

Two or more peptides or polypeptides can also be linked together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides, or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry N. Academic Press, New York, pp. 257-267 (1992)).

Methods of Identifying a Peptide that Interacts with the N-Trimer Groove of RSV

Also disclosed herein is a method of identifying a peptide that interacts with the N-trimer groove of RSV F protein comprising: (a) exposing at least one test peptide to an N-trimer mimic of the RSV F protein, and (b) identifying which test peptide interacts with the N-trimer mimic of the RSV F protein, wherein a test peptide that interacts with the N-trimer mimic is identified as a peptide that interacts with the N-trimer groove.

An "N-trimer mimic" (also referred to herein as target), as used herein, refers to a homotrimer of a synthetic peptide comprising at least a portion of the RSV N-trimer groove. An N-trimer mimic may comprise the entire amino acid sequence of the N-trimer groove of RSV F protein (e.g., having the N48 sequence of IZN48 molecule; see, Table 3) or a portion thereof (e.g., having the N18 sequence of IZN18 or the N21 sequence of IZN21; see Table 3). For example, an N-trimer mimic may represent a portion of the N-trimer groove comprising the N-trimer pocket (see, e.g., IZN18, IZN21). An N-trimer mimic may be composed of L-peptides, D-peptides, or a combination thereof. In certain embodiments, the N-trimer mimic is composed entirely of D-amino acids. In some embodiments, the N-trimer mimic is composed of D-amino acids except for one L-residue (e.g., lysine) on each monomer to allow proteolytic cleavage (e.g., trypsin) of the N-trimer mimic (e.g., for elution during mirror image phage display library screening). The L-residues may be positioned at the N-terminus or C-terminus of the N-trimer mimic.

In certain embodiments, the N-trimer mimic is fused to a soluble trimeric coiled-coil peptide of any protein, provided that when it is in the fusion protein with the RSV component, the RSV cavity is presented in such a manner that it is available for binding. Examples of soluble trimeric coiled-coils that may be used include that of GCN4-pIQI, GCN4-pII, Moloney Murine Leukemia Virus (Mo-MLV) or the ABC heterotrimer. IQN17 (L-form or D-form). In another embodiment, a soluble trimeric coiled-coil peptide that may be used is an isoleucine zipper (IZ). The length of the trimeric coiled-coil peptide can be modified based on the N-trimer mimic fusion partner in order to preserve the heptad repeat so that the α-helical structure, stability and trimeric state of the N-trimer mimic is maintained. The soluble trimeric coiled-coil peptide may be fused to the N-terminus or C-terminus of the N-trimer mimic.

In certain embodiments, the N-trimer mimic comprises a trimer (e.g., homotrimer) of an amino acid sequence selected from Table 3 (SEQ ID NOS:32-40) or an amino acid sequence selected from Table 4 (SEQ ID NOS:43-64).

In certain embodiments, the N-trimer mimic is exposed to a library of test peptides. In certain embodiments, the library of test peptides is a phage display library, e.g., mirror-image phage display library. Where mirror-image phage display library is used, the test peptide that is identified as interacting with the N-trimer groove may be synthesized as a D-peptide.

The methods of screening described herein may be repeated one or more times with the library of test peptides to enrich for peptides that bind to the N-trimer mimic. Selection pressure may be increased in each round of screening, for example by increasing the number and/or length of washes at each subsequent round.

A test peptide may be detectably labeled and binding of the test peptide to the N-trimer mimic is determined by detecting the presence of the detectable label on the N-trimer mimic (as a result of binding of the labeled candidate drug to the N-helix coiled-coil). Detection of the label on the helix coiled-coil groove of the N-trimer mimic is indicative of binding of the test peptide to the N-helix coiled-coil groove and demonstrates that the test peptide is a peptide which binds the N-helix coiled-coil groove.

Peptides identified using the methods described herein may be subject to further experiments, such as phage ELISA, to confirm binding of the peptide to the N-trimer target. Peptides identified by the methods described above may then be further tested for their ability to inhibit (totally or partially) RSV F protein function (membrane fusion) and, thus entry into cells, using further in vitro assays, such as the syncytium assays and/or infectivity assays described herein or others known to those of skill in the art, and/or in vivo assays in appropriate animal models or in humans.

TABLE 3

Amino acid sequences of N-trimer mimics (target)

| Target | Sequence | SEQ ID NO: |
|---|---|---|
| RSVA-IZN18 | IKKEIEAIKKEQEAIKKKIEAIEKEIEVLTSKVLD LKNYIDKQLL | 32 |
| RSVB-IZN18 | IKKEIEAIKKEQEAIKKKIEAIEKEIEVLTSKVLD LKNYINNQLL | 33 |
| RSVA-IZN21 | IKKEIEAIKKEQEAIKKKIEAIEKEIEVLTSKVLD LKNYIDKQLLPIV | 34 |
| RSVB-IZN21 | IKKEIEAIKKEQEAIKKKIEAIEKEIEVLTSKVLD LKNYINNQLLPIV | 35 |
| RSVB-IZN30 | IKKEIEAIKKEQEAIKKKIEAIEKEVVSLSNGVSV LTSKVLDLKNYINNQLLPIV | 36 |
| RSVA-IZN45 | IKKEIEAIKKEQEAIKKKIEAIEKEVNKIKSALLS TNKAVVSLSNGVSVLTSKVLDLKNYIDKQLLPIV | 37 |
| RSVB-IZN45 | IKKEIEAIKKEQEAIKKKIEAIEKEVNKIKNALLS TNKAVVSLSNGVSVLTSKVLDLKNYINNQLLPIV | 38 |
| RSVA-IZN48 | IKKEIEAIKKEQEAIKKKIEALEGEVNKIKSALLS TNKAVVSLSNGVSVLTSKVLDLKNYIDKQLLPIV | 39 |
| RSVB-IZN48 | IKKEIEAIKKEQEAIKKKIEALEGEVNKIKNALLS TNKAVVSLSNGVSVLTSKVLDLKNYINNQLLPIV | 40 |

IZ portion of the N-trimer mimic is single-underlined.
Double-underlined "K" residues are L-lysines (even when the rest of the peptide has D-amino acids) to allow trypsin cleavage of the target (e.g., elution method during phage display library screening)
Bold residues highlight sequence differences of RSV-B type from RSV-A type Methods of Inhibiting RSV Entry The D-peptides and multimers, including pharmaceutical compositions thereof, described herein may be used in methods for inhibiting entry of RSV into a host cell comprising exposing the RSV virus to the D-peptide or multimer, thereby inhibiting entry of the virus in to the host cell. Similarly, the D-peptides and multimers, including pharmaceutical compositions thereof, described herein may be used in methods of treating RSV infection in a subject, comprising administering to the subject a therapeutically effective amount of the D-peptide or multimer. A subject may be a human or non-human primate.

The methods disclosed herein can be used in conjunction with other viral therapies or antiviral agents. One of more of these antiviral agents can be used, and they can be administered before or after treatment (sequentially), or during treatment (concurrently, in the same or separate formulations) with the compositions disclosed herein. For example, in ongoing therapy, the subject can be administered the compositions comprised herein simultaneously with other treatments, meaning they can be administered about 48 hours, 24 hours, 12 hours, 8 hours, 4 hours, 2 hours, 1 hour, 30 minutes, 20 minutes, 10 minutes, 5 minutes, or one minute before treatment with the disclosed compositions. Other methods of treatment can also be administered before treatment with the compositions disclosed herein. By "before treatment" is meant that another form of treatment was given and then stopped before the current therapy was administered, or could be given immediately before, then administered again afterwards. In this case, the other methods of antiviral therapy can be administered years, months, weeks, days, hours, or minutes in advance. Other methods of treatment can also be administered after treatment with the compositions disclosed herein. By "after treatment" is meant that another form of treatment is administered after the current therapy was administered, or could be given before, then administered again afterwards. This additional antiviral treatment could be given years, months, weeks, days, hours, or minutes after the current therapy is given.

The further antiviral agent or agents can be independently selected from any one of a viral fusion inhibitor, viral attachment inhibitor, viral replication inhibitor, a viral protease inhibitor, or a viral entry inhibitor. An antiviral agent may be an inhibitor antibody, a biologic, an antisense molecule, a ribozyme, an RNA interference agent, a peptide, or a small molecule. Some examples of anti-RSV agent include Synagis® (palivizumab), and ribavirin (Virazole). Further anti-viral agents include supportive drugs, such as bronchodilators, such as albuterol and epinephrine.

EXAMPLES

Example 1

RSV N-Trimer Sequence is Highly Conserved

Figure 4:
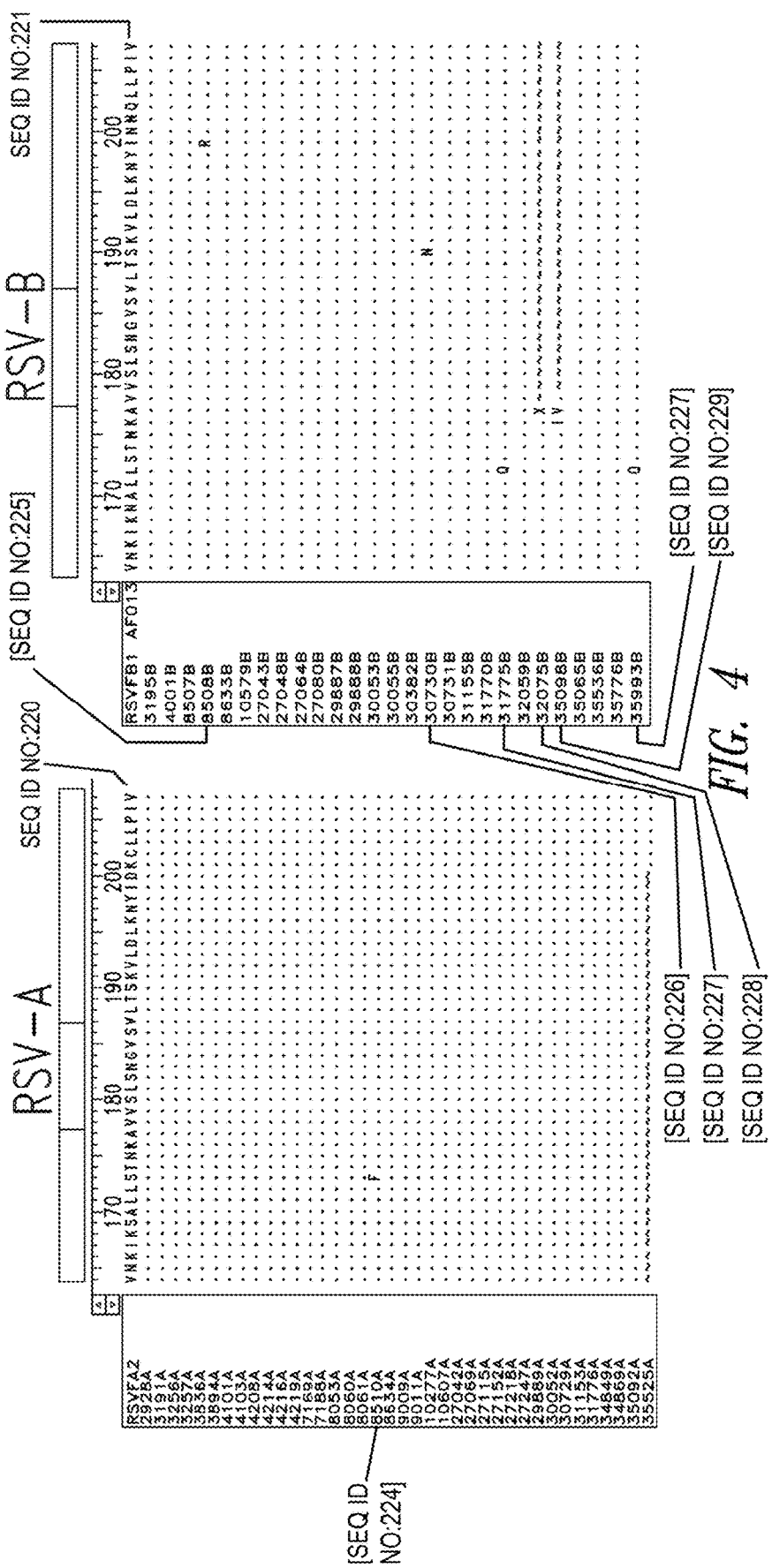
FIG. 4 depicts sequence information for the N-trimer groove of the F protein across primary RSV isolates, which are classified into two antigenic groups, RSV-A and RSV-B. Nasal aspirates from confirmed RSV cases from 2007-2012 were obtained (38 RSV-A and 27 RSV-B). Viral RNA was extracted and the F gene was sequenced. Among the RSV-A subset, when compared to the archetype RSV-A2 strain, only a single amino acid difference in one isolate was found in the 48-residue N-trimer region. The RSV-B trimer was also highly conserved with four single amino acid differences in distinct isolates.

The fact that RSV C-peptides inhibit membrane fusion validates the N-trimer as an exposed and vulnerable site on the F protein during entry. However, very little sequence information has been available for the full N-trimer to verify if the target was highly conserved across primary RSV isolates (which are classified into two antigenic groups, RSV-A and RSV-B). Therefore, the F gene from nasal aspirates from 65 patients with confirmed RSV infections admitted to a local hospital during 2007-2012 (38 cases of RSV-A and 27 cases of RSV-B) was sequenced. Viral RNA was extracted and sequenced using various primer sets for the F gene. When compared to the archetype A2 strain, only a single difference in one isolate of the RSV-A subset was found in the 48-residue N-trimer groove region (see, FIG. 4). The RSV-B N-trimer groove was also highly conserved with four single amino acid differences in distinct isolates (see, FIG. 4). After these primary isolates were sequenced, additional RSV F sequences became available (e.g., Chi et al., 2013, PLoS One 8:e64012; Papenburg et al., 2012, Emerg. Infect. Dis. 18:120-124), and a broader analysis including all available sequences (470 total) similarly confirms the N-trimer to be virtually identical within RSV-A (99.8%) and RSV-B (99.6%) isolates (there are three amino acid differences between RSV-A and RSV-B strains in the N-trimer). Furthermore, mapping the observed variations onto the N-trimer (Zhao et al., 2000, Proc. Natl. Acad. Sci. USA 97:14172-14177) reveals them to be in solvent exposed residues not expected to interact with groove-binding inhibitors, further confirming the N-trimer grooves to be excellent drug targets.

Example 2

Design and Validation of N-Trimer Mimics

Figure 5:
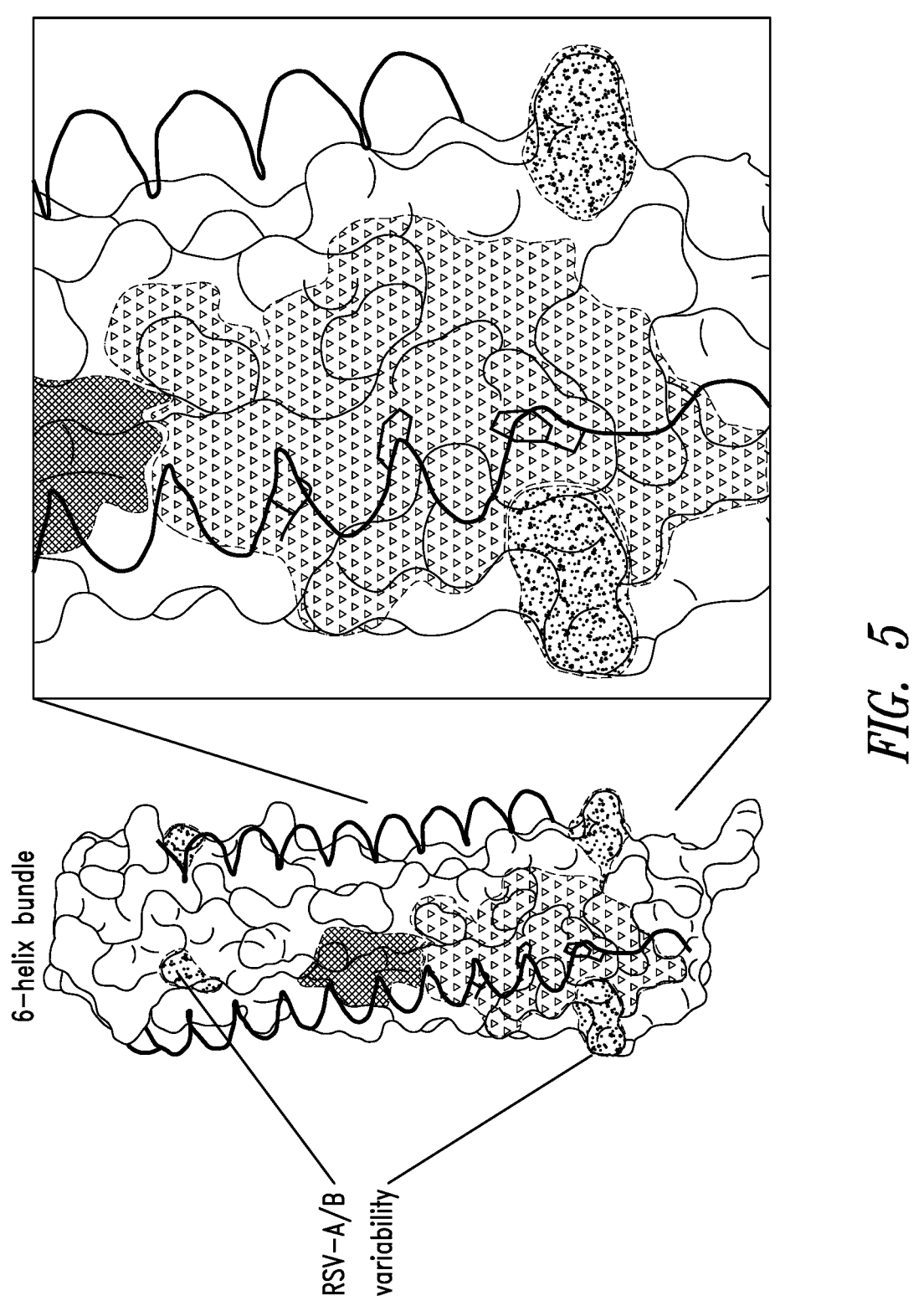

The high-resolution structure of the RSV trimer-of-hairpins as shown in FIG. 5 shows a hydrophobic pocket near the base of the N-trimer in orange (Zhao et al., 2000, Proc. Natl. Acad. Sci. USA 97:14172-7). This region, analogous to the hydrophobic pocket on the N-trimer of HIV gp41 to which PIE12 D-peptide trimer binds, presents a large, conserved surface area for inhibitor binding (~600 Å$^2$) and is an attractive inhibitory target. Residues that differ between RSV-A and RSV-B subtypes are shown in gray (see, FIG. 5).

Peptides corresponding to the N-trimer regions of viral membrane fusion proteins aggregate when produced in isolation due to its relatively hydrophobic composition (Eckert & Kim, 2001, Proc. Natl. Acad. Sci. USA 98:11187-92). To solve this problem and produce a soluble drug-screening target that presents the pocket as a trimer as it appears in vivo during viral entry, N-trimer mimics (also referred to as targets) were developed that comprise a designed soluble trimeric coiled-coil (IZ for "isoleucine zipper") fused to the N-terminus of the groove region or portions thereof. Such an N-trimer mimic used for HIV inhibitor screens, for example for identifying PIE12 D-peptide trimer, has been previously described (see, Welch et al., 2010, J. Virol. 84:11235-44; Welch et al., 2007, Proc. Natl. Acad. Sci. USA 104:16828-33; Eckert et al., 1999, Cell 99:103-15; U.S. Patent Publication 2010/0184663, incorporated by reference in their entirety). Several RSV N-trimer mimics were designed based on designs that authentically mimic the HIV N-trimer (Eckert et al., 2001, Proc. Natl. Acad. Sci. USA 98:11187-11192). Using the available RSV trimer-of-hairpins crystal structure as a guide (Zhao et al., 2000, Proc. Natl. Acad. Sci. USA 97:14172-14177), a series of progressively longer N-trimers were designed and produced (see, Table 4). N-trimer mimics were synthesized by standard solid-phase peptide synthesis methods and purified by reverse-phase HPLC. Molecular weights were confirmed by electrospray mass spectrometry. N-trimer peptides that vary in length and thus coverage of the N-trimer are fused to IZ peptides of varying length in order to maintain the trimeric coiled-coil structure.

TABLE 4

N-trimer Mimics Synthesized

| Target | Sequence | Experiments |
| --- | --- | --- |
| Ac-RSVA-IZN45 | Ac-IKKEIEAIKKEQEAIKKKIEAIEKEVNKIKSALLSTNKAVVSLSNGVSVLTSKVLDLKNYIDKQLLPIV-NH2 (SEQ ID NO: 43) | Crystallography |
| Ac-RSVB-IZN45 | Ac-IKKEIEAIKKEQEAIKKKIEAIEKEVNKIKNALLSTNKAVVSLSNGVSVLTSKVLDLKNYINNQLLPIV-NH2 (SEQ ID NO: 44) | Crystallography |
| BPEG2-GKG-RSVA-IZN45 | biotinPEG2-GKG-IKKEIEAIKKEQEAIKKKIEAIEKEVNKIKSALLSTNKAVVSLSNGVSVLTSKVLDLKNYIDKQLLPIV-NH2 (SEQ ID NO: 45) | Phage display, phage ELISA, SPR |
| BPEG2-GKG-RSVB-IZN45 | biotinPEG2-GKG-IKKEIEAIKKEQEAIKKKIEAIEKEVNKIKNALLSTNKAVVSLSNGVSVLTSKVLDLKNYINNQLLPIV-NH2 (SEQ ID NO: 46) | Phage display, phage ELISA, SPR |
| BPEG2-GKG-RSVA-IZN45 Full Mut | biotinPEG2-GKG-IKKEIEAIKKEQEAIKKKIEAIEKEVNKIKSWLLSTNKWVVSLSNWVSVLTSKVLWLKKYIDKQLLPIV-NH2 (SEQ ID NO: 47) | Phage ELISA, SPR |
| BPEG2-GKG-RSVB-IZN45 Full Mut | biotinPEG2-GKG-IKKEIEAIKKEQEAIKKKIEAIEKEVNKIKNWLLSTNKWVVSLSNWVSVLTSKVLWLKKYINNQLLPIV-NH2 (SEQ ID NO: 48) | Phage ELISA, SPR |
| BPEG2-GKG-RSVA-IZN45 WT-top | biotinPEG2-GKG-IKKEIEAIKKEQEAIKKKIEAIEKEVNKIKSALLSTNKAVVSLSNWVSVLTSKVLWLKKYIDKQLLPIV-NH2 (SEQ ID NO: 49) | Phage ELISA, SPR |
| BPEG2-GKG-RSVB-IZN45 wt top | biotinPEG2-GKG-IKKEIEAIKKEQEAIKKKIEAIEKEVNKIKNALLSTNKAVVSLSNWVSVLTSKVLWLKKYINNQLLPIV-NH2 (SEQ ID NO: 50) | Phage ELISA, SPR |
| BPEG2-GKG-RSVA-IZN45 WT-bot | biotinPEG2-GKG-IKKEIEAIKKEQEAIKKKIEAIEKEVNKIKSWLLSTNKWVVSLSNGVSVLTSKVLDLKNYIDKQLLPIV-NH2 (SEQ ID NO: 51) | Phage ELISA, SPR |
| BPEG2-GKG-RSVB-IZN45 wt bot | biotinPEG2-GKG-IKKEIEAIKKEQEAIKKKIEAIEKEVNKIKNWLLSTNKWVVSLSNGVSVLTSKVLDLKNYINNQLLPIV-NH2 (SEQ ID NO: 52) | Phage ELISA, SPR |
| BPEG2-GKG-RSVA-IZN45 WT-mid | biotinPEG2-GKG-IKKEIEAIKKEQEAIKKKIEAIEKEVNKIKSWLLSTNKAVVSLSNGVSVLTSKVLWLKKYIDKQLLPIV-NH2 (SEQ ID NO: 53) | Phage ELISA, SPR |
| BPEG2-GKG-RSVB-IZN45 wt mid | biotinPEG2-GKG-IKKEIEAIKKEQEAIKKKIEAIEKEVNKIKNWLLSTNKAVVSLSNGVSVLTSKVLWLKYINNQLLPIV-NH2 (SEQ ID NO: 54) | Phage ELISA, SPR |
| BPEG2-GKG-RSVB-IZN30 | biotinPEG2-GKG-IKKEIEAIKKEQEAIKKKIEAIEKEVVSLSNGVSVLTSKVLDLKNYINNQLLPIV-NH2 (SEQ ID NO: 55) | Phage display, phage ELISA, SPR |
| BPEG2-GKG-RSVA-IZN18 | biotinPEG2-GKG-IKKEIEAIKKEQEAIKKKIEAIEKEIEVLTSKVLDLKNYIDKQLL-NH2 (SEQ ID NO: 56) | Phage display, phage ELISA, SPR |
| BPEG2-GKG-RSVB-IZN18 | biotinPEG2-GKG-IKKEIEAIKKEQEAIKKKIEAIEKEIEVLTSKVLDLKNYINNQLL-NH2 (SEQ ID NO: 57) | Phage display, phage ELISA, SPR |

TABLE 4-continued

N-trimer Mimics Synthesized

| Target | Sequence | Experiments |
|---|---|---|
| BPEG2-GKG-RSVB-IZN21 | biotinPEG2-GKG-<u>IKKEIEAIKKEQEAIKKKIEAIEKEIEVLTSK</u>VLDLKNYINNQLLPIV-NH2 (SEQ ID NO: 58) | Phage display, phage ELISA, SPR |
| Ac-RSV-A IZN21 | Ac-<u>IKKEIEAIKKEQEAIKKKIEAIEKEIEVLTSK</u>VLDLKNYIDKQLLPIV-NH2 (SEQ ID NO: 59) | Crystallography |
| BPEG2-GKG-RSVA-IZN48 | biotinPEG2-GKG-<u>IKKEIEAIKKEQEAIKKKIEALEGEVNKIKSA</u>LLSTNKAVVSLSNGVSVLTSKVLDLKNYIDKQLLPIV-NH2 (SEQ ID NO: 60) | Phage ELISA, SPR |
| BPEG2-GKG-RSVB-IZN48 | biotinPEG2-GKG-<u>IKKEIEAIKKEQEAIKKKIEALEGEVNKIKNA</u>LLSTNKAVVSLSNGVSVLTSKVLDLKNYINNQLLPIV-NH2 (SEQ ID NO: 61) | Phage ELISA, SPR |
| RSVB-IZN48 | <u>IKKEIEAIKKEQEAIKKKIEALEGEVNKIKNA</u>LLSTNKAVVSLSNGVSVLTSKVLDLKNYINNQLLPIV-NH2 (SEQ ID NO: 62) | Crystallography |
| RSVA-N49IZ-GKG-Glu(biotinyl-PEG)-NH2 | LEGEVNKIKSALLSTNKAVVSLSNGVSVLTSKVLDLKNYIDKQLLPIVN<u>IKKEIEAIKKEQEAIKKKIEAI</u>-GKG-Glu(biotinyl-PEG)-NH2 (SEQ ID NO: 63) | Phage ELISA, SPR |
| RSVB-N49IZ-GKG-Glu(biotinyl-PEG)-NH2 | LEGEVNKINALLSTNKAVVSLSNGVSVLTSKVLDLKNYINNQLLPIVN<u>IKKEIEAIKKEQEAIKKKIEAI</u>-GKG-Glu(biotinyl-PEG)-NH2 (SEQ ID NO: 64) | Phage ELISA, SPR |

IZ portion of the N-trimer mimic is single-underlined.
"Ac" indicates capping at N-terminal with acetyl group
"NH2" indicates capping at C-terminus with an amide group
"BiotinPEG2" = N-Biotinyl-NH-(PEG)$_2$-COOH DIPEA (20 atoms), EMD Millipore Catalog # 851029
Double-underlined "K" residues are L-lysines to allow trypsin cleavage of the target (e.g., elution method during phage display library screening)
Bold residues highlight sequence differences of RSV-B type from RSV-A type
"Glu(biotinyl-PEG)" = Fmoc-Glu(Biotinyl-PEG)-OH, EMD Millipore Catalog #852102

Biophysical analysis of RSVA-IZN18 (also referred to as RSV-IZN18) via circular dichroism and sedimentation equilibrium analytical ultracentrifugation demonstrated that RSVA-IZN18 is helical and trimer as designed (data not shown), and therefore would serve as a good phage display target. N-trimer targets used for mirror-image phage display library screening were chemically synthesized with D-amino acids using standard solid-phase peptide synthesis.

Figure 6:
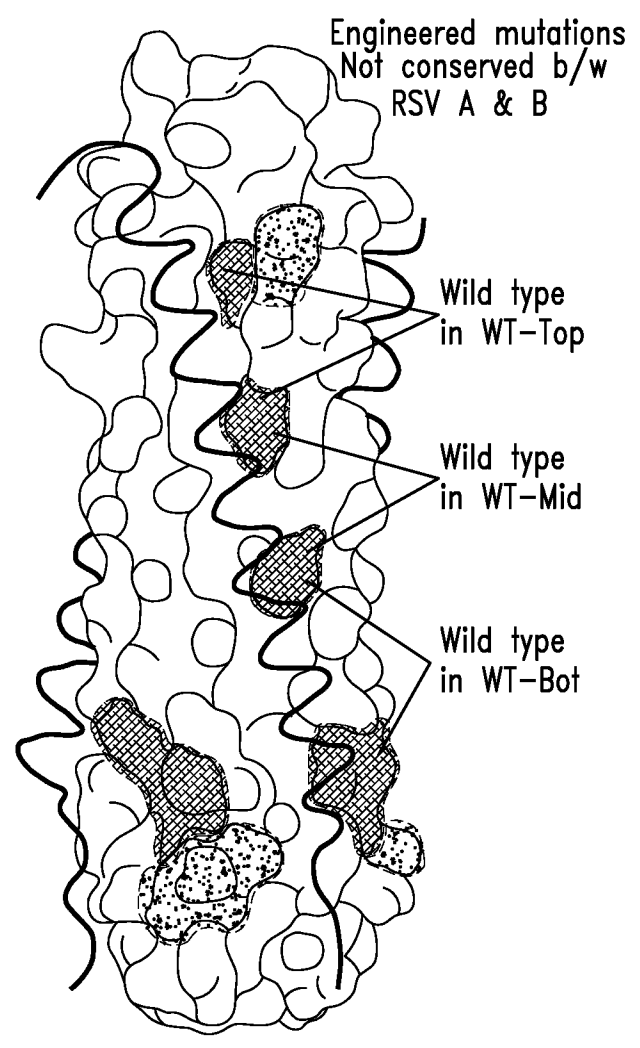
Figure 7:
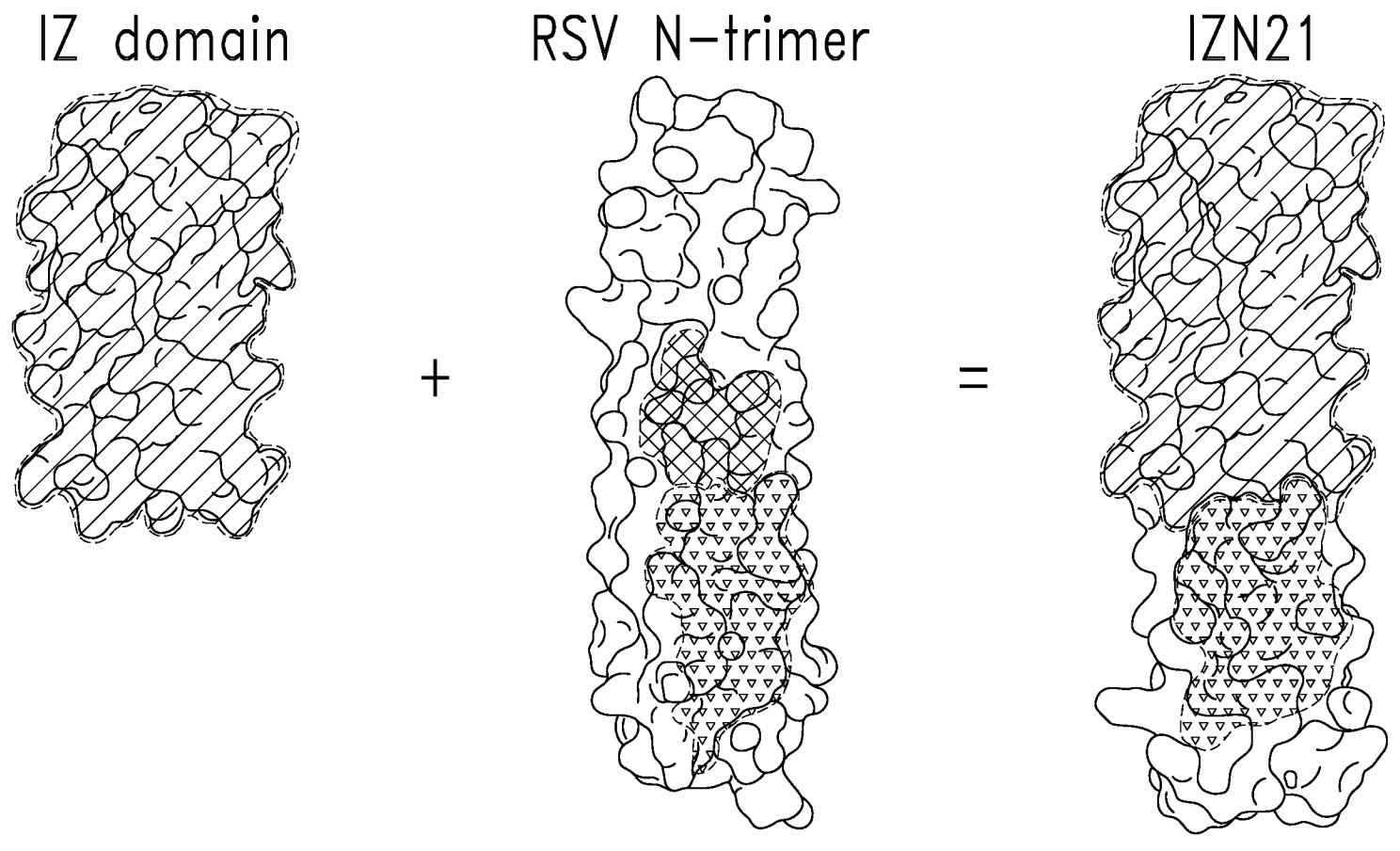

IZN45 N-trimer mimic comprises the IZ domain, a highly soluble, designed coiled-coil that helps solubilize the N-trimer, along with the C-terminal (bottom) 45 residues of the RSV N-trimer. IZN45 encompasses the full ordered portion of the N-trimer except for three N-terminal residues (removed to maintain a continuous heptad repeat with the IZ domain). The interactions between 35-residue RSV C-peptides, T108 and T118 (Lambert et al., 1996, Proc. Natl. Acad. Sci. USA 93:2186-2191), and IZN45 was examined by surface plasmon resonance (SPR). SPR is a gold standard assay to measure the kinetics and affinity of biological interactions. SPR was performed to confirm peptide binding to designed RSV targets using a ProteOn (Biorad) instrument. The Biotinylated L-form of RSV target IZN45 was captured onto one lane of a NeutrAvidin coated SPR chip. A mutant version of IZN45 containing four mutated residues along the N-trimer groove designed to disrupt binding (IZN45 Full Mut, negative control) was captured onto a separate lane of the NeutrAvidin chip. T118, corresponding to the C-terminal portion of the RSV F ectodomain, which is known to interact with the RSV N-trimer groove, was flowed over the various surfaces. T118 bound to IZN45 with high affinity (~1 nM) but did not bind to the mutant target, and the data were fit using the simplest Langmuir interaction model. The surfaces were regenerated with a detergent (0.1% SDS) after each injection of analyte. Various concentrations of T118 were measured in duplicate or triplicate injections. D-peptide interactions with IZN45 and IZN45-Full Mut surfaces were also measured using this method. In summary, the SPR data showed the interactions to be strong (with KDs ~5-8 nM) and specific (no binding to a control target, IZN45 Full Mut, containing engineered disrupting mutants along the N-trimer groove) (see, FIG. 6). T108 binds to the bottom ~80% of the N45 region, and T118 binds to the top ~80%. To validate IZN45 in the context of phage display, control phage displaying T108 was constructed, and 'phage ELISA' was performed that ensured this phage bound specifically to IZN45 but not IZN45 Full Mut (data not shown). Thus, IZN45 was validated via SPR and phage ELISA as presenting the N-trimer in a native conformation. Since it displays the entire groove, providing more flexibility in possible target regions, IZN45 was selected as a target for mirror-phage display library screening along with IZN21, which comprises the hydrophobic pocket near the base of the N-trimer (see, FIG. 7).

Example 3

Figure 8:
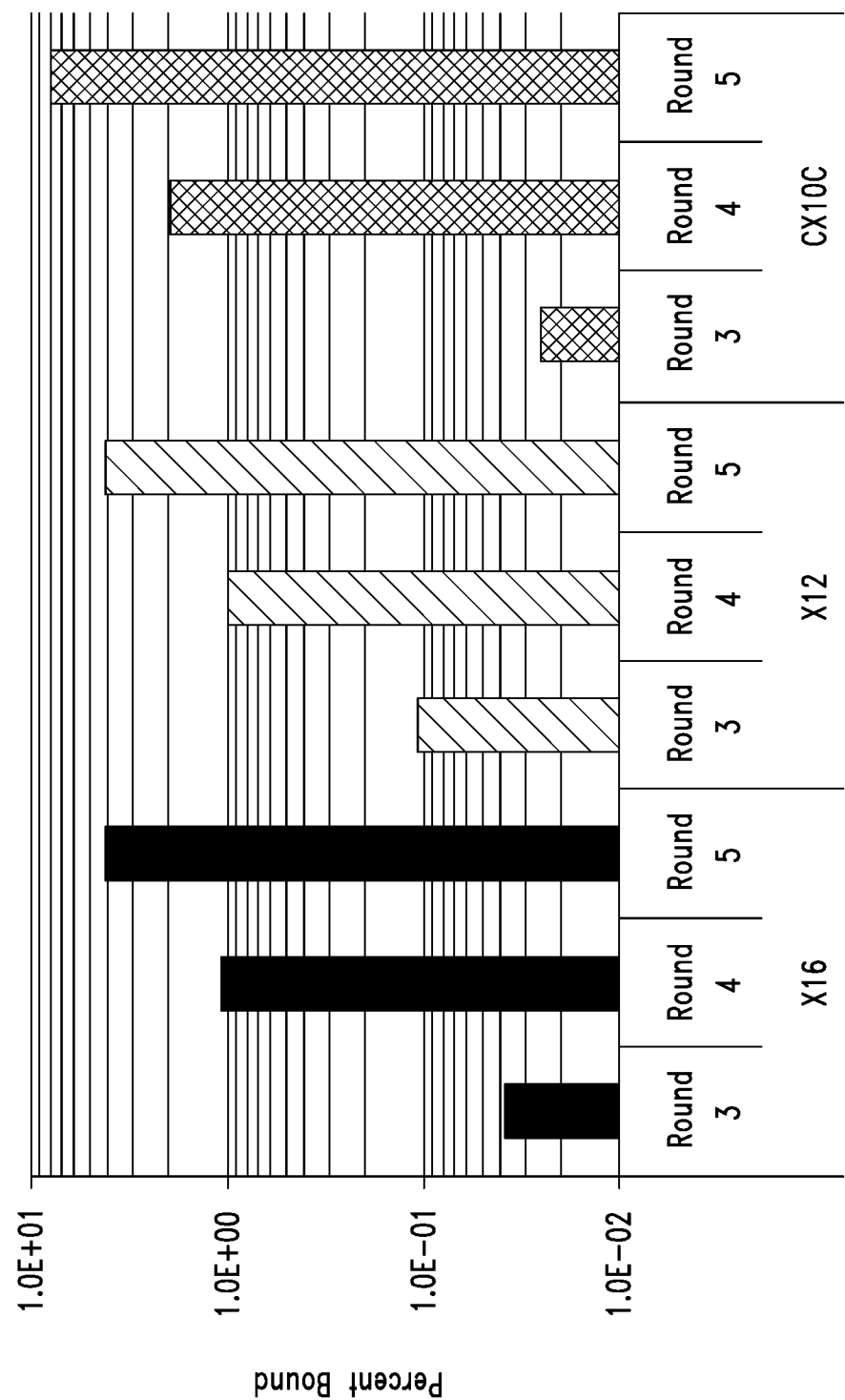
FIG. 8 depicts phage display enrichment for the highest-affinity clones in 3 libraries (X16, X12, and CX10C) screened with IZN45 target. The stringency of the selection was increased by lowering the solution target concentration in each round. The number of phage captured from surfaces coated with target, but not from blank surfaces (not shown), increased each round when the round outputs were analyzed at the same condition. These data were an early indication that the libraries became enriched for high affinity clones.

Identification of RSV D-Peptide (RSVP) Inhibitors of RSV Entry Using Mirror-Image Phage Display Using D-versions of N-trimer mimics IZN45 and IZN21 as targets, mirror-image phage display library screening was performed to identify peptides that bind to the N-trimer groove and inhibit RSV entry (see, Table 2). Two commercially available linear peptide phage display libraries (NEB and Creative Biolabs) of the format X12 and X16 (12 and 16 consecutive randomized amino acids where X is any X any amino acid or X is any amino acid except Cys, respectively), and a disulfide-constrained (circularized) library of the form CX10C (see, Eckert et al., 1999, Cell 99:103-115; Welch et al., 2007, Proc. Natl Acad. Sci. USA 104:16828-16833; U.S. Patent Publication 2010/0184663, each of which is incorporated by reference in its entirety). The X16 and CX10C library oligonucleotides were made using a mix of 19 trimer phosphoramidites (Glen Research) that encodes all amino acids except Cys while also excluding stop codons—two sources that can significantly reduce functional diversity of phage libraries. In all, >50 billion peptides were screened against IZN45 D-peptide target in 5-6 rounds of mirror-image phage display. In brief, a library of peptides was encoded in the phage genome and used to transform bacteria. Each individual phage displays a unique peptide that is encoded in its genome. The phage were incubated with a selected biotinylated N-trimer mimic bound to magnetic streptavidin beads. Unbound phage were washed away and phage are eluted from the beads, amplified, and used for the next found of screening. RSV-A and RSV-B subtypes were alternated in sequential rounds of selection to ensure that 'winning' peptides recognize grooves of both subtypes. The selection pressure was increased from round to round by increasing the number and/or length of washes over 3-6 rounds. Analyzing the outputs from sequential rounds reveals a dramatic progression in the percent of phage captured per round (see, FIG. 8).

Deep sequencing and bioinformatics methods were used to identify phage clones that dominated the selections while filtering out 'cheater' phage (e.g., phage with a growth advantage). Growth advantage was detected by comparing sequences of pre- and post-amplification libraries (growth advantage if ratio >1). Deep sequencing was used to discover the DNA sequences (and hence, the peptide sequences) of the phage that remain following a round of phage display. The phage outputs from each round of phage display were PCR amplified using primers containing a unique nucleotide sequence or barcode for each round of screening. The amplified rounds are combined and sequenced en masse (Ion Torrent Proton system, Life Technologies). The barcode allows bioinformatics separation of the phage sequences by round of phage display screening, and the sequences from each round are aligned, grouped, and sorted by abundance. The most abundant sequences typically represent the peptide sequences with highest affinity for the target of interest. The number of reads typically allows statistical information to be derived about the relative importance of a particular amino acid at a given position. In naive phage libraries, the number of possible sequences is typically greater than the physical diversity of the phage display library itself (often by many orders of magnitude). In this case, it is important to identify the preferred residues, which appear at high frequency at a given position. This 'consensus sequence' usually contributes the greatest amount of energy to the binding interface. Secondary or "consensus-constrained" phage libraries can then be constructed in which the consensus sequence is not varied to identify optimal binders (see, Table 5). This allows greater coverage of all possible sequences containing the consensus sequence to be surveyed. Screening of secondary libraries allows higher affinity binders to be discovered. A strong consensus sequence was identified using deep sequencing of nearly 1.5 million sequences total from the 5$^{th}$ round of phage display from the three naïve libraries. Remarkably, both linear libraries, X12 and X16, revealed the same consensus sequence (LPXPXWW (SEQ ID NO:1)). The position of this motif was not fixed within the linear sequences. However, the crystal structure of X12-47 (SKVI LPEPFWWP (SEQ ID NO:10)) indicates residues C-terminal to the WW are unlikely to contribute to RSVP binding since the C-terminal proline makes no interactions with N45 whereas the C-terminal W is intimately associated with the N-terminal region of N45. Furthermore, this consensus was commonly identified at the extreme C-terminus of the library peptides (no additional residues beyond 'WW').

For discovery of the various RSV peptides described herein, multiple naive libraries and secondary libraries were used to identify the highest-affinity binders and most potent inhibitors. Additional data (e.g., mutant data or a high-resolution structure) gathered about the 'winning' sequences from the naive library often further informs the design of secondary libraries.

Figure 9:
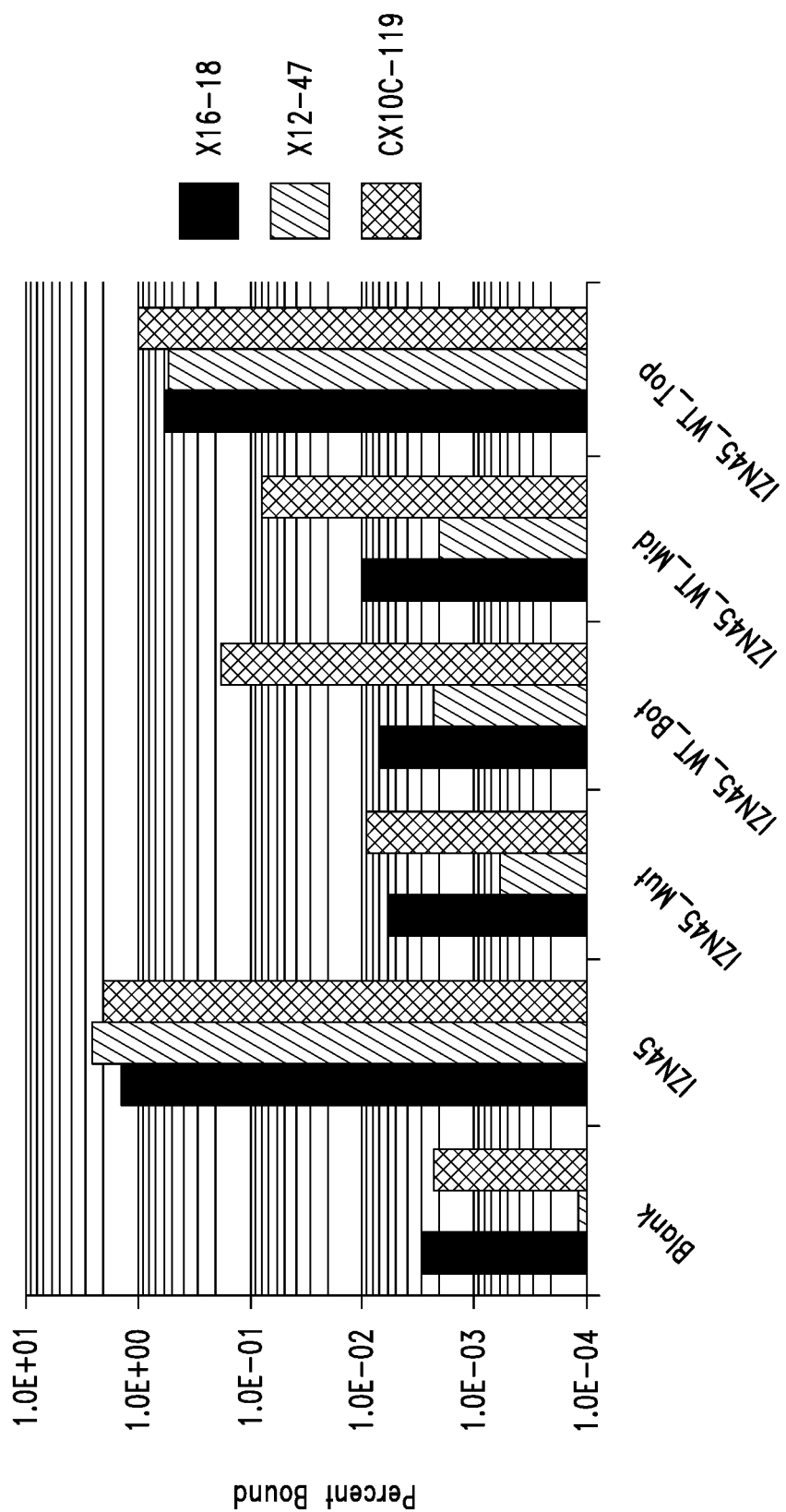
FIG. 9 depicts binding of identified clones to the N-terminus of the RSV N-trimer. The binding of a few 'winning' clones from each library to wild-type and mutant versions of IZN45 as demonstrated by phage ELISA reveals that the clones bind near the N-terminus of the N45 region (top half of the groove). The linear clones were more disrupted for binding to IZN45_WT-Bot and IZN45_WT-Mid than the presumably more compact circularized clones.

Clonal stocks of the 'winning' phage from the naive phage libraries, X16-18 (SEQ ID NO:4), X12-47 (SEQ ID NO:10), and CX10C-119 (SEQ ID NO:19), were tested for specificity by phage ELISA, comparing binding of wild type and mutant IZN45 targets (see, FIG. 9). All identified clones bind to the N-terminus of the RSV N-trimer.

TABLE 5

Summary of RSV targets, naïve libraries screened, discovered consensus sequences, designed secondary libraries, and examples of discovered peptides.

| Designed RSV Target | Naive phage display library | Discovered consensus sequence | Designed secondary library | Example of discovered peptide sequence |
|---|---|---|---|---|
| RSV-B IZN45 | X16 | LPXPXWW (SEQ ID NO: 41) | N/A | X16-18 |
| RSV-B IZN45 | X12 | LPXPXWW (SEQ ID NO: 1) | XXXXLPX PXWW (SEQ ID NO: 65) | RSVP7 |
| RSV-B IZN21 | CX10C | (R/E)X (H/E/Y) WLLDW (SEQ ID NO: 2) | XXCXN(R/ E/G/K)X (H/E/Y/ D/Q)WLLD WCXX (SEQ ID NO: 66) | RSVP32 |

"X" in the X12 naive library and designed secondary library represents all 20 natural amino acids.
"X" in the X16 and CX10C naive libraries, as well as the designed CX10C secondary library represents all 20 natural amino acids except Cys.

Known L-peptide inhibitors of RSV, shown in Table 6, were used as positive controls.

TABLE 6

(L) Inhibitors of RSV
(controls for D-peptide studies)

| Compound Name | MW (Da) | Sequence | Kd (uM) | IC50 (uM) |
|---|---|---|---|---|
| YG-T118 | 4095.531 | YG-FDASISQVNEKINQSLAFIR KSDELLHNVNAGKST-NH2 (SEQ ID NO: 67) | | 8 |
| YG-T118-Tricasso | 13922.8332 | [AcYG-FDASISQVNEKINQSLAFIR KSDELLHNVNAGKST-G (PEG6)]K[peptide]-GK[peptide]-G-NH2, wherein the peptide monomers are each: AcYGFDASISQVNEKINQSL AFIRKSDELLHNVNAGKSTG (PEG6) (SEQ ID NO: 68) | | 0.65 |
| YG-T118-GC-Cholesterol | | YG-FDASISQVNEKINQSLA FIRKSDELLHNVNAGKST-GC-Cholesterol (SEQ ID NO: 69) | | 0.64 |
| Ac-RSV-A IZN45 | 7715.193 | Ac-IKKEIEAIKKEQEAIKK KIEAIEKEVNKIKSALLSTN KAVVSLSNGVSVLTSKVLDL KNYIDKQLLPIV-NH2 (SEQ ID NO: 70) | | 0.006 |
| (Biotin-PEG2)GK G-RSVA IZN48 | 8383.27 | (biotin-PEG2)GKG-IKK EIEAIKKEQEAIKKKIEALE GEVNKIKSALLSTNKAVVSL SNGVSVLTSKVLDLKNYIDK QLLPIV-NH2 (SEQ ID NO: 71) | | 0.215 |
| RSVA N49IZ-GKG(Glu-Biotinyl-PEG) | 8629 | LEGEVNKIKSALLSTNKAVV SLSNGVSVLTSKVLDLKNYI DKQLLPIVNIKKEIEAIKKE QEAIKKKIEAI-GKG-(Glu-biotinyl-PEG)-NH2 (SEQ ID NO: 72) | | 0.102 |

"Ac" indicates capping at N-terminal with acetyl group
"NH2" indicates capping at C-terminus with an amide group
"BiotinPEG2" = N-Biotinyl-NH-(PEG)$_2$-COOH DIPEA (20 atoms), EMD Millipore Catalog # 851029
"Glu(biotinyl-PEG)" = Fmoc-Glu(Biotinyl-PEG)-OH, EMD Millipore Catalog #852102
Peptides are cross-linked to the PEG scaffolds (for trimerization) via the unique primary amine (epsilon amino group of Lysine sidechain)
"(PEG6)" indicates insertion of PEG6 by linking of PEG6 to the C-terminus of the preceding amino acid and to the N-terminus of the following amino acid
"Peptide" indicates conjugation to the same peptide as disclosed within brackets, to form a homotrimer Example 4

Characterization of RSV D-Peptide Inhibitors

Peptides from the 'winning' phage clones from each library were synthesized as D-peptides. If solubility of the peptides was limited, N- or C-terminal charged residue(s) (e.g., lysine) were attached as necessary as previously described for HIV peptides in Eckert et al., 1999, Cell 99:103-15, incorporated by reference in its entirety. Binding affinity and kinetics of the D-peptide inhibitors to the IZN45 and IZN45 mutants was characterized by SPR (Biacore 3000), using methods as described in Welch et al., 2007, Proc. Natl. Acad. Sci. USA 104:16828-33, incorporated by reference in its entirety. All of the D-peptide inhibitors tested bind specifically to IZN45 with minimal binding to IZN45_Mut, with a $K_D$ range of 2-225 μM (the expected affinity for naïve phage display hits).

Figure 10A:
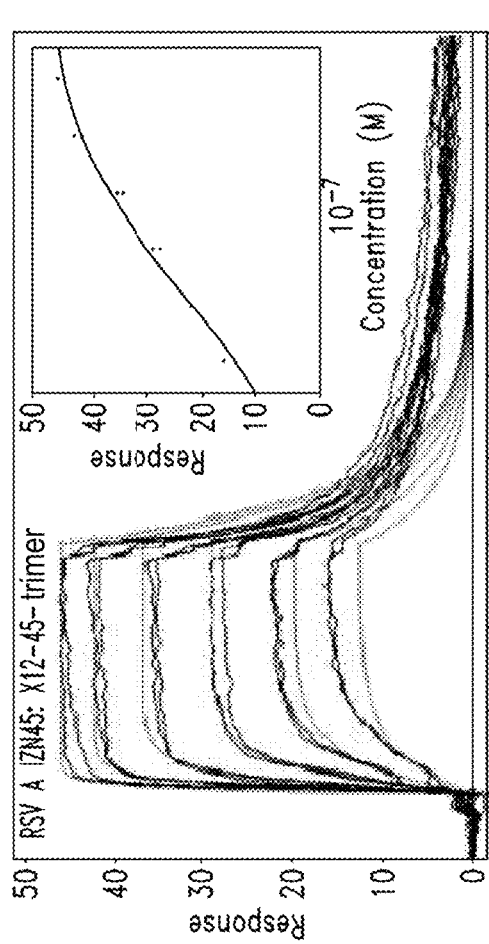
FIGS. 10A and 10B depict binding of D-peptides to RSV-A and RSV-B, respectively. All of the D-peptide monomers and trimers tested bound to RSV-A and RSV-B versions of IZN45 with approximately equal affinity. The X12-45 D-peptide trimer kinetic data and binding isotherms (insets) to both targets are shown, and the measured $K_D$ values were 49 nM and 66 nM, respectively.
Figure 10B:
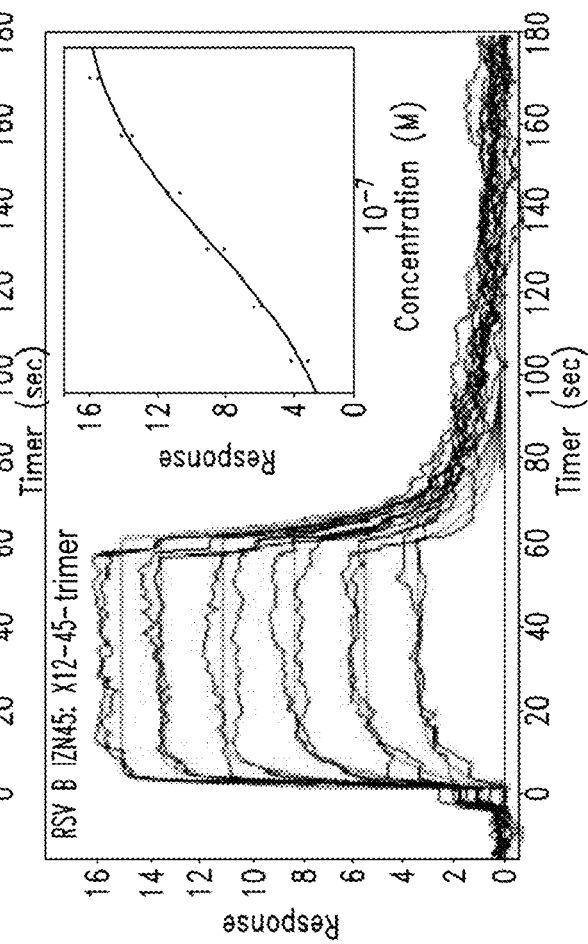
Figure 14:
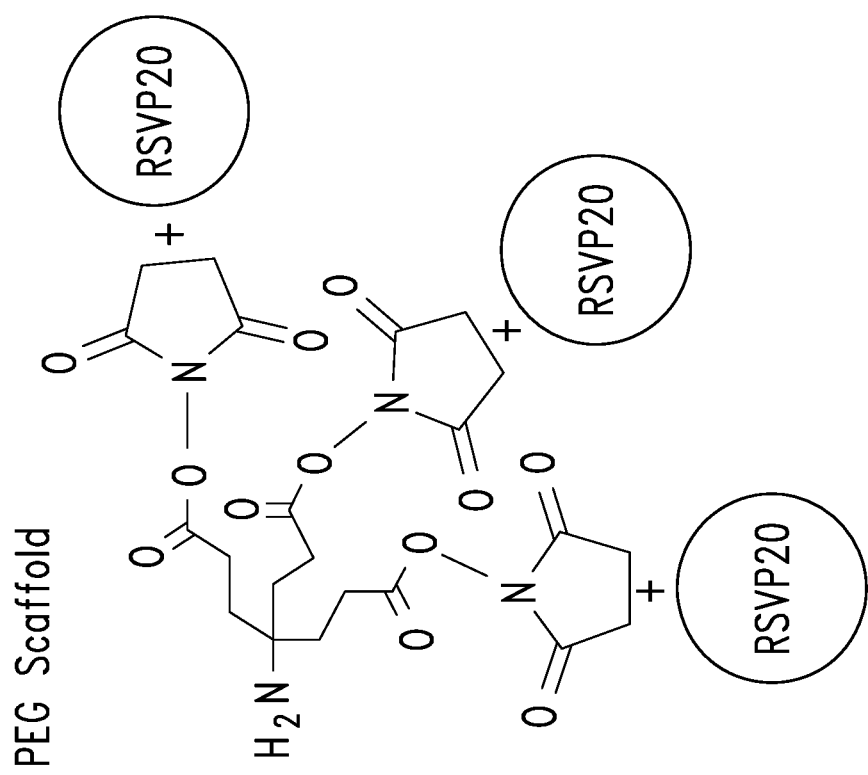
FIG. 14 depicts an embodiment of trimerization of a D-peptide using a scaffold. In one embodiment, the scaffold may incorporate a PEG spacer. Trimerization of the RSVP20 D-peptide increases binding avidity (RSVP20 monomer $K_D$=3.7 µM; RSVP20 trimer $K_D$=0.3 nM).

Because trimerization of anti-HIV D-peptides provided significant potency enhancement due to an avidity effect for the HIV N-trimer (Welch et al., 2010, J. Virol. 84:11235-11244; Denton et al., 2011, J. Virol. 85:7582-7593), trimers of selected high affinity RSV D-peptide monomers were produced (see, Table 7). These RSV trimers were constructed without the benefit of co-crystal structure guiding their design, and therefore were conservative, using polyethylene glycol (PEG) linkers that were likely longer than necessary to bridge the distance between the three grooves of the N-trimer (see, e.g., FIG. 14). Trimerization boosted affinity 50 to 350-fold, and the $K_D$ of the highest affinity trimer is ~50 nM. For example, the RSVP20 monomer has a $K_D$ of 3.7 while the RSVP20 trimer has a $K_D$ of 0.3 nM (~10,000-fold improvement in binding affinity). Importantly, the highest affinity monomers and trimers also bind an RSV-A version of IZN45 with similar affinity to the RSV-B version used for selection (see, FIGS. 10A and 10B).

The RSV Syncytia reduction assay was used to evaluate D-peptide inhibitors of RSV entry ($IC_{50}$). In brief, 293 T cell were plated in a 96-well plate and a 6-well plate. The cells in the 96-well plate were co-transfected with DNA encoding the RSV F protein (or RSV G protein as a negative control) and DNA encoding firefly luciferase downstream of multiple GAL4 binding sites (CheckMate Mammalian Two-Hybrid system, Promega). These cells were designated the effector cells. The cells in the 6-well plate were transfected with GAL4:Id and VP16:MyoD fusion constructs, which interact and drive gene expression in the presence of GAL4 binding sites. These cells were the target cells. At 24 hours post-transfection, the media is removed from the effector cells and D-peptide inhibitors at 2× concentration (diluted in fresh media) were added. Also at 24 hours post-transfection, the target cells are washed with PBS, gently dissociated from the 6-well plate using Versene (0.48 mM EDTA in PBS), and overlaid (at equal volume) onto the effector cells containing 2× inhibitor. At 48 h post-transfection, the cells are lysed using Glo Lysis Buffer (Promega). Bright Glo luciferase assay substrate is added and luminescent signal from expressed luciferase is measured. Luciferase is only expressed in effector cells that fuse (form syncytia) with target cells. $IC_{50}$ values of various D-peptides tested are set forth in Table 7.

Figure 15:
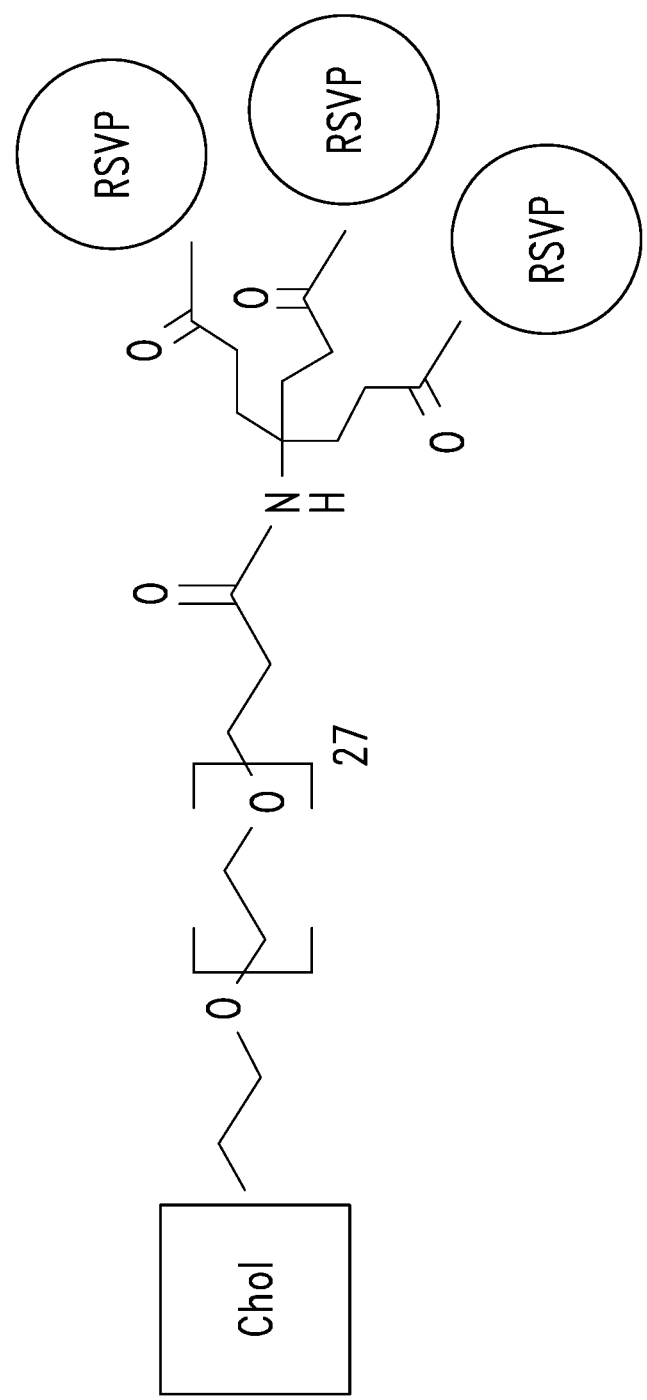
FIG. 15 depicts an embodiment of a D-peptide (also referred to as RSVP) trimer where a '$4^{th}$ arm' scaffold in which an additional polyethylene glycol (PEG) arm conjugated to a 'cargo' molecule (e.g., cholesterol, fatty acid, large molecular weight PEG, albumin binding tag) (Francis et al., 2012, Bioconjug. Chem. 23:1252-8) is added to enhance pharmacokinetics and potency. Appending cholesterol localizes the D-peptide trimer at lipid rafts on the cell membrane.
Figure 16:
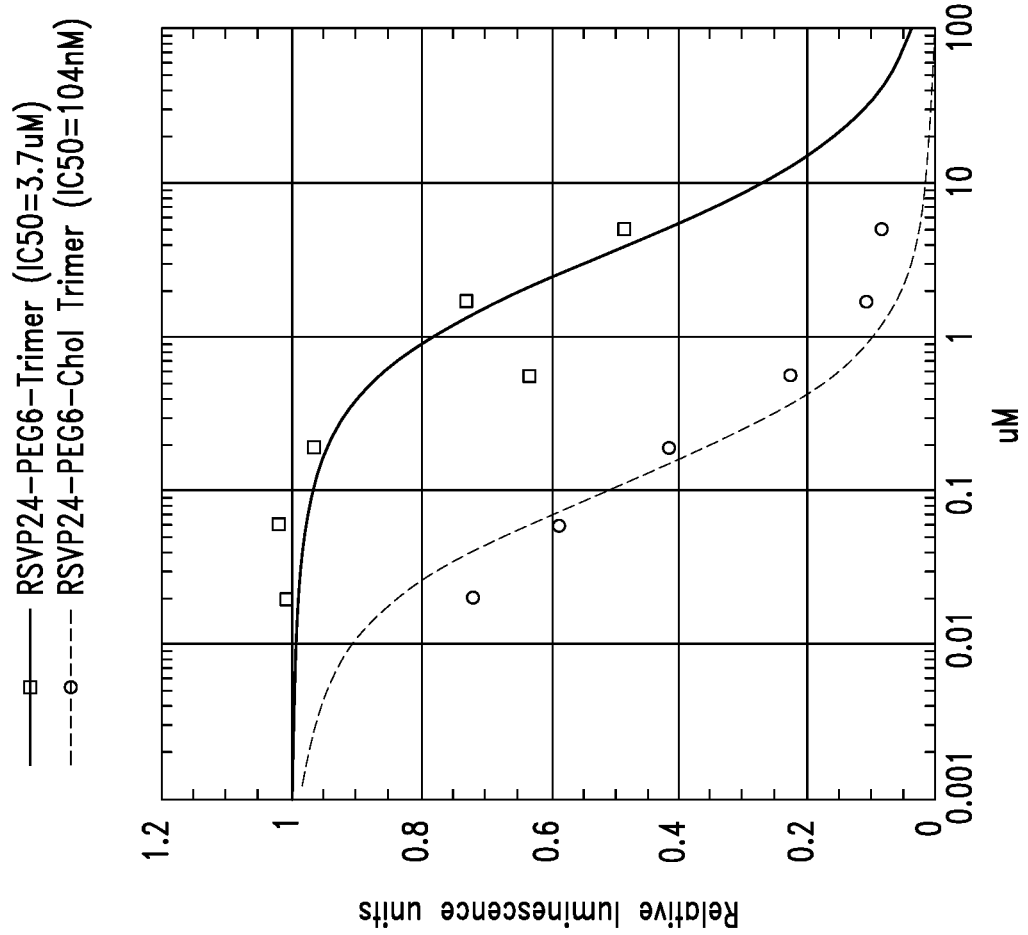
FIG. 16 depicts potency enhancing effect of membrane tethering by the addition of cholesterol to RSVP24 D-peptide trimer using a PEG6 linker. Potency is improved 35-fold as measured in a syncytia reduction assay.

Depending on the observed $P_K$ properties of the compounds, $P_K$ optimization may be desirable. $P_K$-enhancing groups may be added to the RSV D-peptide trimers using custom '4th-arm' scaffolds in which an additional PEG arm (e.g., $PEG_{12}$, $PEG_{16}$, $PEG_{24}$, $PEG_{25}$, $PEG_{26}$, $PEG_{27}$, $PEG_{28}$, $PEG_{29}$, $PEG_{30}$, $PEG_{31}$, $PEG_{32}$, $PEG_{33}$, $PEG_{34}$, $PEG_{35}$, or $PEG_{36}$) is conjugated to various 'cargoes' (e.g., cholesterol, sterol, sugar, maltose binding protein, ubiquitin, streptavidin, immunoglobulin domain, keyhole limpet hemacyanin, sperm whale myoovalbumin, bovine pancreatic trypsin inhibitor, green fluorescent protein, gold particle, magnetic particle, agarose bead, lactose bead, fatty acid, a high molecular weight PEG, or serum albumin) (see, U.S. Patent Publication 2014/0323392; Francis et al., 2012, Bioconjug. Chem. 23:1252-8, each of which is incorporated by reference in its entirety). For the HIV PIE12 D-peptide trimer inhibitor, for example, appending cholesterol increased its half-life several-fold and enhanced potency by ~30 to 150-fold (depending on the type of assay) by pre-localizing the inhibitor at lipid rafts on the cell membrane, the specific sites of HIV viral entry. An example of a $4^{th}$ arm scaffold for adding cholesterol to an RSVP trimer is shown in FIG. 15. The addition of cholesterol using a $4^{th}$ arm scaffold to a trimer of RSVP24 (SEQ ID NO:23) improves potency 35-fold as measured in a syncytia reduction assay (see, FIG. 16).

Geometry optimization is further conducted to: identify the optimal length of the PEG linker between the scaffold and D-peptides; compare N-terminal vs. C-terminal attachment site of PEG linker; and identify optimal length of the PEG linker between the potency cargo enhancing molecule and the D-peptide trimer. Strength of binding avidity is related to PEG linker length. In some embodiments, the shortest connection may be preferred. For the D-peptides identified from the linear libraries, cross-linking of the N-termini may be a preferred than using a C-terminal lysine since the binding interface is at or near the C-terminus of the D-peptide and N-terminal residues are disordered.

TABLE 7

RSV D-peptides tested by SPR for ($K_D$) or syncytia reduction assay ($IC_{50}$)

X16 library vs. RSVB-IZN45 target

| Synthesized peptide | MW (Da) | Sequence | Kd (µM) | IC50 (µM) | Subsequent trimer(s) made from peptide | Kd (µM) | IC50 (µM) |
|---|---|---|---|---|---|---|---|
| X16-16 | 2136.4 | DYLPLPEPRWWFPEYQ-NH2 (SEQ ID NO: 73) | | | | | |
| X16-18 | 2191.5844 | SLKYWWMEELPLPKWW-NH2 (SEQ ID NO: 74) | RSV-B/IZN45: 16 | | | | |
| Ac-X16-18 | 2233.627 | Ac-SLKYWWMEELPLPKWW-NH2 (SEQ ID NO: 75) | RSV-B/IZN45: 11 | | | | |
| X16-18-GG | 2305.72 | SLKYWWMEELPLPKWW-GG-NH2 (SEQ ID NO: 76) | RSV-B/IZN45: 24 | | | | |
| Ac-X16-18-GG | 2347.731 | Ac-SLKYWWMEELPLPKWW-GG-NH2 (SEQ ID NO: 77) | RSV-B/IZN45: 5.4 | | | | |
| Ac-X16-18-GG(PEG6)K | 3139.5194 | Ac-SLK*YWWMEELPLPK*WW-GG(PEG6)K-NH2 (SEQ ID NO: 78) | | | ^Ac-X16-18-GG(PEG6)K-trimer | RSV-B/IZN45:0.01 RSV-A/IZN45:0.074 | |

TABLE 7-continued

| RSV D-peptides tested by SPR for ($K_D$) or syncytia reduction assay ($IC_{50}$) | | | | | | | |
|---|---|---|---|---|---|---|---|
| Ac-X16-18-GG (PEG6)K scram | 3139.5194 | Ac-LWK*SWEWLEK*WPMYPL-GG(PEG6)K-NH2 (SEQ ID NO: 79) | | | | | |
| X16-20-GK | 2309.6 | HWLPLQPWWDDIPVWH-GK-NH2 (SEQ ID NO: 80) | RSV-B/IZN45: 2.0 | | | | |
| Ac-X16-20-GK | 2351.66 | Ac-HWLPLQPWWDDIPVWH-GK-NH2 (SEQ ID NO: 81) | complex binding | | | | |
| X12 library vs. RSVB-IZN45 target | | | | | | | |
| Synthesized peptide | MW (Da) | Sequence | Kd (μM) | IC50 (μM) | Subsequent compounds(s) made from peptide | Kd (μM) | IC50 (μM) |
| Ac-X12-G12-G | 1587.887 | Ac-KVWTIQKPLTLY-G-NH2 (SEQ ID NO: 82) | | | | | |
| Ac-X12-H11-G | 1558.876 | Ac-TMHHKVWLIPKA-G-NH2 (SEQ ID NO: 83) | | | | | |
| X12-31 | 1483.7 | ALTYTLPVPHWW-NH2 (SEQ ID NO: 84) | | | | | |
| X12-45-GK | 1569.7885 | ISLPTPTWWPST-GK-NH2 (SEQ ID NO: 85) | RSV-B/IZN45: 6 | | | | |
| Ac-X12-45-GK | 1611.821 | Ac-ISLPTPTWWPST-GK-NH2 (SEQ ID NO: 86) | RSV-B/IZN45: 23 | | | | |
| X12-45-GG | 1498.688 | ISLPTPTWWPST-GG-NH2 (SEQ ID NO: 87) | RSV-B/IZN45: 11 | | | | |
| Ac-X12-45-GG | 1540.699 | Ac-ISLPTPTWWPST-GG-NH2 (SEQ ID NO: 88) | RSV-B/IZN45: 25 | | | | |
| Ac-X12-45-GG (PEG6)K | 2004.0674 | Ac-ISLPTPTWWPST-GG(PEG6)K-NH2 (SEQ ID NO: 89) | RSV-B/IZN45: 20 | | ^Ac-X12-45-GG(PEG6)K-trimer | RSV-B/IZN45: 0.066 RSV-A/IZN45: 0.053 | |
| Ac-X12-45-GG (PEG6)K scram | 2004.0674 | Ac-TWLPWTISPTPSGG-(PEG6)-K-NH2 (SEQ ID NO: 90) | | | | | |
| Ac-K(PEG6) GG-X12-45 | 2004.3 | Ac-K(PEG6)GG-ISLPTPTWWPST-NH2 (SEQ ID NO: 91) | | | ^Ac-K(PEG6)GG-X12-45-trimer | | |
| X12-47 | 1497.768 | SKVILPEPFWWP-NH2 (SEQ ID NO: 92) | RSV-B/IZN45: 10 | | | | |
| Ac-X12-47 | 1539.802 | Ac-SKVILPEPFWWP-NH2 (SEQ ID NO: 93) | | | | | |
| X12-47-GG | 1611.895 | SKVILPEPFWWP-GG-NH2 (SEQ ID NO: 94) | RSV-B/IZN45: 17 | | | | |

TABLE 7-continued

RSV D-peptides tested by SPR for ($K_D$) or syncytia reduction assay ($IC_{50}$)

| | | | | | |
|---|---|---|---|---|---|
| Ac-X12-47-GG | 1653.906 | Ac-SKVILPEPFWWP-GG-NH2 (SEQ ID NO: 95) | RSV-B/IZN45: 15 | | |
| Ac-X12-47-GG(PEG6)K | 2281.4844 | Ac-SK*VILPEPFWWP-GG(PEG6)K-NH2 (SEQ ID NO: 96) | | ^Ac-X12-47-GG(PEG6)K-trimer | RSV-B/IZN45: 0.088 RSV-A/IZN45: 0.076 |
| RSVP1-G(PEG6)K | 2080.4 | RWFELPEPDWW-G(PEG6)K-NH2 (SEQ ID NO: 97) | RSV-A/IZN45: 1.0 | RSVP1-G(PEG6)K-trimer | |
| RSVP1-G(PEG6)-Tricasso | 6193.45 | [RWFELPEPDWW-G(PEG6)]-K[peptide]-GK[peptide]-G-NH2, wherein the peptide monomers are each: RWFELPEPDWW-G(PEG6) (SEQ ID NO: 98) | | | |
| RSVP1-GK(PEG6)-Tricasso | 6578.2 | [RWFELPEPDWW-GK(PEG6)]-K[peptide]-GK[peptide]-G-NH2, wherein the peptide monomers are each RWFELPEPDWW-GK(PEG6) (SEQ ID NO: 99) | RSV-A/IZN45: ~0.02 | | |
| KG-RSVP1-G(PEG6)-Tricasso | 6749.4 | [KG-RWFELPEPDWW-G(PEG6)]-K[peptide]-GK[peptide]-G-NH2, wherein the peptide monomers are each KG-RWFELPEPDWW-G(PEG6) (SEQ ID NO: 100) | RSV-A/IZN45: ~0.02 | | |
| RSVP3-G(PEG6)-Tricasso | 6088.3 | [SWFYLPEPDWW-G(PEG6)]-K[peptide]-GK[peptide]-G-NH2, wherein the peptide monomers are each SWFYLPEPDWW-G(PEG6) (SEQ ID NO: 101) | | | |
| KG-RSVP3-G(PEG6)-Tricasso | 6644.2 | [KG-SWFYLPEPDWWG-(PEG6)]-K[peptide]-GK[peptide]-G-NH2, wherein the peptide monomers are each KG-SWFYLPEPDWWG-(PEG6) (SEQ ID NO: 102) | No inhibition | | |
| RSVP4-G(PEG6)-Tricasso | 6212.1 | [KYFWLPEPDWW-G(PEG6)]-K[peptide]-GK[peptide]-G-NH2, wherein the peptide monomers are each KYFWLPEPDWW-G(PEG6) (SEQ ID NO: 103) | | | |
| RSVP5-G(PEG6)-Tricasso | 6337 | [EWFYLPEPRWW-G(PEG6)]-K[peptide]-GK[peptide]-G-NH2, wherein the peptide monomers are each EWFYLPEPRWW-G(PEG6) (SEQ ID NO: 104) | | | |

TABLE 7-continued

RSV D-peptides tested by SPR for ($K_D$) or syncytia reduction assay ($IC_{50}$)

| | | | | |
|---|---|---|---|---|
| RSVP6-G(PEG6)-Tricasso | 6208.5 | [QWYFLPEPNWW-G(PEG6)]-K[peptide]-GK[peptide]-G-NH2, wherein the peptide monomers are each QWYFLPEPNWW-G(PEG6) (SEQ ID NO: 105) | | |
| KG-RSVP7-G(PEG6)-Tricasso | 6791.4 | [KG-RWFELPEPEWW-G(PEG6)]-K[peptide]-GK[peptide]-G-NH2, wherein the peptide monomers are each KG-RWFELPEPEWW-G(PEG6) (SEQ ID NO: 106) | RSV-A/IZN45: ~0.02 | 18.4 |
| KKG-RSVP7-G(PEG6)-Tricasso | 7172.55 | [KKG-RWFELPEPEWW-G(PEG6)]-K[peptide]-GK[peptide]-G-NH2, wherein the peptide monomers are each KKG-RWFELPEPEWW-G(PEG6) (SEQ ID NO: 107) | RSV-B/IZN45: 0.0036 RSV-A/IZN45: 0.0016 | 4.5, 4.8 |
| Ac-KG-RSVP7-G(PEG6)-Tricasso | 6912.4 | [Ac-KG-RWFELPEPEWWG(PEG6)]-K[peptide]-GK[peptide]-G-NH2, wherein the peptide monomers are each Ac-KG-RWFELPEPEWWG(PEG6) (SEQ ID NO: 108) | | |
| Ac-RSVP7-G(PEG6)K | 2135.3 | Ac-RWFELPEPEWWG-(PEG6)K-NH2 (SEQ ID NO: 109) | | Ac-RSVP7-G(PEG6)K-trimer |
| Ac-KG-RSVP7-G(PEG6)K | 2484.6 | Ac-K*G-RWFELPEPEWWG-(PEG6)K-NH2 (SEQ ID NO: 110) | | |
| RRG-RSVP7-G(PEG6)K | 2462.51 | RRG-RWFELPEPEWW-G(PEG6)K-NH2 (SEQ ID NO: 111) | | |
| KKGAAAA-RSVP7-G(PEG6)-Tricasso | 8024.9 | [KKGAAAA-RWFELPEPEWW-G(PEG6)]-K[peptide]-GK[peptide]-G-NH2, wherein the peptide monomers are each KKGAAAA-RWFELPEPEWW-G(PEG6) (SEQ ID NO: 112) | | 13.9, 7.4 |

Consensus-constrained X11 library vs. RSVB-IZN45 target

| Synthesized peptide | MW (Da) | Sequence | Kd (uM) | IC50 (uM) | Subsequent compounds(s) made from peptide | Kd (uM) | IC50 (uM) |
|---|---|---|---|---|---|---|---|
| Ac-RRG-RSVP11-G(PEG6)K | 3311.6634 | Ac-RRG-VDHRWQRWFELPDPEWW-G(PEG6)K-NH2 (SEQ ID NO: 113) | | | Ac-RRG-RSVP11-G(PEG6)K-trimer | | |
| Ac-RRRRG-RSVP11-G(PEG6)K | 3623.8654 | Ac-RRRRG-VDHRWQRWFELPDPEWW-G(PEG6)K-NH2 (SEQ ID NO: 114) | | | Ac-RRRRG-RSVP11-G(PEG6)K-trimer | No inhibition | |

TABLE 7-continued

*RSV D-peptides tested by SPR for ($K_D$) or syncytia reduction assay ($IC_{50}$)*

CX10C library vs. RSVB-IZN45 target

| Synthesized peptide | MW (Da) | Sequence | Kd (uM) | IC50 (uM) | Subsequent compounds(s) made from peptide | Kd (uM) | IC50 (uM) |
|---|---|---|---|---|---|---|---|
| CX10C-86-GK | 1910.12 | GACHTWDLNHLDVCAA-GK-NH2 (SEQ ID NO: 115) | RSV-B/IZN45: 350 | | | | |
| Ac-CX10C-86-GK | 1952.167 | Ac-GACHTWDLNHLDVCAA-GK-NH2 (SEQ ID NO: 116) | | | | | |
| CX10C-119 | 1823.0446 | GACKIHDLFHWHDCAA-NH2 (SEQ ID NO: 117) | RSV-B/IZN45: 100 | | | | |
| Ac-CX10C-119 | 1865.091 | Ac-GACKIHDLFHWHDCAA-NH2 (SEQ ID NO: 118) | RSV-B/IZN45: 280 | | | | |
| CX10C-119-GG | 1937.184 | GACKIHDLFHWHDCAA-GG-NH2 (SEQ ID NO: 119) | RSV-B/IZN45: 130 | | | | |
| Ac-CX10C-119-GG | 1979.195 | Ac-GACKIHDLFHWHDCAA-GG-NH2 (SEQ ID NO: 120) | RSV-B/IZN45: 30 | | | | |
| Ac-CX10C-119-GG(PEG6)K | 2606.7734 | Ac-GACK*IHDLFHWHDCAA-GG(PEG6)K-NH2 (SEQ ID NO: 121) | | | | | |

CX10C library vs. RSVB-IZN21 target

| Synthesized peptide | MW (Da) | Sequence | Kd (uM) | IC50 (uM) | Subsequent compounds(s) made from peptide | Kd (uM) | IC50 (uM) |
|---|---|---|---|---|---|---|---|
| KKG-RSVP20-Tricasso | 7800.882 | [KKG-GACRNEPHWLLDWCAA-(PEG6)]-K[peptide]-GK[peptide]-G-NH2, wherein the peptide monomers are each KKG-GACRNEPHWLLDWCAA-(PEG6) (SEQ ID NO: 122) | No binding main peak | | | | |
| Ac-KG-RSVP20 | 2066.946 | Ac-KG-GACRNEPHWLLDWCAA-NH2 (SEQ ID NO: 123) | | 673 | | | |
| Ac-K(PEG6)-RSVP20 | 2345.1184 | Ac-K(PEG6)-GACRNEPHWLLDWCAA-NH2 (SEQ ID NO: 124) | RSV-B/IZN45: 4.1 RSV-A/IZN45: 3.7 | | Ac-K(PEG6)-RSVP20-trimer | RSV-B/IZN45: 0.0017 RSV-A/IZN45: 0.0003 | 55, 19 |
| | | | | | Chol-Ac-K(PEG6)-RSVP20-trimer | | 7.9 |

TABLE 7-continued

RSV D-peptides tested by SPR for ($K_D$) or syncytia reduction assay ($IC_{50}$)

| Synthesized peptide | MW (Da) | Sequence | Kd (uM) | IC50 (uM) | Subsequent compounds(s) made from peptide | Kd (uM) | IC50 (uM) |
|---|---|---|---|---|---|---|---|
| KKG-RSVP21-Tricasso | 7614.801 | [KKG-GACTNRAEWLIDWCAA-(PEG6)]-K[peptide]-GK[peptide]-G-NH2, wherein each of the peptide monomers is KKG-GACTNRAEWLIDWCAA-(PEG6) (SEQ ID NO: 125) | No binding main peak | | | | |
| Ac-K(PEG6)-RSVP21 | 2283.0914 | Ac-K(PEG6)-GACTNRAEWLIDWCAA-NH2 (SEQ ID NO: 126) | RSV-B/IZN45: 12.0 RSV-A/IZN45: 2.8 | | Ac-K(PEG6)-RSVP21-trimer | RSV-B/IZN45: 0.0018 RSV-A/IZN45: 0.0003 | 65 |
| Ac-K(PEG6)-RSVP22 | 2438.1294 | Ac-K(PEG6)-GACKQRTEWYFDWCAA-NH2 (SEQ ID NO: 127) | No binding | | | | |

Consensus-constrained CX10C library vs. RSVB-IZN21 target

| Synthesized peptide | MW (Da) | Sequence | Kd (uM) | IC50 (uM) | Subsequent compounds(s) made from peptide | Kd (uM) | IC50 (uM) |
|---|---|---|---|---|---|---|---|
| Ac-K(PEG6)DDG-RSVP24 | 2700.2144 | Ac-K(PEG6)DDG-SMCVNRPEWLLDWCGT-NH2 (SEQ ID NO: 128) | RSV-B/IZN45: 1.8 RSV-A/IZN45: 2.1 | | Ac-K(PEG6)DDG-RSVP24-trimer | | 5.5 |
| | | | | | Chol-Ac-K(PEG6)DDG-RSVP24-trimer | | 0.24, 0.06 |
| Ac-RSVP24-GDD(PEG6)K | 2700.2144 | Ac-SMCVNRPEWLLDWCGT-GDD(PEG6)K-NH2 (SEQ ID NO: 129) | RSV-B/IZN45: 7.2 RSV-A/IZN45: 6.8 | | Ac-RSVP24-GDD(PEG6)K-trimer | | 4.6 |
| | | | | | Chol-Ac-RSVP24-GDD(PEG6)K-trimer | | 0.097 |
| Ac-K(PEG6)RRG-RSVP24 | 2782.3644 | Ac-K(PEG6)RRG-SMCVNRPEWLLDWCGT-NH2 (SEQ ID NO: 130) | | | Ac-K(PEG6)RRG-RSVP24-trimer | | |
| Ac-K(PEG6)DDG-RSVP25 | 2819.2644 | Ac-K(PEG6)DDG-EDCVNRSYWLLDWCNI-NH2 (SEQ ID NO: 131) | | | Ac-K(PEG6)DDG-RSVP25-trimer | | |
| Ac-K(PEG6)DDG-RSVP26 | 2745.2944 | Ac-K(PEG6)DDG-HACVNRPEWLLDWCGR-NH2 (SEQ ID NO: 132) | RSV-B/IZN45: ~15.5 RSV-A/IZN45: ~9.4 | | Chol-Ac-K(PEG6)DDG-RSVP26-trimer | | 3.2 |
| Ac-K(PEG6)G-RSVP26-GRR | 2884.4594 | Ac-K(PEG6)G-HACVNRPEWLLDWCGR-GRR-NH2 (SEQ ID NO: 133) | | | Ac-K(PEG6)G-RSVP26-GRR-trimer | | 5.5 |
| | | | | | Chol-Ac-K(PEG6)G-RSVP26-GRR-trimer | | 0.49 |

TABLE 7-continued

RSV D-peptides tested by SPR for (K$_D$)
or syncytia reduction assay (IC$_{50}$)

| | | | | | |
|---|---|---|---|---|---|
| Ac-K(PEG6)G-RSVP26-GRRRR | 3196.6614 | Ac-K(PEG6)G-HACVNRPEWLLDWCGR-GRRRR-NH2 (SEQ ID NO: 134) | | Ac-K(PEG6)G-RSVP26-GRRRR-trimer | |
| Ac-K(PEG6)DDG-RSVP27 | 2856.3 | Ac-K(PEG6)DDG-HECVNRPEWLLDWCEH-NH2 (SEQ ID NO: 135) | | Chol-Ac-K(PEG6)DDG-RSVP27-trimer | 0.14, 0.09, 0.088 |
| Ac-K(PEG6)DDG-RSVP28 | 2784.2944 | Ac-K(PEG6)DDG-HACVNRPEWLLDWCDH-NH2 (SEQ ID NO: 136) | RSV-B/IZN45: 2.9 RSV-A/IZN45: 5.0 | Chol-Ac-K(PEG6)DDG-RSVP28-trimer | 0.24 |
| Ac-K(PEG6)DDG-RSVP29 | 2640.1944 | Ac-K(PEG6)DDG-SACVNRPEWLLDWCGT-NH2 (SEQ ID NO: 137) | RSV-B/IZN45: 4.2 RSV-A/IZN45: 3.6 | Chol-Ac-K(PEG6)DDG-RSVP29-trimer | 0.12, 0.1 |
| Ac-K(PEG6)DDG-RSVP30 | 2656.2 | Ac-K(PEG6)DDG-SSCVNRPEWLLDWCGT-NH2 (SEQ ID NO: 138) | | Chol-Ac-K(PEG6)DDG-RSVP30-trimer | 0.47, 0.12 |
| Ac-K(PEG6)DDG-RSVP31 | 2684.2 | Ac-K(PEG6)DDG-AECVNRPEWLLDWCGT-NH2 (SEQ ID NO: 139) | | Chol-Ac-K(PEG6)DDG-RSVP31-trimer | 0.065, 0.054, 0.024 |
| Ac-K(PEG6)DDG-RSVP32 | 2668.2 | Ac-K(PEG6)DDG-GECVNRPEWLLDWCGT-NH2 (SEQ ID NO: 140) | | Chol-Ac-K(PEG6)DDG-RSVP32-trimer | 0.047, 0.052, 0.039, 0.013, 0.007 |
| Ac-RSVP32 | 1917.839 | Ac-GECVNRPEWLLDWCGT-NH2 (SEQ ID NO: 141) | | Ac-RSVP32 | |
| Ac-K(PEG4)DDG-RSVP32 | 2580.14 | Ac-K(PEG4)DDG-GECVNRPEWLLDWCGT-NH2 (SEQ ID NO: 142) | | Chol-Ac-K(PEG4)DDG-RSVP32-trimer | 0.028, 0.016, 0.011 |
| Ac-K(PEG8)G-RSVP32-GDD | 2813.35 | Ac-K(PEG8)G-GECVNRPEWLLDWCGT-GDD-NH2 (SEQ ID NO: 143) | | Chol-Ac-K(PEG8)G-RSVP32-GDD-trimer | 0.024, 0.008 |
| Ac-RSVP32-GDD(PEG6)K | 2668.1944 | Ac-GECVNRPEWLLDWCGT-GDD(PEG6)K-NH2 (SEQ ID NO: 144) | | Chol-Ac-RSVP32-GDD(PEG6)K-trimer | 0.009, 0.006, 0.044 |
| Ac-RSVP32-GDD(PEG4)K | 2580.14 | Ac-GECVNRPEWLLDWCGT-GDD(PEG4)K-NH2 (SEQ ID NO: 145) | | Chol-Ac-RSVP32-GDD(PEG4)K-trimer | 0.037, 0.052, 0.095 |
| Ac-DDG-RSVP32-G(PEG8)K | 2813.35 | Ac-DDG-GECVNRPEWLLDWCGT-G(PEG8)K-NH2 (SEQ ID NO: 146) | | Chol-Ac-DDG-RSVP32-G(PEG8)K-trimer | ? |
| Ac-K(P4)-EEG-RSVP32 | 2608.2 | Ac-K(PEG4)-EEG-GECVNRPEWLLDWCGT-NH2 (SEQ ID NO: 214) | | Chol-Ac-K(PEG4)EEG-RSVP32-trimer | 0.010. 0.026, 0.053, 0.062 |

TABLE 7-continued

RSV D-peptides tested by SPR for ($K_D$) or syncytia reduction assay ($IC_{50}$)

| | | | | |
|---|---|---|---|---|
| Ac-K(P6)-E-RSVP32 | 2510.2 | Ac-K(PEG6)-E-GECVNRPEWLLDWCGT-NH2 (SEQ ID NO: 215) | Chol-Ac-K(PEG6)E-RSVP32-trimer | 0.030, 0.052, 0.065, 0.024 |
| PEG8-RSVP32 | 2299.1 | (PEG8)-GECVNRPEWLLDWCGT-NH2 (SEQ ID NO: 216) | Chol-(PEG8)-RSVP32-trimer | 0.106, 0.055, 0.098, 0.133 |

"Ac" indicates capping at N-terminal with acetyl group

"NH2" indicates capping at C-terminus with an amide group

"BiotinPEG2" = N-Biotinyl-NH-(PEG)$_2$-COOH DIPEA (20 atoms), EMD Millipore Catalog #851029

"Glu(biotinyl-PEG)" = Fmoc-Glu(Biotinyl-PEG)-OH, EMD Millipore Catalog #852102

Peptides are cross-linked to the PEG scaffolds (for trimerization) via the unique primary amine (epsilon amino group of Lysine sidechain)

$K_D$ determined by SPR $IC_{50}$ determined by syncytia reduction assay using RSV-A F protein K* = lysine with DDE protecting group "(PEGN)" indicates insertion of PEGN by linking of PEGN to the C-terminus of the preceding amino acid and to the N-terminus of the following amino acid "Peptide" indicates conjugation to the same peptide as disclosed within brackets, to form a homotrimer In Table 7, "^" indicates a trimer having the following structure:

In Table 7, unmarked trimers have the following structure:

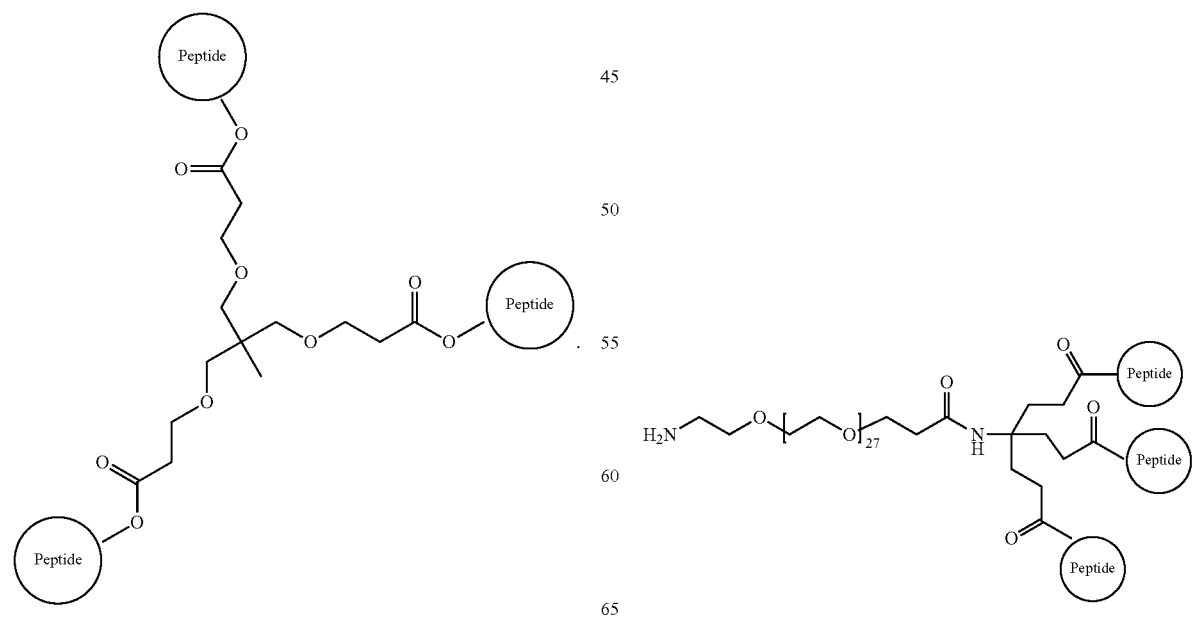

In Table 7, cholesterated trimers have the following structure:

[Chemical structure diagram: cholesterol moiety connected via carbamate to ethylene glycol linker -NH-CH2CH2-O-(CH2CH2O)3-CH2CH2-C(O)-NH-CH2CH2-O-(CH2CH2O)27-CH2CH2-C(O)-NH- attached to a trimer scaffold bearing three Peptide groups via carbonyl linkages]

Example 5

High Resolution Co-Crystal Structures

Figure 11:
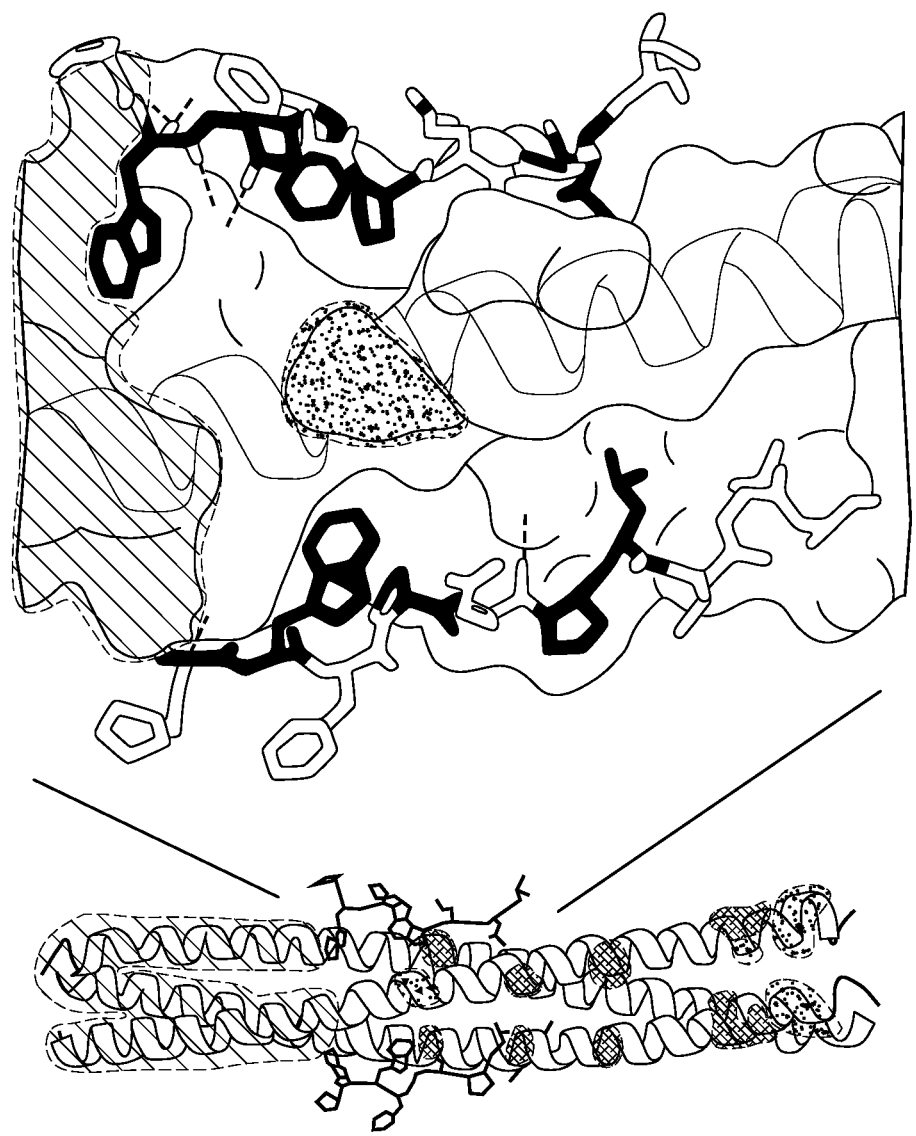
FIG. 11 depicts the crystal structure of X12-47 D-peptide bound to the RSV N-trimer. An overview of the structure is shown on the left. IZN45 monomers are continuous helices that form a coiled-coil. The IZ domain is shaded with a diagonal pattern. Non-conserved residues between RSV-A and B are shown in a grey speckled shading and the engineered mutations in IZN45_Mut are shown with cross-hatched shading. Two X12-47 monomers are shown as cartoons with side chains shown as sticks. On the right is a zoomed-in view with IZN45 rendered as a partially transparent surface. Like RSV C-peptides, X12-47 binds in the grooves of the N-trimer. The residues that make up the consensus sequence are colored black and the non-consensus residues are white. Four hydrogen bonds, including a water-mediated H-bond, between X12-47 and IZN45 are shown as dashed dark gray lines.
Figure 12:
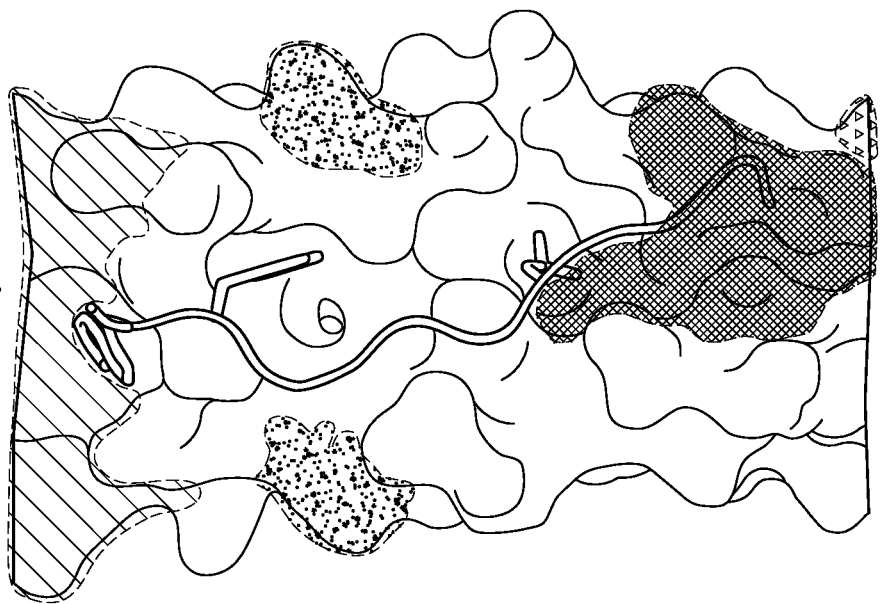
FIG. 12 depicts the crystal structure of RSV C-peptide bound to the RSV N-trimer (left) compared with the crystal structure of X12-47 D-peptide from the X12 library bound to IZN45 (right).
Figure 12:
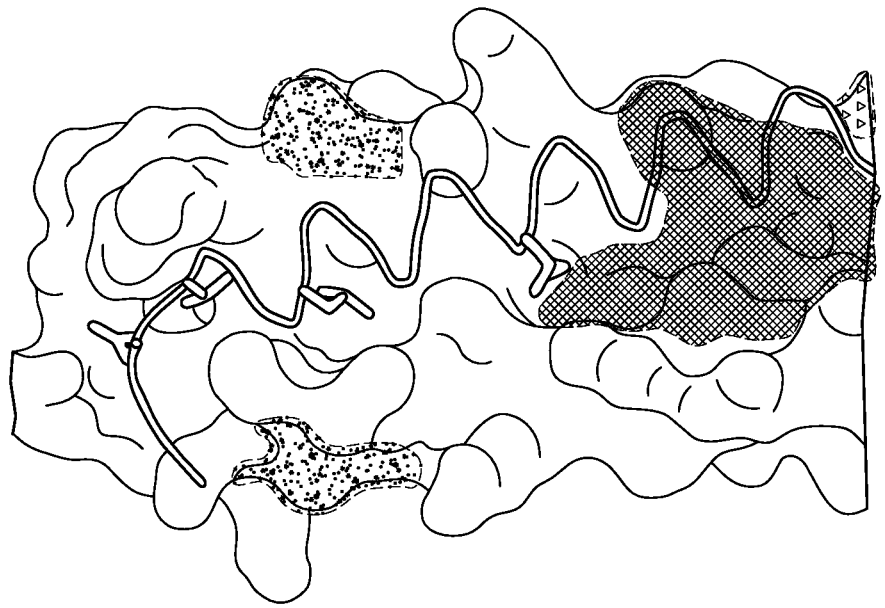

Another step in characterizing RSV D-peptide inhibitors is to crystallize a complex of a D-peptide inhibitor with the L-version of an RSV N-trimer mimic and solve the high resolution structure. The X-ray crystal structure of 'winning' peptide from the X12 library RSV D-peptide inhibitor X12-47 (SEQ ID NO:10) bound to RSVB-IZN45 N-trimer mimic (SEQ ID NO: 38) is shown in FIG. 11. As predicted from the phage ELISA data using mutated targets, X12-47 binds to the upper portion of N45 in the groove occupied by the C-peptide in the post-fusion trimer-of-hairpins structure (see, FIG. 11). The residues that comprise the consensus sequence are buried at the N-trimer interface and four intermolecular hydrogen bonds contribute to the strength and specificity of the interaction. The structure provides valuable insight for consensus-constrained secondary library design, target selection, and trimerization optimization. A comparison of the crystal structure of the natural RSV C-peptide bound to RSV N-trimer with the X12-47 D-peptide bound to RSVB-IZN45 shows similarities in binding, but the differences are difficult to predict (see, FIG. 12).

Figure 13:
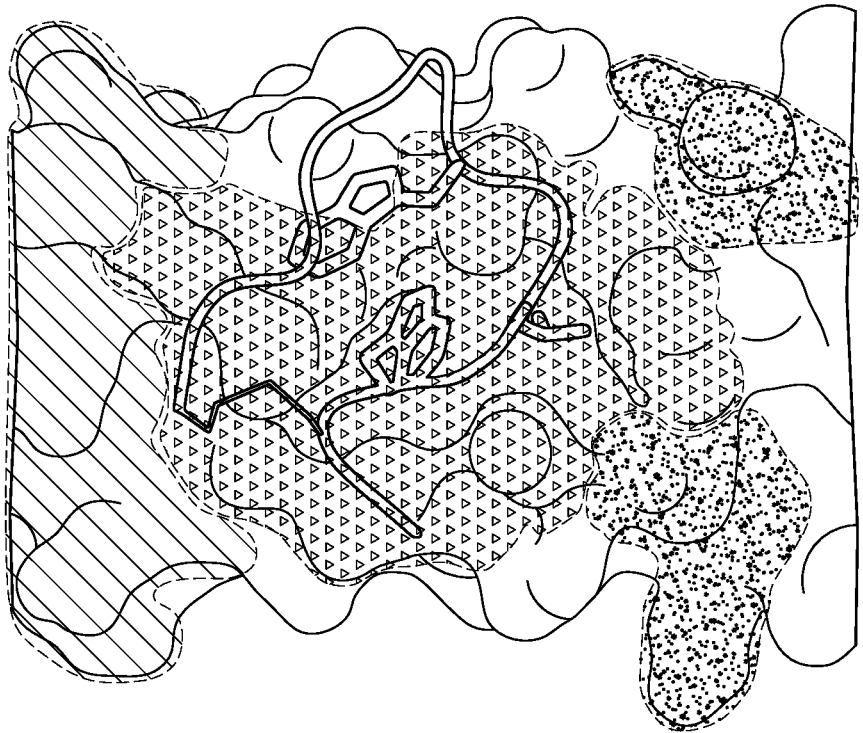
FIG. 13 depicts the crystal structure of RSV C-peptide bound to the RSV N-trimer (left) compared with the crystal structure of RSV20 D-peptide CX10C library bound to IZN21 (right).
Figure 13:
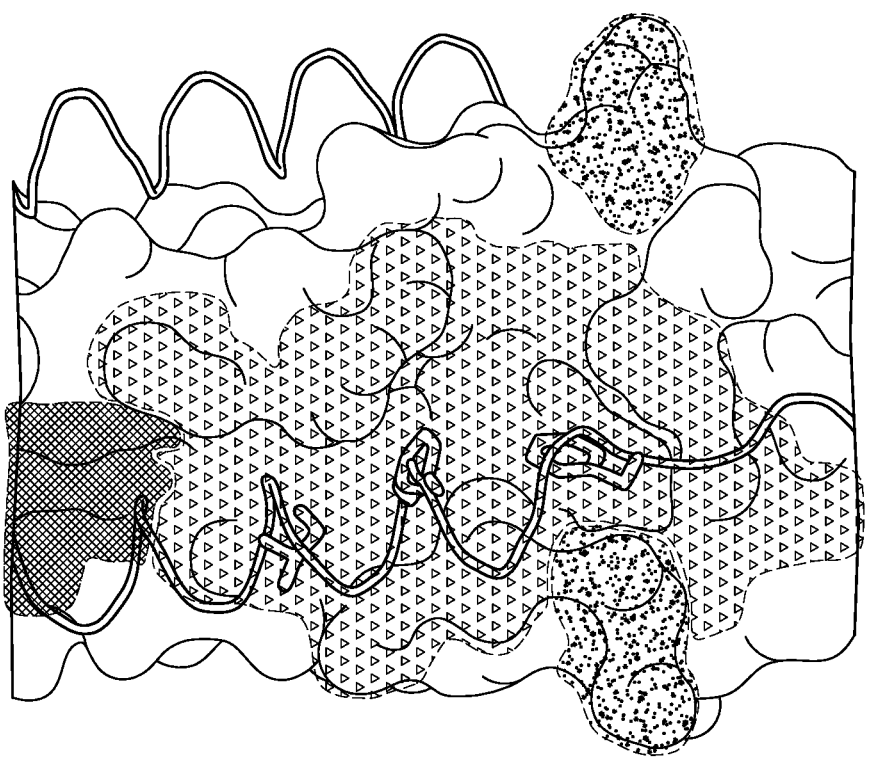

A comparison of the crystal structure of the natural RSV C-peptide bound to RSV N-trimer with RSVP20 D-peptide bound to RSVB IZN21 shows similarities in binding, but the differences are difficult to predict (see, FIG. 13).

Example 6

Further Anti-Viral Characterization of Optimized RSV D-Peptide Inhibitors

The ability of D-peptide trimers to prevent virus-induced cytotoxicity is tested in a cytopathic effect (CPE) reduction assay. MA-104 (embryonic African Green monkey cells) are infected with RSV in the absence (control) and presence of varying concentrations of the RSVP trimers. Cytotoxicity is scored both qualitatively by visual examination of cells and quantitatively by uptake of an extracellular red dye (neutral red, NR) by live cells to calculate an effective concentration ($EC_{50}$). Inhibitor-caused cytotoxicity is simultaneously measured on uninfected controls and a cytotoxicity score ($CC_{50}$) reported. The specificity index (SI) of each inhibitor is the $CC_{50}/EC_{50}$ ratio.

A virus yield reduction assay is used to measure the ability of D-peptide trimers to prevent viral replication. In brief, dilutions of the supernatant from the CPE reduction assay to infect fresh cell monolayers, and uptake of neutral red by the cells is used to titer the produced virus.

A syncytia reduction assay is used to measure the ability of D-peptide trimers to prevent cell-cell fusion of infected cells. Cells are infected with 100 syncytium forming units of RSV for 1 hour at 37° C. Inhibitor or vehicle is then added, and the cells are stained after 4-5 to count syncytia.

Example 7

Molecular Modeling for Affinity Maturation of RSVP32

Ac-K-(PEG4)DDG-RSVP32 (SEQ ID NO:142) is an affinity matured RSV N-trimer binder identified from phage display and represents an optimized binding solution from a disulfide constrained CX10C (disulfide constrained 10-mer) library based on the 20 natural amino acids. However, peptides with strategic substitutions, especially with non-natural amino acids that cannot be tested with phage display may be capable of higher affinity (e.g., by engineering additional hydrogen bonds or van der Waals' interactions). Using the co-crystal structure of RSVP32 (SEQ ID NO:31) and RSVA-IZN21 (SEQ ID NO:34), a molecular-modeling suite (ICM-Pro, MolSoft LLC) was used to model various natural and non-natural amino acid substitutions and calculate binding energies. The following parameters were used to calculate binding energy: electrostatic boundary element energy, H-bonds, solvation energy estimated as surface tension, and side-chain entropy.

TABLE 8

RSVP32 modifications and effects of the modifications on calculated binding energy for binding to RSVA-IZN45 (SEQ ID NO: 34).

| Position | Substitution | Sequence | Rationale (IZN45 numbering) | Result |
| --- | --- | --- | --- | --- |
| 6 | HRG | Ac-GECVN(HRG)PEWLLDWCGT-NH2 (SEQ ID NO: 147) | To form an H-bond with Ser50 (positive charge) | Decreased potency 2.6-fold compared to RSVP32 (65 nM vs 25 nM) |
| 6 | ASU | Ac-GECVN(ASU)PEWLLDWCGT-NH2 (SEQ ID NO: 148) | To form an H-bond with Ser50 (negative charge) | Not tested |
| 6 | KCX | Ac-GECVN(KCX)PEWLLDWCGT-NH2 (SEQ ID NO: 149) | To form an H-bond with Ser50 (negative charge) | Not tested |
| 6 | HHK | Ac-GECVN(HHK)PEWLLDWCGT-NH2 (SEQ ID NO: 150) | To form an H-bond with Ser50 (positive charge) | Not tested |
| 6 | Gln | Ac-GECVNQPEWLLDWCGT-NH2 (SEQ ID NO: 151) | To form an H-bond with Ser54 | Decreased potency ~2-fold compared to RSVP32 (53 nM vs 25 nM) |
| 6 | Glu | Ac-GECVNEPEWLLDWCGT-NH2 (SEQ ID NO: 152) | To form an H-bond with Ser54 | Not tested |
| 6 | Lys | Ac-GECVNKPEWLLDWCGT-NH2 (SEQ ID NO: 153) | To form an H-bond with Ser54 | Not tested |
| 6 | UN1 | Ac-GECVNRP(UN1)WLLDWCGT-NH2 (SEQ ID NO: 154) | To form an H-bond with Ser54 | Not tested |
| 6 | CCS | Ac-GECVNRP(CCS)WLLDWCGT-NH2 (SEQ ID NO: 155) | To form an H-bond with Ser54 | Not tested |
| 8 | ASU | Ac-GECVNRP(ASU)WLLDWCGT-NH2 (SEQ ID NO: 156) | To form an H-bond with Ser54 | Not tested |
| 11 | HLE | Ac-GECVNRPEWL(HLE)DWCGT-NH2 (SEQ ID NO: 157) | To better fill a cavity in the binding pocket | Not tested |

TABLE 8-continued

RSVP32 modifications and effects of the
modifications on calculated binding energy
for binding to RSVA-IZN45 (SEQ ID NO: 34).

| Position | Substitution | Sequence | Rationale (IZN45 numbering) | Result |
|---|---|---|---|---|
| 11 | NLE | Ac-GECVNRPEWL(NLE)DWCGT-NH2 (SEQ ID NO: 158) | To better fill a cavity in the binding pocket | Not tested |
| multiple | Shortened disulfide | Ac-GEVCRPEWLLDWCGT-NH2 (SEQ ID NO: 159) | To rigidify the peptide (reduce entropy penalty upon binding) | Decreased potency 14.4-fold compared to RSVP32 (360 nM vs 25 nM) |

HRG = Homoarginine
ASU = Aminosuberic acid
KCX = Lysine Nz-carboxylic acid
HHK = 2,8-Diaminooctanoic acid
UN1 = 2-Aminoadipic acid, Homoglutamate
CCS = carboxymethylated cysteine
HLE = Homoleucine
NLE = Norlucine

Example 8

Identification of Additional RSV D-Peptide (RSVP) Inhibitors of RSV Entry Using Mirror-Image Phage Display with Phage Libraries N1 and N2

Two additional libraries, N1 and N2, were screened against both RSVB-IZN21 (SEQ ID NO:35) and RSVB-IZN45 (SEQ ID NO:38) using the methods described in Example 3. The results of the bioinformatics data generated from deep sequencing are summarized in two tables below. The N2 library selection against the IZN21 target did not result in identification of any RSVPs (results not shown). Table 9 shows the top three most abundant sequences observed after four rounds of phage display (the 'winning' sequences). Table 10 shows clusters of related sequences present in the top approximately 25 most abundant sequences observed. A consensus sequence is shown below each cluster and the theoretical diversity of the library that would be required in order to explore every possible sequence is also shown.

Given the diversity required, custom phage display libraries are prepared that are large enough to fully explore all of the diversity in each of the consensus sequences. The highest affinity binder from phage display libraries representing the consensus sequence (i.e., from consensus-constrained libraries) are identified and isolated.

TABLE 9

Top sequences by abundance after 4 rounds of selection.

| Library | Target | Top 3 most abundant sequences |
|---|---|---|
| N1 | IZN21 | HHCEGGLLHYWCDI* (SEQ ID NO: 217) |
| | | SHCYSTGYFHWCDQ* (SEQ ID NO: 167) |
| | | QHCINTGYFDWCEK* (SEQ ID NO: 168) |
| | IZN45 | RVCWDEEVTWRCFH* (SEQ ID NO: 218) |
| | | NHCPKDHWGWLCWD* (SEQ ID NO: 219) |
| | | IDCYSTGYFRWCDK* (SEQ ID NO: 173) |
| N2 | IZN45 | ALNKKDLEDLKKFYEWAG* (SEQ ID NO: 202) |
| | | AHQKIEEEFWKKLWEHSG* (SEQ ID NO: 207) |
| | | ALDKKDYEDLKKFWEWVG* (SEQ ID NO: 200) |

*Phage clones with these sequences were subsequently tested in phage clone binding assay

TABLE 10

Clusters of sequences and consensus sequences (underlined) from sequencing after each selection.

| Library | Target | Consensus seq. 1 | Consensus seq. 2 | Consensus seq. 3 |
|---|---|---|---|---|
| N1 | IZN21 | SHCYSTGYFHWCDQ* (SEQ ID NO: 167) QHCINTGYFDWCEK* (SEQ ID NO: 168) | AHCDYHWMLDWCNL* (SEQ ID NO: 178) SHCDTHWMLDWCPQ* (SEQ ID NO: 179) | QWCDWSHYWGKCGT (SEQ ID NO: 189) TFCDWSHYWGQCKI (SEQ ID NO: 190) |

TABLE 10-continued

Clusters of sequences and consensus sequences
(underlined) from sequencing after each selection.

| Library | Target | Consensus seq. 1 | Consensus seq. 2 | Consensus seq. 3 |
|---|---|---|---|---|
| | | HQCQVHGYFNW<br>CPT<br>(SEQ ID NO: 169)<br>DHCITTGYFKW<br>CDD<br>(SEQ ID NO: 170)<br>THCVSTGYFQW<br>CPY<br>(SEQ ID NO: 171)<br>DNCITTGYFHW<br>CDS<br>(SEQ ID NO: 172)<br>IDCYSTGYFRW<br>CDK*<br>(SEQ ID NO: 173)<br>ELCYTTGYFTW<br>CPQ<br>(SEQ ID NO: 174)<br>HACSVHGFFNW<br>CPE<br>(SEQ ID NO: 175)<br>VECYRTGYFQW<br>CKH<br>(SEQ ID NO: 176)<br>HACSVHGFFNW<br>CPE<br>(SEQ ID NO: 177)<br><u>XXCXXTGYFXW</u><br><u>CXX</u><br>(SEQ ID NO: 160)<br>Diversity = 1.3e9 | QHCEHWWFD<br>WCPE<br>(SEQ ID NO: 180)<br>EHCDLHWNFD<br>WCTV<br>(SEQ ID NO: 181)<br>SHCEMHWEMD<br>WCQK<br>(SEQ ID NO: 182)<br>YLCDPTWLLD<br>WCHT<br>(SEQ ID NO: 183)<br>VHCPFHWEMN<br>WCQS<br>(SEQ ID NO: 184)<br>GHCPYHWSLD<br>WCVD<br>(SEQ ID NO: 185)<br>DHCPMHWNFS<br>WCED<br>(SEQ ID NO: 186)<br>SHCPAHWLMD<br>WCVQ<br>(SEQ ID NO: 187)<br>NHCDLHWEMD<br>WCKS<br>(SEQ ID NO: 188)<br><u>XHCXXHWXXD</u><br><u>WCXX</u><br>(SEQ ID NO: 161)<br>Diversity = 1.3e9 | FYCDWSHYGG<br>QCKI<br>(SEQ ID NO: 191)<br><u>XXCDWSHYX</u><br><u>GCXX</u><br>(SEQ ID NO: 166)<br>Diversity = 3.2e6 |
| | IZN45 | IDCYSTGYFRW<br>CDK*<br>(SEQ ID NO: 192)<br>QHCINTGYFDW<br>CEK*<br>(SEQ ID NO: 193)<br>SHCYSTGYFHW<br>CDQ*<br>(SEQ ID NO: 194)<br><u>XXCXXTGYFXW</u><br><u>CXX</u><br>(SEQ ID NO: 162) | | |
| N2 | IZN45 | AMDKKFYEDLK<br>KFNEWWG<br>(SEQ ID NO: 195)<br>ALHKKDYEELK<br>KFYEWAG<br>(SEQ ID NO: 196)<br>ALHKKDYEELK<br>KFYEWAG<br>(SEQ ID NO: 197)<br>ALHKKDYEELK<br>KFHEWWG<br>(SEQ ID NO: 198)<br>ALDKKDMEDLK<br>KYWEWLG<br>(SEQ ID NO: 199)<br>ALDKKDYEDLK<br>KFWEWVG*<br>(SEQ ID NO: 200)<br>ALEKKDWEDLK<br>KFQEWWG<br>(SEQ ID NO: 201)<br>ALNKKDLEDLK<br>KFYEWAG*<br>(SEQ ID NO: 202)<br>ALNKKDHEDLK<br>KFYEWMG<br>(SEQ ID NO: 203)<br>ALNKKDYEDLK<br>KYYEWFG<br>(SEQ ID NO: 204) | AHEKTLLEWEK<br>KWLEHFG<br>(SEQ ID NO: 206)<br>AHQKIEEEFWK<br>KLWEHSG*<br>(SEQ ID NO: 207)<br>AHHKIEDEFWK<br>KVSEHWG<br>(SEQ ID NO: 208)<br>AHHKIQDEYWK<br>KVLEHVG<br>(SEQ ID NO: 209)<br><u>AHXKIXXEXWK</u><br><u>KXXEHXG</u><br>(SEQ ID NO: 164)<br>Diversity =1.3e9 | AWDKKETEFW<br>KKFEEFYG<br>(SEQ ID NO: 210)<br>AWDKKQVEDY<br>KKFYEIFG<br>(SEQ ID NO: 211)<br>AWDKKDWED<br>WKKFEETFG<br>(SEQ ID NO: 212)<br>AWDKKELEFW<br>KNYEEWYG*<br>(SEQ ID NO: 213)<br><u>AWDKKXXEXX</u><br><u>KKFXEXXG</u><br>(SEQ ID NO: 165)<br>Diversity = 1.3e9 |

TABLE 10-continued

Clusters of sequences and consensus sequences
(underlined) from sequencing after each selection.

| Library | Target | Consensus seq. 1 | Consensus seq. 2 | Consensus seq. 3 |
|---|---|---|---|---|
| | | ALTKKDAEDLK KFYEWFG (SEQ ID NO: 205) <u>ALXKKDXE(D/E) LKKFXEWXG</u> (SEQ ID NO: 163) Diversity = 3.2e5 | | |

Consensus residues are shown in bold
Consensus constrained library sequence is underlined
*Phage clones with these sequences were subsequently tested in phage clone binding assay
Each "X" in consensus sequences represents any of the 20 natural amino acids Phage clones representing the three most abundant sequences overall as well as the most abundant sequences in each unique cluster (present in the top approximately 25 most abundant sequences) were prepared. A phage clone binding assay was performed to validate phage binding as well as rank-order the best binders. Typically, the most abundant phage identified from the deep sequencing analysis are also the highest affinity binders in the phage clone binding assay (highest percent bound after washing). However, occasionally clones may be selected during phage display via mechanisms other than target binding (e.g., phage growth advantage). The phage clone binding assay mimics a round of phage display except purified clonal phage are used instead of a library containing many different phage. Therefore, the phage clone binding assay provides validation of target binding and removes elements of direct competition that may be present during the selection.

Briefly, an equal number of clonal phage were incubated separately with biotinylated target in solution. Streptavidin-coated magnetic beads were added to capture biotinylated target and bound phage from solution. The beads were immediately precipitated using a magnet, and the beads were washed several times. Phage bound to target was eluted after washing using acid to disrupt target binding. The phage were neutralized and quantified using a RT-PCR. The number of phage captured was compared to the total number of input phage in order to calculate the percent of phage bound. Two negative controls defined the background binding in this assay: 1) No target control—phage incubated with vehicle control instead of target; and 2) M13KE—a control phage with no library peptide displayed on its surface and used in place of library phage. As a positive control and reference, the RSVP31 phage clone was used. RSVP31 is an affinity-matured clone from the consensus-constrained CX10C library that has been validated by additional biochemical methods and cell-based assays.

Figure 17:
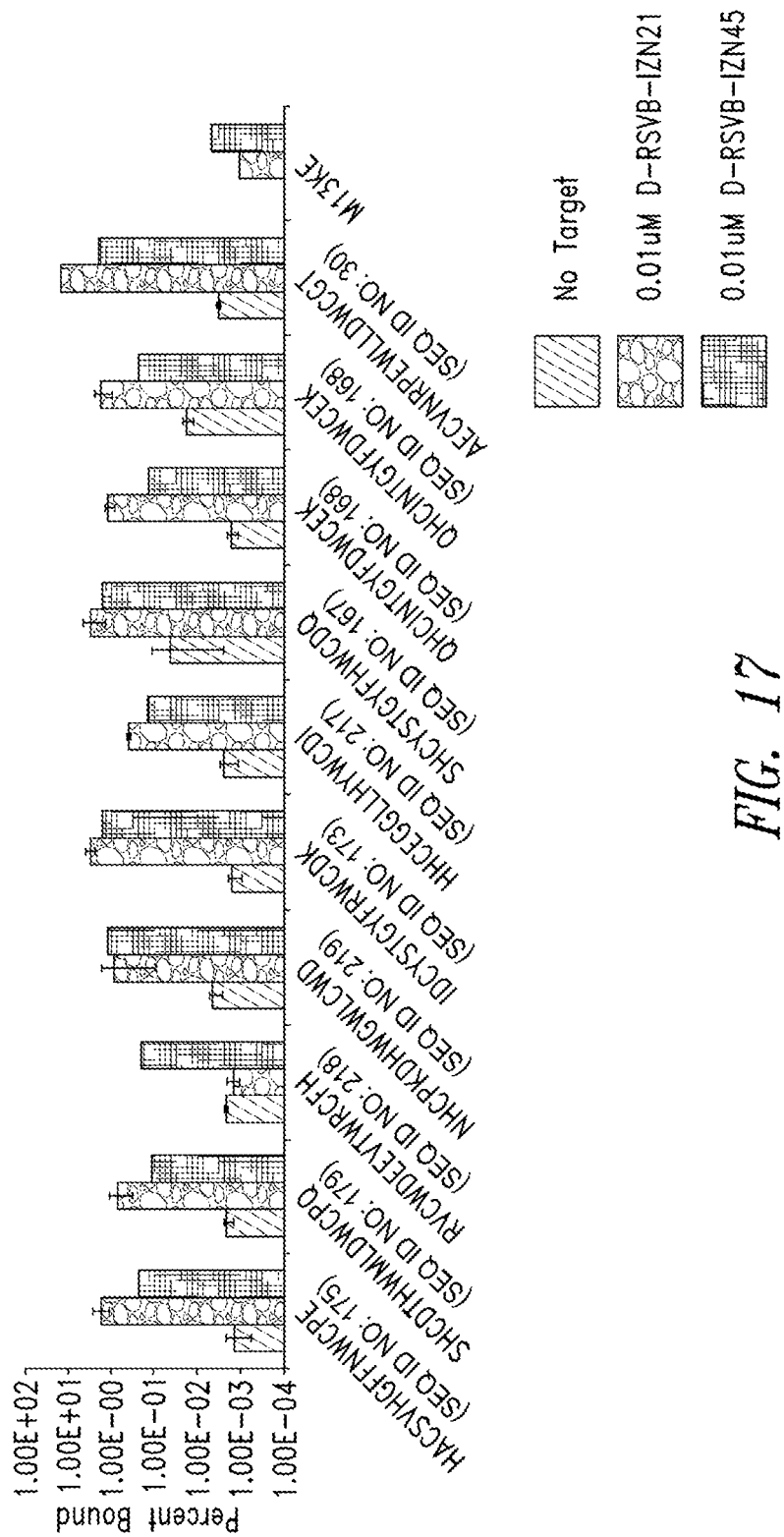
FIG. 17 depicts binding of phage clones to RSVB-IZN21 or RSVB-IZN45. The phage clones were identified in the mirror-image phage display using the N1 library and display the listed peptide (x-axis). Phage clones were incubated with IZN21, IZN45, or vehicle control (no target). M13KE phage was used as a control phage.
Figure 18:
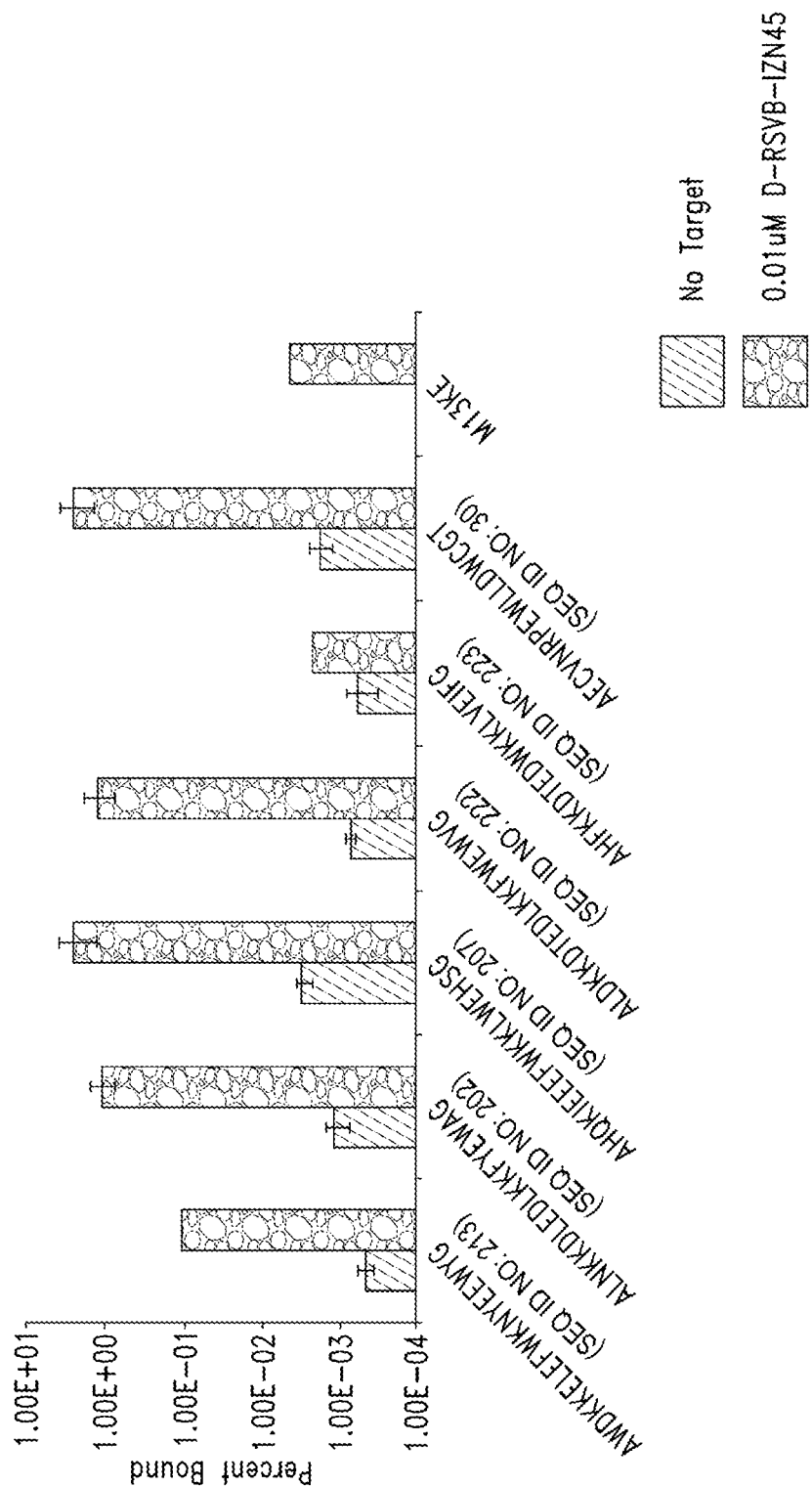
FIG. 18 depicts binding of phage clones to RSVB-IZN45. The phage clones were identified in the mirror-image phage display using the N2 library and display the listed peptide (x-axis). Phage clones were incubated with IZN45 or vehicle control (no target). M13KE phage was used as a control phage.

The results of the phage clone binding assay are shown in FIG. 17 (N1 library) and 18 (N2 library). RSVPs discovered from the naive N1 and N2 libraries performed as well or nearly as well as RSVP31 in this assay (both in terms of absolute binding and minimal background binding).

Consensus-constrained libraries based on consensus sequences shown in the tables above are used in further phase display screening to identify additional binders.

All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/211,625, are incorporated herein by reference, in their entirety.

The various embodiments described above can be combined to provide further embodiments. Aspects of the embodiments can be modified, if necessary to employ concepts of the various patents, applications and publications to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated D-peptide comprising the amino acid sequence of SEQ ID NO:42, wherein the amino acids of the D-peptide have a D-configuration with the exception of glycine and the D-peptide is capable of interacting with the N-trimer groove of respiratory syncytial virus (RSV) F protein.

2. The isolated D-peptide of claim 1, wherein the D-peptide is linked to an identical D-peptide.

3. The isolated D-peptide of claim 1, wherein the D-peptide is linked to two identical D-peptides.

4. The isolated D-peptide of claim 1, wherein the D-peptide comprises an amino acid sequence selected from any one of SEQ ID NOS:23-31, 122-124, 128-146, 214-216, 152, and 159.

5. The isolated D-peptide of claim 1, wherein the N-terminus of the D-peptide is capped with an acetyl group.

6. The isolated D-peptide of claim 1, wherein the C-terminus of the D-peptide is capped with an amide group.

7. An isolated composition comprising a first D-peptide comprising the amino acid sequence of SEQ ID NO:42, wherein the amino acids of the first D-peptide have a D-configuration with the exception of glycine and the first D-peptide is capable of interacting with the N-trimer groove of respiratory syncytial virus (RSV) F protein.

8. The isolated composition according to claim 7, wherein the first D-peptide is linked to a second D-peptide, wherein the amino acids of the second D-peptide have a D-configuration with the exception of glycine.

9. The isolated composition according to claim 8, wherein the second D-peptide is identical to the first D-peptide.

10. The isolated composition according to claim 7, wherein the first D-peptide is linked to a second D-peptide and a third D-peptide, wherein the amino acids of the third D-peptide have a D-configuration with the exception of glycine.

11. The isolated composition according to claim 10, wherein the first D-peptide, second D-peptide, and third D-peptide are identical.

12. The isolated composition according to claim 10, wherein the first D-peptide, the second D-peptide, and the third D-peptide, are multimerized through a cross-linker.

13. The isolated composition of claim 12, wherein the cross-linker is a polyethylene glycol (PEG) linker.

14. The isolated composition according to claim 12, wherein the N-termini of the D-peptides are cross-linked.

15. The isolated composition according to claim 12, wherein the C-termini of the D-peptides are cross-linked.

16. The isolated composition according to claim 12, wherein the N-terminus or C-terminus of each D-peptide is cross-linked.

17. The isolated composition according to claim 12, wherein the first D-peptide, the second D-peptide, and the third D-peptide, are multimerized through a scaffold having the following structure:

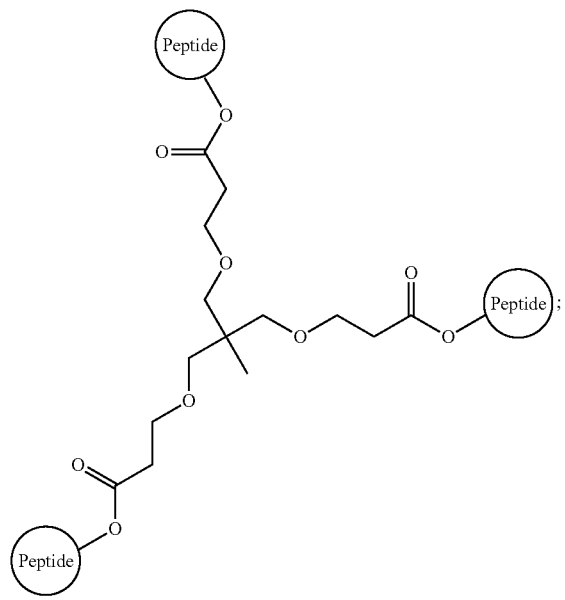
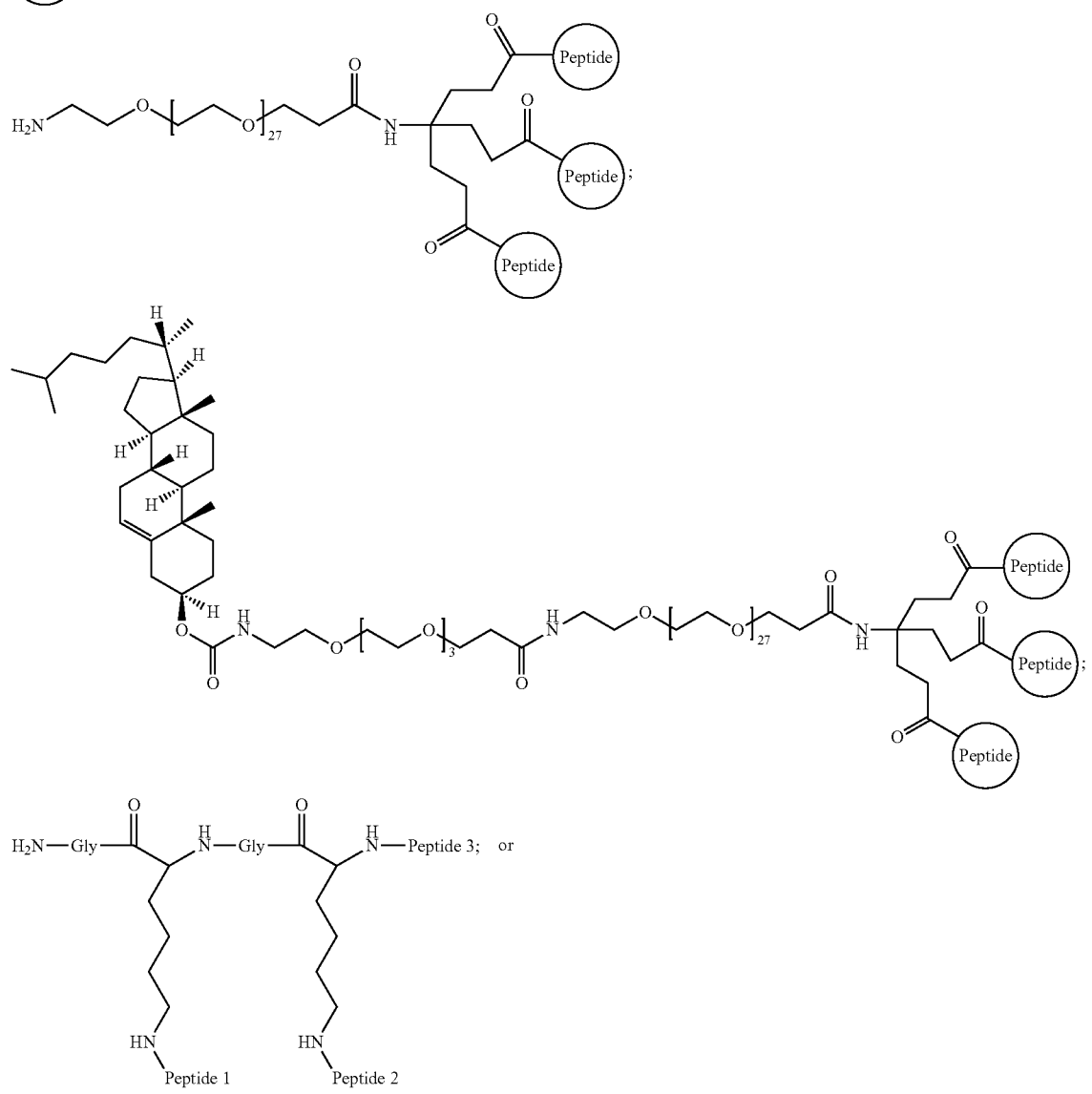

18. The isolated composition according to claim 17, wherein:
- the N-termini of the D-peptides are attached to the scaffold;
- the C-termini of the D-peptides are attached to the scaffold; or
- the N-terminus or C-terminus of each D-peptide is attached to the scaffold.

19. The isolated composition of claim 7, wherein the first D-peptide comprises an amino acid sequence selected from any one of SEQ ID NOS:23-31, 122-124, 128-146, 214-216, 152, and 159.

20. The isolated composition of claim 19, wherein the N-terminus of the D-peptide is capped with an acetyl group.

21. The isolated composition of claim 19, wherein the C-terminus of the D-peptide is capped with an amide group.

22. The isolated composition of claim 17, wherein:
- the first, second, and third D-peptide each comprises the amino acid sequence of Ac-K(PEG4)-DDG-GECVN-RPEWLLDWCGT-NH2 (SEQ ID NO:142); or
- the first, second, and third D-peptide each comprises the amino acid sequence of Ac-K(PEG4)-EEG-GECVN-RPEWLLDWCGT-NH2 (SEQ ID NO:214).

23. The isolated composition of claim 7, wherein the first D-peptide is linked to a potency enhancing cargo molecule.

24. The isolated composition of claim 23, wherein the potency enhancing cargo molecule is a cholesterol, sterol, sugar, maltose binding protein, ubiquitin, streptavidin, immunoglobulin domain, keyhole limpet hemacyanin, sperm whale myoovalbumin, bovine pancreatic trypsin inhibitor, green fluorescent protein, gold particle, magnetic particle, agarose bead, lactose bead, fatty acid, a high molecular weight PEG, or serum albumin.

25. The isolated composition of claim 23, wherein the potency enhancing cargo molecule is linked to the first D-peptide with a PEG linker.

26. The isolated composition according to claim 10, wherein a trimer of the first, second, and third D-peptides exhibits enhanced binding affinity or anti-viral activity as compared with the binding affinity or anti-viral activity of an isolated composition comprising the first D-peptide as a monomer.

27. The isolated composition according to claim 10, wherein the composition further comprises a pharmaceutically acceptable carrier.

28. A method for inhibiting entry of respiratory syncytial virus (RSV) into a host cell, comprising exposing the RSV virus to the D-peptide of claim 1, thereby inhibiting entry of the virus into the host cell.

29. The method according to claim 28, wherein the D-peptide comprises an amino acid sequence as set forth in SEQ ID NO:142 or SEQ ID NO:214.

30. A method for inhibiting entry of RSV into a host cell, comprising exposing the RSV virus to a composition comprising a first D-peptide, a second D-peptide, and a third D-peptide that are multimerized through a scaffold having the following structure:

wherein each of the first, second, and third D-peptides comprises an amino acid sequence as set forth in SEQ ID NO:142; or each of the first, second, and third D-peptides comprises an amino acid sequence as set forth in SEQ ID NO:214; and wherein the amino acids of the first, second, and third D-peptides have a D-configuration with the exception of glycine.

31. A method of treating respiratory syncytial virus (RSV) infection in a subject, comprising administering to the subject a therapeutically effective amount of the D-peptide of claim 1.

32. A method of treating RSV infection in a subject, comprising administering to the subject a therapeutically effective amount of a D-peptide according to claim 4.

33. A method of treating RSV infection in a subject comprising administering to the subject a therapeutically effective amount of a composition according to claim 22.

34. The method of claim 31, wherein the D-peptide w is administered concurrently or sequentially with at least one additional anti-viral agent.

35. The method of claim 34, wherein the at least one additional anti-viral agent is a viral fusion inhibitor, viral attachment inhibitor, viral replication inhibitor, a viral protease inhibitor, an inhibitor antibody, a biologic, an antisense molecule, an RNA interference agent, a peptide, or a small molecule.

36. The isolated D-peptide of claim 1, wherein the D-peptide is 8 to 30 amino acids in length.

\* \* \* \* \*

SEQUENCE LISTING

<160> NUMBER OF SEQ ID NOS: 229

<210> SEQ ID NO 1
<211> LENGTH: 7
<212> TYPE: PRT
<213> ORGANISM: Artificial Sequence
<220> FEATURE:
<223> OTHER INFORMATION: X12 Consensus Sequence
<220> FEATURE:
<221> NAME/KEY: VARIANT
<222> LOCATION: 3,5
<223> OTHER INFORMATION: Xaa = Gly or any of the other 19 natural amino
      acids in the D-configuration

<400> SEQUENCE: 1

```
Leu Pro Xaa Pro Xaa Trp Trp
1               5

<210> SEQ ID NO 2
<211> LENGTH: 8
<212> TYPE: PRT
<213> ORGANISM: Artificial Sequence
<220> FEATURE:
<223> OTHER INFORMATION: CX10C Consensus Sequence
<220> FEATURE:
<221> NAME/KEY: VARIANT
<222> LOCATION: 1
<223> OTHER INFORMATION: Xaa = Arg or Glu
<220> FEATURE:
<221> NAME/KEY: VARIANT
<222> LOCATION: 2
<223> OTHER INFORMATION: Xaa = Gly or any of the other 19 natural amino
      acids in the D-configuration
<220> FEATURE:
<221> NAME/KEY: VARIANT
<222> LOCATION: 3
<223> OTHER INFORMATION: Xaa = His, Glu or Tyr

<400> SEQUENCE: 2

Xaa Xaa Xaa Trp Leu Leu Asp Trp
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide X16-16

<400> SEQUENCE: 3

Asp Tyr Leu Pro Leu Pro Glu Pro Arg Trp Trp Phe Pro Glu Tyr Gln
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide X16-18

<400> SEQUENCE: 4

Ser Leu Lys Tyr Trp Trp Met Glu Glu Leu Pro Leu Pro Lys Trp Trp
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide X16-20

<400> SEQUENCE: 5

His Trp Leu Pro Leu Gln Pro Trp Trp Asp Asp Ile Pro Val Trp His
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide G12

<400> SEQUENCE: 6

Lys Val Trp Thr Ile Gln Lys Pro Leu Thr Leu Tyr
```

```
<210> SEQ ID NO 7
<211> LENGTH: 12
<212> TYPE: PRT
<213> ORGANISM: Artificial Sequence
<220> FEATURE:
<223> OTHER INFORMATION: Synthetic peptide H11

<400> SEQUENCE: 7

Thr Met His His Lys Val Trp Leu Ile Pro Lys Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide X12-31

<400> SEQUENCE: 8

Ala Leu Thr Tyr Thr Leu Pro Val Pro His Trp Trp
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide X12-45

<400> SEQUENCE: 9

Ile Ser Leu Pro Thr Pro Thr Trp Trp Pro Ser Thr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide X12-47

<400> SEQUENCE: 10

Ser Lys Val Ile Leu Pro Glu Pro Phe Trp Trp Pro
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide RSVP1

<400> SEQUENCE: 11

Arg Trp Phe Glu Leu Pro Glu Pro Asp Trp Trp
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide RSVP3

<400> SEQUENCE: 12

Ser Trp Phe Tyr Leu Pro Glu Pro Asp Trp Trp
1               5                   10
```

```
<210> SEQ ID NO 13
<211> LENGTH: 11
<212> TYPE: PRT
<213> ORGANISM: Artificial Sequence
<220> FEATURE:
<223> OTHER INFORMATION: Synthetic peptide RSVP4

<400> SEQUENCE: 13

Lys Tyr Phe Trp Leu Pro Glu Pro Asp Trp Trp
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide RSVP5

<400> SEQUENCE: 14

Glu Trp Phe Tyr Leu Pro Glu Pro Arg Trp Trp
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide RSVP6

<400> SEQUENCE: 15

Gln Trp Tyr Phe Leu Pro Glu Pro Asn Trp Trp
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide RSVP7

<400> SEQUENCE: 16

Arg Trp Phe Glu Leu Pro Glu Pro Glu Trp Trp
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Synthetic peptide RSVP11

<400> SEQUENCE: 17

Val Asp His Arg Trp Gln Arg Trp Phe Glu Leu Pro Asp Pro Glu Trp
1               5                   10                  15

Trp

<210> SEQ ID NO 18
<211> LENGTH: 16
<212> TYPE: PRT
<213> ORGANISM: Artificial Sequence
<220> FEATURE:
<223> OTHER INFORMATION: Synthetic peptide CXC10C-86

<400> SEQUENCE: 18

Gly Ala Cys His Thr Trp Asp Leu Asn His Leu Asp Val Cys Ala Ala
```

1 5 10 15

<210> SEQ ID NO 19
<211> LENGTH: 16
<212> TYPE: PRT
<213> ORGANISM: Artificial Sequence
<220> FEATURE:
<223> OTHER INFORMATION: Synthetic peptide CXC10C-119

<400> SEQUENCE: 19

Gly Ala Cys Lys Ile His Asp Leu Phe His Trp His Asp Cys Ala Ala
1 5 10 15

<210> SEQ ID NO 20
<211> LENGTH: 16
<212> TYPE: PRT
<213> ORGANISM: Artificial Sequence
<220> FEATURE:
<223> OTHER INFORMATION: Synthetic peptide RSVP20

<400> SEQUENCE: 20

Gly Ala Cys Arg Asn Glu Pro His Trp Leu Leu Asp Trp Cys Ala Ala
1 5 10 15

<210> SEQ ID NO 21
<211> LENGTH: 16
<212> TYPE: PRT
<213> ORGANISM: Artificial Sequence
<220> FEATURE:
<223> OTHER INFORMATION: Synthetic peptide RSVP21

<400> SEQUENCE: 21

Gly Ala Cys Thr Asn Arg Ala Glu Trp Leu Ile Asp Trp Cys Ala Ala
1 5 10 15

<210> SEQ ID NO 22
<211> LENGTH: 16
<212> TYPE: PRT
<213> ORGANISM: Artificial Sequence
<220> FEATURE:
<223> OTHER INFORMATION: Synthetic peptide RSVP22

<400> SEQUENCE: 22

Gly Ala Cys Lys Gln Arg Thr Glu Trp Tyr Phe Asp Trp Cys Ala Ala
1 5 10 15

<210> SEQ ID NO 23
<211> LENGTH: 16
<212> TYPE: PRT
<213> ORGANISM: Artificial Sequence
<220> FEATURE:
<223> OTHER INFORMATION: Synthetic peptide RSVP24

<400> SEQUENCE: 23

Ser Met Cys Val Asn Arg Pro Glu Trp Leu Leu Asp Trp Cys Gly Thr
1 5 10 15

<210> SEQ ID NO 24
<211> LENGTH: 16
<212> TYPE: PRT
<213> ORGANISM: Artificial Sequence
<220> FEATURE:
<223> OTHER INFORMATION: Synthetic peptide RSVP25

<400> SEQUENCE: 24

Glu Asp Cys Val Asn Arg Ser Tyr Trp Leu Leu Asp Trp Cys Asn Ile
1 5 10 15

<210> SEQ ID NO 25
<211> LENGTH: 16
<212> TYPE: PRT
<213> ORGANISM: Artificial Sequence
<220> FEATURE:
<223> OTHER INFORMATION: Synthetic peptide RSVP26

<400> SEQUENCE: 25

His Ala Cys Val Asn Arg Pro Glu Trp Leu Leu Asp Trp Cys Gly Arg
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic peptide RSVP27

<400> SEQUENCE: 26

His Glu Cys Val Asn Arg Pro Glu Trp Leu Leu Asp Trp Cys Glu His
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic peptide RSVP28

<400> SEQUENCE: 27

His Ala Cys Val Asn Arg Pro Glu Trp Leu Leu Asp Trp Cys Asp His
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic peptide RSVP29

<400> SEQUENCE: 28

Ser Ala Cys Val Asn Arg Pro Glu Trp Leu Leu Asp Trp Cys Gly Thr
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Synthetic peptide RSVP30

<400> SEQUENCE: 29

Ser Ser Cys Val Asn Arg Pro Glu Trp Leu Leu Asp Trp Cys Gly Thr
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Synthetic peptide RSVP31

<400> SEQUENCE: 30

Ala Glu Cys Val Asn Arg Pro Glu Trp Leu Leu Asp Trp Cys Gly Thr
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic peptide RSVP32

<400> SEQUENCE: 31

Gly Glu Cys Val Asn Arg Pro Glu Trp Leu Leu Asp Trp Cys Gly Thr
1               5                   10                  15

<210> SEQ ID NO 32
<211> LENGTH: 45
<212> TYPE: PRT
<213> ORGANISM: Artificial Sequence
<220> FEATURE:
<223> OTHER INFORMATION: Synthetic peptide RSVA-IZN18

<400> SEQUENCE: 32

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Glu Val Leu Thr Ser Lys
            20                  25                  30

Val Leu Asp Leu Lys Asn Tyr Ile Asp Lys Gln Leu Leu
        35                  40                  45

<210> SEQ ID NO 33
<211> LENGTH: 45
<212> TYPE: PRT
<213> ORGANISM: Artificial Sequence
<220> FEATURE:
<223> OTHER INFORMATION: Synthetic peptide RSVB-IZN18

<400> SEQUENCE: 33

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Glu Val Leu Thr Ser Lys
            20                  25                  30

Val Leu Asp Leu Lys Asn Tyr Ile Asn Asn Gln Leu Leu
        35                  40                  45

<210> SEQ ID NO 34
<211> LENGTH: 48
<212> TYPE: PRT
<213> ORGANISM: Artificial Sequence
<220> FEATURE:
<223> OTHER INFORMATION: Synthetic peptide RSVA-IZN21

<400> SEQUENCE: 34

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Glu Val Leu Thr Ser Lys
            20                  25                  30

Val Leu Asp Leu Lys Asn Tyr Ile Asp Lys Gln Leu Leu Pro Ile Val
        35                  40                  45

<210> SEQ ID NO 35
<211> LENGTH: 48
<212> TYPE: PRT
<213> ORGANISM: Artificial Sequence
<220> FEATURE:
<223> OTHER INFORMATION: Synthetic peptide RSVB-IZN21

<400> SEQUENCE: 35

```
Ile Lys Lys Glu Ile Glu Ala Ile Lys Glu Gln Glu Ala Ile Lys
1               5                   10                  15

Lys Lys Ile Glu Ala Ile Glu Lys Glu Ile Glu Val Leu Thr Ser Lys
            20                  25                  30

Val Leu Asp Leu Lys Asn Tyr Ile Asn Asn Gln Leu Leu Pro Ile Val
            35                  40                  45
```

<210> SEQ ID NO 36
<211> LENGTH: 55
<212> TYPE: PRT
<213> ORGANISM: Artificial Sequence
<220> FEATURE:
<223> OTHER INFORMATION: Synthetic peptide RSVB-IZN30

<400> SEQUENCE: 36

```
Ile Lys Lys Glu Ile Glu Ala Ile Lys Lys Gln Glu Ala Ile Lys
1               5                   10                  15

Lys Lys Ile Glu Ala Ile Glu Lys Glu Val Val Ser Leu Ser Asn Gly
            20                  25                  30

Val Ser Val Leu Thr Ser Lys Val Leu Asp Leu Lys Asn Tyr Ile Asn
            35                  40                  45

Asn Gln Leu Leu Pro Ile Val
        50                  55
```

<210> SEQ ID NO 37
<211> LENGTH: 69
<212> TYPE: PRT
<213> ORGANISM: Artificial Sequence
<220> FEATURE:
<223> OTHER INFORMATION: Synthetic peptide RSVA-IZN45

<400> SEQUENCE: 37

```
Ile Lys Lys Glu Ile Glu Ala Ile Lys Lys Gln Glu Ala Ile Lys
1               5                   10                  15

Lys Lys Ile Glu Ala Ile Glu Lys Glu Val Asn Lys Ile Lys Ser Ala
            20                  25                  30

Leu Leu Ser Thr Asn Lys Ala Val Val Ser Leu Ser Asn Gly Val Ser
            35                  40                  45

Val Leu Thr Ser Lys Val Leu Asp Leu Lys Asn Tyr Ile Asp Lys Gln
            50                  55                  60

Leu Leu Pro Ile Val
65
```

<210> SEQ ID NO 38
<211> LENGTH: 69
<212> TYPE: PRT
<213> ORGANISM: Artificial Sequence
<220> FEATURE:
<223> OTHER INFORMATION: Synthetic peptide RSVB-IZN45

<400> SEQUENCE: 38

```
Ile Lys Lys Glu Ile Glu Ala Ile Lys Lys Gln Glu Ala Ile Lys
1               5                   10                  15

Lys Lys Ile Glu Ala Ile Glu Lys Glu Val Asn Lys Ile Lys Asn Ala
            20                  25                  30

Leu Leu Ser Thr Asn Lys Ala Val Val Ser Leu Ser Asn Gly Val Ser
            35                  40                  45

Val Leu Thr Ser Lys Val Leu Asp Leu Lys Asn Tyr Ile Asn Asn Gln
            50                  55                  60
```

-continued

Leu Leu Pro Ile Val
65

<210> SEQ ID NO 39
<211> LENGTH: 69
<212> TYPE: PRT
<213> ORGANISM: Artificial Sequence
<220> FEATURE:
<223> OTHER INFORMATION: Synthetic peptide RSVA-IZN48

<400> SEQUENCE: 39

Ile Lys Lys Glu Ile Glu Ala Ile Lys Lys Glu Gln Glu Ala Ile Lys
1               5                   10                  15

Lys Lys Ile Glu Ala Leu Glu Gly Glu Val Asn Lys Ile Lys Ser Ala
            20                  25                  30

Leu Leu Ser Thr Asn Lys Ala Val Val Ser Leu Ser Asn Gly Val Ser
        35                  40                  45

Val Leu Thr Ser Lys Val Leu Asp Leu Lys Asn Tyr Ile Asp Lys Gln
    50                  55                  60

Leu Leu Pro Ile Val
65

<210> SEQ ID NO 40
<211> LENGTH: 69
<212> TYPE: PRT
<213> ORGANISM: Artificial Sequence
<220> FEATURE:
<223> OTHER INFORMATION: Synthetic peptide RSVB-IZN48

<400> SEQUENCE: 40

Ile Lys Lys Glu Ile Glu Ala Ile Lys Lys Glu Gln Glu Ala Ile Lys
1               5                   10                  15

Lys Lys Ile Glu Ala Leu Glu Gly Glu Val Asn Lys Ile Lys Asn Ala
            20                  25                  30

Leu Leu Ser Thr Asn Lys Ala Val Val Ser Leu Ser Asn Gly Val Ser
        35                  40                  45

Val Leu Thr Ser Lys Val Leu Asp Leu Lys Asn Tyr Ile Asn Asn Gln
    50                  55                  60

Leu Leu Pro Ile Val
65

<210> SEQ ID NO 41
<211> LENGTH: 7
<212> TYPE: PRT
<213> ORGANISM: Artificial Sequence
<220> FEATURE:
<223> OTHER INFORMATION: X16 Consensus Sequence
<220> FEATURE:
<221> NAME/KEY: VARIANT
<222> LOCATION: 3,5
<223> OTHER INFORMATION: Xaa = Gly, or any of the other 18 natural amino
      acids in the D-configuration excluding Cys

<400> SEQUENCE: 41

Leu Pro Xaa Pro Xaa Trp Trp
1               5

<210> SEQ ID NO 42
<211> LENGTH: 8
<212> TYPE: PRT
<213> ORGANISM: Artificial Sequence
<220> FEATURE:
<223> OTHER INFORMATION: CX10C Consensus Sequence
<220> FEATURE:

```
<221> NAME/KEY: VARIANT
<222> LOCATION: 1
<223> OTHER INFORMATION: Xaa = Arg or Glu
<220> FEATURE:
<221> NAME/KEY: VARIANT
<222> LOCATION: 2
<223> OTHER INFORMATION: Xaa = Gly or any of the other 19 natural amino
      acids in the D-configuration
<220> FEATURE:
<221> NAME/KEY: VARIANT
<222> LOCATION: 3
<223> OTHER INFORMATION: Xaa = His, Glu or Tyr

<400> SEQUENCE: 42

Xaa Xaa Xaa Trp Leu Leu Asp Trp
 1               5

<210> SEQ ID NO 43
<211> LENGTH: 69
<212> TYPE: PRT
<213> ORGANISM: Artificial Sequence
<220> FEATURE:
<223> OTHER INFORMATION: Synthetic peptide Ac-RSVA-IZN45
<220> FEATURE:
<221> NAME/KEY: ACETYLATION
<222> LOCATION: 1
<220> FEATURE:
<221> NAME/KEY: AMIDATION
<222> LOCATION: 69

<400> SEQUENCE: 43

Ile Lys Lys Glu Ile Glu Ala Ile Lys Lys Glu Gln Glu Ala Ile Lys
 1               5                  10                  15

Lys Lys Ile Glu Ala Ile Glu Lys Glu Val Asn Lys Ile Lys Ser Ala
             20                  25                  30

Leu Leu Ser Thr Asn Lys Ala Val Val Ser Leu Ser Asn Gly Val Ser
         35                  40                  45

Val Leu Thr Ser Lys Val Leu Asp Leu Lys Asn Tyr Ile Asp Lys Gln
     50                  55                  60

Leu Leu Pro Ile Val
65

<210> SEQ ID NO 44
<211> LENGTH: 69
<212> TYPE: PRT
<213> ORGANISM: Artificial Sequence
<220> FEATURE:
<223> OTHER INFORMATION: Synthetic peptide Ac-RSVB-IZN45
<220> FEATURE:
<221> NAME/KEY: ACETYLATION
<222> LOCATION: 1
<220> FEATURE:
<221> NAME/KEY: AMIDATION
<222> LOCATION: 69

<400> SEQUENCE: 44

Ile Lys Lys Glu Ile Glu Ala Ile Lys Lys Glu Gln Glu Ala Ile Lys
 1               5                  10                  15

Lys Lys Ile Glu Ala Ile Glu Lys Glu Val Asn Lys Ile Lys Asn Ala
             20                  25                  30

Leu Leu Ser Thr Asn Lys Ala Val Val Ser Leu Ser Asn Gly Val Ser
         35                  40                  45

Val Leu Thr Ser Lys Val Leu Asp Leu Lys Asn Tyr Ile Asn Asn Gln
     50                  55                  60

Leu Leu Pro Ile Val
65
```

<210> SEQ ID NO 45
<211> LENGTH: 72
<212> TYPE: PRT
<213> ORGANISM: Artificial Sequence
<220> FEATURE:
<223> OTHER INFORMATION: Synthetic peptide BPEG2-GKG-RSVA-IZN45
<220> FEATURE:
<221> NAME/KEY: MOD_RES
<222> LOCATION: 1
<223> OTHER INFORMATION: BiotinPEG2 linked directly to N terminus
<220> FEATURE:
<221> NAME/KEY: AMIDATION
<222> LOCATION: 72

<400> SEQUENCE: 45

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Val Asn Lys Ile
            20                  25                  30

Lys Ser Ala Leu Leu Ser Thr Asn Lys Ala Val Val Ser Leu Ser Asn
        35                  40                  45

Gly Val Ser Val Leu Thr Ser Lys Val Leu Asp Leu Lys Asn Tyr Ile
    50                  55                  60

Asp Lys Gln Leu Leu Pro Ile Val
65                  70

<210> SEQ ID NO 46
<211> LENGTH: 72
<212> TYPE: PRT
<213> ORGANISM: Artificial Sequence
<220> FEATURE:
<223> OTHER INFORMATION: Synthetic peptide BPEG2-GKG-RSVB-IZN45
<220> FEATURE:
<221> NAME/KEY: MOD_RES
<222> LOCATION: 1
<223> OTHER INFORMATION: BiotinPEG2 linked directly to N terminus
<220> FEATURE:
<221> NAME/KEY: AMIDATION
<222> LOCATION: 72

<400> SEQUENCE: 46

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Val Asn Lys Ile
            20                  25                  30

Lys Asn Ala Leu Leu Ser Thr Asn Lys Ala Val Val Ser Leu Ser Asn
        35                  40                  45

Gly Val Ser Val Leu Thr Ser Lys Val Leu Asp Leu Lys Asn Tyr Ile
    50                  55                  60

Asn Asn Gln Leu Leu Pro Ile Val
65                  70

<210> SEQ ID NO 47
<211> LENGTH: 72
<212> TYPE: PRT
<213> ORGANISM: Artificial Sequence
<220> FEATURE:
<223> OTHER INFORMATION: Synthetic peptide BPEG2-GKG-RSVA-IZN45 Full Mut
<220> FEATURE:
<221> NAME/KEY: MOD_RES
<222> LOCATION: 1
<223> OTHER INFORMATION: BiotinPEG2 linked to N terminus
<220> FEATURE:
<221> NAME/KEY: AMIDATION
<222> LOCATION: 72

<400> SEQUENCE: 47

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Val Asn Lys Ile
            20                  25                  30

Lys Ser Trp Leu Leu Ser Thr Asn Lys Trp Val Val Ser Leu Ser Asn
        35                  40                  45

Trp Val Ser Val Leu Thr Ser Lys Val Leu Trp Leu Lys Lys Tyr Ile
    50                  55                  60

Asp Lys Gln Leu Leu Pro Ile Val
65                  70

<210> SEQ ID NO 48
<211> LENGTH: 72
<212> TYPE: PRT
<213> ORGANISM: Artificial Sequence
<220> FEATURE:
<223> OTHER INFORMATION: Synthetic peptide BPEG2-GKG-RSVB-IZN45 Full Mut
<220> FEATURE:
<221> NAME/KEY: MOD_RES
<222> LOCATION: 1
<223> OTHER INFORMATION: BiotinPEG2 linked to N terminus
<220> FEATURE:
<221> NAME/KEY: AMIDATION
<222> LOCATION: 72

<400> SEQUENCE: 48

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Val Asn Lys Ile
            20                  25                  30

Lys Asn Trp Leu Leu Ser Thr Asn Lys Trp Val Val Ser Leu Ser Asn
        35                  40                  45

Trp Val Ser Val Leu Thr Ser Lys Val Leu Trp Leu Lys Lys Tyr Ile
    50                  55                  60

Asn Asn Gln Leu Leu Pro Ile Val
65                  70

<210> SEQ ID NO 49
<211> LENGTH: 72
<212> TYPE: PRT
<213> ORGANISM: Artificial Sequence
<220> FEATURE:
<223> OTHER INFORMATION: Synthetic peptide BPEG2-GKG-RSVA-IZN45 WT-top
<220> FEATURE:
<221> NAME/KEY: MOD_RES
<222> LOCATION: 1
<223> OTHER INFORMATION: BiotinPEG2 linked to N terminus
<220> FEATURE:
<221> NAME/KEY: AMIDATION
<222> LOCATION: 72

<400> SEQUENCE: 49

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Val Asn Lys Ile
            20                  25                  30

Lys Ser Ala Leu Leu Ser Thr Asn Lys Ala Val Val Ser Leu Ser Asn
        35                  40                  45

Trp Val Ser Val Leu Thr Ser Lys Val Leu Trp Leu Lys Lys Tyr Ile
    50                  55                  60

```
Asp Lys Gln Leu Leu Pro Ile Val
 65                  70
```

<210> SEQ ID NO 50
<211> LENGTH: 72
<212> TYPE: PRT
<213> ORGANISM: Artificial Sequence
<220> FEATURE:
<223> OTHER INFORMATION: Synthetic peptide BPEG2-GKG-RSVB-IZN45 wt top
<220> FEATURE:
<221> NAME/KEY: MOD_RES
<222> LOCATION: 1
<223> OTHER INFORMATION: BiotinPEG2 directly linked to N terminus
<220> FEATURE:
<221> NAME/KEY: AMIDATION
<222> LOCATION: 72

<400> SEQUENCE: 50

```
Gly Lys Gly Ile Lys Lys Glu Ile Glu Ala Ile Lys Lys Glu Gln Glu
1               5                  10                  15

Ala Ile Lys Lys Lys Ile Glu Ala Ile Glu Lys Glu Val Asn Lys Ile
            20                  25                  30

Lys Asn Ala Leu Leu Ser Thr Asn Lys Ala Val Val Ser Leu Ser Asn
        35                  40                  45

Trp Val Ser Val Leu Thr Ser Lys Val Leu Trp Leu Lys Lys Tyr Ile
    50                  55                  60

Asn Asn Gln Leu Leu Pro Ile Val
 65                  70
```

<210> SEQ ID NO 51
<211> LENGTH: 72
<212> TYPE: PRT
<213> ORGANISM: Artificial Sequence
<220> FEATURE:
<223> OTHER INFORMATION: Synthetic peptide BPEG2-GKG-RSVA-IZN45 WT-bot
<220> FEATURE:
<221> NAME/KEY: MOD_RES
<222> LOCATION: 1
<223> OTHER INFORMATION: BiotinPEG2 directly linked to N terminus
<220> FEATURE:
<221> NAME/KEY: AMIDATION
<222> LOCATION: 72

<400> SEQUENCE: 51

```
Gly Lys Gly Ile Lys Lys Glu Ile Glu Ala Ile Lys Lys Glu Gln Glu
1               5                  10                  15

Ala Ile Lys Lys Lys Ile Glu Ala Ile Glu Lys Glu Val Asn Lys Ile
            20                  25                  30

Lys Ser Trp Leu Leu Ser Thr Asn Lys Trp Val Val Ser Leu Ser Asn
        35                  40                  45

Gly Val Ser Val Leu Thr Ser Lys Val Leu Asp Leu Lys Asn Tyr Ile
    50                  55                  60

Asp Lys Gln Leu Leu Pro Ile Val
 65                  70
```

<210> SEQ ID NO 52
<211> LENGTH: 72
<212> TYPE: PRT
<213> ORGANISM: Artificial Sequence
<220> FEATURE:
<223> OTHER INFORMATION: Synthetic peptide BPEG2-GKG-RSVB-IZN45 wt bot
<220> FEATURE:
<221> NAME/KEY: MOD_RES
<222> LOCATION: 1
<223> OTHER INFORMATION: BiotinPEG2 linked to N terminus
<220> FEATURE:

<221> NAME/KEY: AMIDATION
<222> LOCATION: 72

<400> SEQUENCE: 52

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Val Asn Lys Ile
            20                  25                  30

Lys Asn Trp Leu Leu Ser Thr Asn Lys Trp Val Val Ser Leu Ser Asn
        35                  40                  45

Gly Val Ser Val Leu Thr Ser Lys Val Leu Asp Leu Lys Asn Tyr Ile
    50                  55                  60

Asn Asn Gln Leu Leu Pro Ile Val
65                  70

<210> SEQ ID NO 53
<211> LENGTH: 72
<212> TYPE: PRT
<213> ORGANISM: Artificial Sequence
<220> FEATURE:
<223> OTHER INFORMATION: Synthetic peptide BPEG2-GKG-RSVA-IZN45 WT-mid
<220> FEATURE:
<221> NAME/KEY: MOD_RES
<222> LOCATION: 1
<223> OTHER INFORMATION: BiotinPEG2 directly linked to N terminus
<220> FEATURE:
<221> NAME/KEY: AMIDATION
<222> LOCATION: 72

<400> SEQUENCE: 53

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Val Asn Lys Ile
            20                  25                  30

Lys Ser Trp Leu Leu Ser Thr Asn Lys Ala Val Val Ser Leu Ser Asn
        35                  40                  45

Gly Val Ser Val Leu Thr Ser Lys Val Leu Trp Leu Lys Lys Tyr Ile
    50                  55                  60

Asp Lys Gln Leu Leu Pro Ile Val
65 70

<210> SEQ ID NO 54
<211> LENGTH: 71
<212> TYPE: PRT
<213> ORGANISM: Artificial Sequence
<220> FEATURE:
<223> OTHER INFORMATION: Synthetic peptide BPEG2-GKG-RSVB-IZN45 wt mid
<220> FEATURE:
<221> NAME/KEY: MOD_RES
<222> LOCATION: 1
<223> OTHER INFORMATION: BiotinPEG2 directly linked to N terminus
<220> FEATURE:
<221> NAME/KEY: AMIDATION
<222> LOCATION: 72

<400> SEQUENCE: 54

Gly Lys Gly Ile Lys Lys Glu Ile Glu Ala Ile Lys Lys Glu Gln Glu
1 5 10 15

Ala Ile Lys Lys Lys Ile Glu Ala Ile Glu Lys Glu Val Asn Lys Ile
20 25 30

Lys Asn Trp Leu Leu Ser Thr Asn Lys Ala Val Val Ser Leu Ser Asn
35 40 45

Gly Val Ser Val Leu Thr Ser Lys Val Leu Trp Leu Lys Tyr Ile Asn

-continued

```
                50                  55                  60
Asn Gln Leu Leu Pro Ile Val
65                  70

<210> SEQ ID NO 55
<211> LENGTH: 58
<212> TYPE: PRT
<213> ORGANISM: Artificial Sequence
<220> FEATURE:
<223> OTHER INFORMATION: Synthetic peptide BPEG2-GKG-RSVB-IZN30
<220> FEATURE:
<221> NAME/KEY: MOD_RES
<222> LOCATION: 1
<223> OTHER INFORMATION: BiotinPEG2 directly linked to N terminus
<220> FEATURE:
<221> NAME/KEY: AMIDATION
<222> LOCATION: 58

<400> SEQUENCE: 55

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Val Val Ser Leu
                20                  25                  30

Ser Asn Gly Val Ser Val Leu Thr Ser Lys Val Leu Asp Leu Lys Asn
            35                  40                  45

Tyr Ile Asn Asn Gln Leu Leu Pro Ile Val
    50                  55

<210> SEQ ID NO 56
<211> LENGTH: 48
<212> TYPE: PRT
<213> ORGANISM: Artificial Sequence
<220> FEATURE:
<223> OTHER INFORMATION: Synthetic peptide BPEG2-GKG-RSVA-IZN18
<220> FEATURE:
<221> NAME/KEY: MOD_RES
<222> LOCATION: 1
<223> OTHER INFORMATION: BiotinPEG2 directly linked to N terminus
<220> FEATURE:
<221> NAME/KEY: AMIDATION
<222> LOCATION: 48

<400> SEQUENCE: 56

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Ile Glu Val Leu
                20                  25                  30

Thr Ser Lys Val Leu Asp Leu Lys Asn Tyr Ile Asp Lys Gln Leu Leu
            35                  40                  45

<210> SEQ ID NO 57
<211> LENGTH: 48
<212> TYPE: PRT
<213> ORGANISM: Artificial Sequence
<220> FEATURE:
<223> OTHER INFORMATION: Synthetic peptide BPEG2-GKG-RSVB-IZN18
<220> FEATURE:
<221> NAME/KEY: MOD_RES
<222> LOCATION: 1
<223> OTHER INFORMATION: BiotinPEG2 directly linked to N terminus
<220> FEATURE:
<221> NAME/KEY: AMIDATION
<222> LOCATION: 48

<400> SEQUENCE: 57

Gly Lys Gly Ile Lys Lys Glu Ile Glu Ala Ile Lys Lys Glu Gln Glu
1               5                   10                  15
```

```
Ala Ile Lys Lys Lys Ile Glu Ala Ile Glu Lys Glu Ile Glu Val Leu
            20                  25                  30

Thr Ser Lys Val Leu Asp Leu Lys Asn Tyr Ile Asn Asn Gln Leu Leu
            35                  40                  45

<210> SEQ ID NO 58
<211> LENGTH: 51
<212> TYPE: PRT
<213> ORGANISM: Artificial Sequence
<220> FEATURE:
<223> OTHER INFORMATION: Synthetic peptide BPEG2-GKG-RSVB-IZN21
<220> FEATURE:
<221> NAME/KEY: MOD_RES
<222> LOCATION: 1
<223> OTHER INFORMATION: BiotinPEG2 directly linked to N terminus
<220> FEATURE:
<221> NAME/KEY: AMIDATION
<222> LOCATION: 51

<400> SEQUENCE: 58

Gly Lys Gly Ile Lys Lys Glu Ile Glu Ala Ile Lys Lys Glu Gln Glu
1               5                   10                  15

Ala Ile Lys Lys Lys Ile Glu Ala Ile Glu Lys Glu Ile Glu Val Leu
            20                  25                  30

Thr Ser Lys Val Leu Asp Leu Lys Asn Tyr Ile Asn Asn Gln Leu Leu
            35                  40                  45

Pro Ile Val
    50

<210> SEQ ID NO 59
<211> LENGTH: 48
<212> TYPE: PRT
<213> ORGANISM: Artificial Sequence
<220> FEATURE:
<223> OTHER INFORMATION: Synthetic peptide Ac-RSV-A IZN21
<220> FEATURE:
<221> NAME/KEY: ACETYLATION
<222> LOCATION: 1
<220> FEATURE:
<221> NAME/KEY: AMIDATION
<222> LOCATION: 48

<400> SEQUENCE: 59

Ile Lys Lys Glu Ile Glu Ala Ile Lys Lys Glu Gln Glu Ala Ile Lys
1               5                   10                  15

Lys Lys Ile Glu Ala Ile Glu Lys Glu Ile Glu Val Leu Thr Ser Lys
            20                  25                  30

Val Leu Asp Leu Lys Asn Tyr Ile Asp Lys Gln Leu Leu Pro Ile Val
            35                  40                  45

<210> SEQ ID NO 60
<211> LENGTH: 72
<212> TYPE: PRT
<213> ORGANISM: Artificial Sequence
<220> FEATURE:
<223> OTHER INFORMATION: Synthetic peptide BPEG2-GKG-RSVA-IZN48
<220> FEATURE:
<221> NAME/KEY: MOD_RES
<222> LOCATION: 1
<223> OTHER INFORMATION: BiotinPEG2 directly linked to N terminal
<220> FEATURE:
<221> NAME/KEY: AMIDATION
<222> LOCATION: 72

<400> SEQUENCE: 60

Gly Lys Gly Ile Lys Lys Glu Ile Glu Ala Ile Lys Lys Glu Gln Glu
```

```
                1               5                  10                 15
Ala Ile Lys Lys Lys Ile Glu Ala Leu Glu Gly Glu Val Asn Lys Ile
            20                  25                 30

Lys Ser Ala Leu Leu Ser Thr Asn Lys Ala Val Val Ser Leu Ser Asn
            35                  40                 45

Gly Val Ser Val Leu Thr Ser Lys Val Leu Asp Leu Lys Asn Tyr Ile
    50                  55                 60

Asp Lys Gln Leu Leu Pro Ile Val
65                  70

<210> SEQ ID NO 61
<211> LENGTH: 72
<212> TYPE: PRT
<213> ORGANISM: Artificial Sequence
<220> FEATURE:
<223> OTHER INFORMATION: Synthetic peptide BPEG2-GKG-RSVB-IZN48
<220> FEATURE:
<221> NAME/KEY: MOD_RES
<222> LOCATION: 1
<223> OTHER INFORMATION: BiotinPEG2 directly linked to N terminus
<220> FEATURE:
<221> NAME/KEY: AMIDATION
<222> LOCATION: 72

<400> SEQUENCE: 61

Gly Lys Gly Ile Lys Lys Glu Ile Glu Ala Ile Lys Lys Glu Gln Glu
1               5                  10                 15

Ala Ile Lys Lys Lys Ile Glu Ala Leu Glu Gly Glu Val Asn Lys Ile
            20                  25                 30

Lys Asn Ala Leu Leu Ser Thr Asn Lys Ala Val Val Ser Leu Ser Asn
            35                  40                 45

Gly Val Ser Val Leu Thr Ser Lys Val Leu Asp Leu Lys Asn Tyr Ile
    50                  55                 60

Asn Asn Gln Leu Leu Pro Ile Val
65                  70

<210> SEQ ID NO 62
<211> LENGTH: 69
<212> TYPE: PRT
<213> ORGANISM: Artificial Sequence
<220> FEATURE:
<223> OTHER INFORMATION: Synthetic peptide RSVB-IZN48
<220> FEATURE:
<221> NAME/KEY: AMIDATION
<222> LOCATION: 69

<400> SEQUENCE: 62

Ile Lys Lys Glu Ile Glu Ala Ile Lys Lys Glu Gln Glu Ala Ile Lys
1               5                  10                 15

Lys Lys Ile Glu Ala Leu Glu Gly Glu Val Asn Lys Ile Lys Asn Ala
            20                  25                 30

Leu Leu Ser Thr Asn Lys Ala Val Val Ser Leu Ser Asn Gly Val Ser
            35                  40                 45

Val Leu Thr Ser Lys Val Leu Asp Leu Lys Asn Tyr Ile Asn Asn Gln
    50                  55                 60

Leu Leu Pro Ile Val
65

<210> SEQ ID NO 63
<211> LENGTH: 74
<212> TYPE: PRT
<213> ORGANISM: Artificial Sequence
```

```
<220> FEATURE:
<223> OTHER INFORMATION: Synthetic peptide
      RSVA-N49IZ-GKG-Glu(biotinyl-PEG)-NH2
<220> FEATURE:
<221> NAME/KEY: MOD_RES
<222> LOCATION: 74
<223> OTHER INFORMATION: Glu(biotinyl-PEG) directly linked to C terminus
<220> FEATURE:
<221> NAME/KEY: AMIDATION
<222> LOCATION: 74
<223> OTHER INFORMATION: Linked to Glu(biotinyl-PEG)

<400> SEQUENCE: 63

Leu Glu Gly Glu Val Asn Lys Ile Lys Ser Ala Leu Leu Ser Thr Asn
1               5                   10                  15

Lys Ala Val Val Ser Leu Ser Asn Gly Val Ser Val Leu Thr Ser Lys
            20                  25                  30

Val Leu Asp Leu Lys Asn Tyr Ile Asp Lys Gln Leu Leu Pro Ile Val
        35                  40                  45

Asn Ile Lys Lys Glu Ile Glu Ala Ile Lys Lys Glu Gln Glu Ala Ile
    50                  55                  60

Lys Lys Lys Ile Glu Ala Ile Gly Lys Gly
65                  70

<210> SEQ ID NO 64
<211> LENGTH: 74
<212> TYPE: PRT
<213> ORGANISM: Artificial Sequence
<220> FEATURE:
<223> OTHER INFORMATION: Synthetic peptide
      RSVB-N49IZ-GKG-Glu(biotinyl-PEG)-NH2
<220> FEATURE:
<221> NAME/KEY: MOD_RES
<222> LOCATION: 74
<223> OTHER INFORMATION: Glu(biotinyl-PEG)- directly linked to C
      terminus
<220> FEATURE:
<221> NAME/KEY: AMIDATION
<222> LOCATION: 74
<223> OTHER INFORMATION: Linked to Glu(biotinyl-PEG)

<400> SEQUENCE: 64

Leu Glu Gly Glu Val Asn Lys Ile Lys Asn Ala Leu Leu Ser Thr Asn
1               5                   10                  15

Lys Ala Val Val Ser Leu Ser Asn Gly Val Ser Val Leu Thr Ser Lys
            20                  25                  30

Val Leu Asp Leu Lys Asn Tyr Ile Asn Asn Gln Leu Leu Pro Ile Val
        35                  40                  45

Asn Ile Lys Lys Glu Ile Glu Ala Ile Lys Lys Glu Gln Glu Ala Ile
    50                  55                  60

Lys Lys Lys Ile Glu Ala Ile Gly Lys Gly
65                  70

<210> SEQ ID NO 65
<211> LENGTH: 11
<212> TYPE: PRT
<213> ORGANISM: Artificial Sequence
<220> FEATURE:
<223> OTHER INFORMATION: X12 Secondary Library Consensus Sequence
<220> FEATURE:
<221> NAME/KEY: VARIANT
<222> LOCATION: 1,2,3,4,7, 9
<223> OTHER INFORMATION: Xaa = Gly or any of the other 19 natural amino
      acids in the D-configuration

<400> SEQUENCE: 65
```

```
Xaa Xaa Xaa Xaa Leu Pro Xaa Pro Xaa Trp Trp
1               5                   10

<210> SEQ ID NO 66
<211> LENGTH: 16
<212> TYPE: PRT
<213> ORGANISM: Artificial Sequence
<220> FEATURE:
<223> OTHER INFORMATION: CX10C Secondary Library Consensus Sequence
<220> FEATURE:
<221> NAME/KEY: VARIANT
<222> LOCATION: 1,2,4
<223> OTHER INFORMATION: Xaa = Gly, or any of the other 18 natural amino
      acids in the D-configuration excluding Cys
<220> FEATURE:
<221> NAME/KEY: VARIANT
<222> LOCATION: 6
<223> OTHER INFORMATION: Xaa = Arg, Glu, Gly, or Lys
<220> FEATURE:
<221> NAME/KEY: VARIANT
<222> LOCATION: 7
<223> OTHER INFORMATION: Xaa = Gly, or any of the other 18 natural amino
      acids in the D-configuration excluding Cys
<220> FEATURE:
<221> NAME/KEY: VARIANT
<222> LOCATION: 8
<223> OTHER INFORMATION: Xaa = His, Glu, Tyr, Asp or Gln
<220> FEATURE:
<221> NAME/KEY: VARIANT
<222> LOCATION: 15,16
<223> OTHER INFORMATION: Xaa = Gly, or any of the other 18 natural amino
      acids in the D-configuration excluding Cys

<400> SEQUENCE: 66

Xaa Xaa Cys Xaa Asn Xaa Xaa Xaa Trp Leu Leu Asp Trp Cys Xaa Xaa
1               5                   10                  15

<210> SEQ ID NO 67
<211> LENGTH: 37
<212> TYPE: PRT
<213> ORGANISM: Artificial Sequence
<220> FEATURE:
<223> OTHER INFORMATION: Synthetic peptide YG-T118
<220> FEATURE:
<221> NAME/KEY: AMIDATION
<222> LOCATION: 37

<400> SEQUENCE: 67

Tyr Gly Phe Asp Ala Ser Ile Ser Gln Val Asn Glu Lys Ile Asn Gln
1               5                   10                  15

Ser Leu Ala Phe Ile Arg Lys Ser Asp Glu Leu Leu His Asn Val Asn
                20                  25                  30

Ala Gly Lys Ser Thr
            35

<210> SEQ ID NO 68
<211> LENGTH: 38
<212> TYPE: PRT
<213> ORGANISM: Artificial Sequence
<220> FEATURE:
<223> OTHER INFORMATION: Synthetic peptide YG-T118-Tricasso
<220> FEATURE:
<221> NAME/KEY: ACETYLATION
<222> LOCATION: 1
<220> FEATURE:
<221> NAME/KEY: MOD_RES
<222> LOCATION: 38
<223> OTHER INFORMATION: (PEG6) directly linked to C terminus

<400> SEQUENCE: 68

Tyr Gly Phe Asp Ala Ser Ile Ser Gln Val Asn Glu Lys Ile Asn Gln
```

```
                1               5                  10                  15
Ser Leu Ala Phe Ile Arg Lys Ser Asp Glu Leu Leu His Asn Val Asn
                    20                  25                  30

Ala Gly Lys Ser Thr Gly
            35
```

<210> SEQ ID NO 69
<211> LENGTH: 39
<212> TYPE: PRT
<213> ORGANISM: Artificial Sequence
<220> FEATURE:
<223> OTHER INFORMATION: Synthetic peptide YG-T118-GC-Cholesterol
<220> FEATURE:
<221> NAME/KEY: MOD_RES
<222> LOCATION: 39
<223> OTHER INFORMATION: Cholesterol directly linked to C terminus

<400> SEQUENCE: 69

```
                1               5                  10                  15
Tyr Gly Phe Asp Ala Ser Ile Ser Gln Val Asn Glu Lys Ile Asn Gln

Ser Leu Ala Phe Ile Arg Lys Ser Asp Glu Leu Leu His Asn Val Asn
                    20                  25                  30

Ala Gly Lys Ser Thr Gly Cys
            35
```

<210> SEQ ID NO 70
<211> LENGTH: 69
<212> TYPE: PRT
<213> ORGANISM: Artificial Sequence
<220> FEATURE:
<223> OTHER INFORMATION: Synthetic peptide Ac-RSV-A IZN45
<220> FEATURE:
<221> NAME/KEY: ACETYLATION
<222> LOCATION: 1
<220> FEATURE:
<221> NAME/KEY: AMIDATION
<222> LOCATION: 69

<400> SEQUENCE: 70

```
Ile Lys Lys Glu Ile Glu Ala Ile Lys Lys Glu Gln Glu Ala Ile Lys
1               5                   10                  15

Lys Lys Ile Glu Ala Ile Glu Lys Glu Val Asn Lys Ile Lys Ser Ala
                    20                  25                  30

Leu Leu Ser Thr Asn Lys Ala Val Val Ser Leu Ser Asn Gly Val Ser
            35                  40                  45

Val Leu Thr Ser Lys Val Leu Asp Leu Lys Asn Tyr Ile Asp Lys Gln
        50                  55                  60

Leu Leu Pro Ile Val
65
```

<210> SEQ ID NO 71
<211> LENGTH: 72
<212> TYPE: PRT
<213> ORGANISM: Artificial Sequence
<220> FEATURE:
<223> OTHER INFORMATION: Synthetic peptide (Biotin-PEG2)GKG-RSVA IZN48
<220> FEATURE:
<221> NAME/KEY: MOD_RES
<222> LOCATION: 1
<223> OTHER INFORMATION: Biotin-PEG2 directly linked to N terminus
<220> FEATURE:
<221> NAME/KEY: AMIDATION
<222> LOCATION: 72

<400> SEQUENCE: 71

```
Gly Lys Gly Ile Lys Lys Glu Ile Glu Ala Ile Lys Lys Glu Gln Glu
1               5                   10                  15

Ala Ile Lys Lys Lys Ile Glu Ala Leu Glu Gly Glu Val Asn Lys Ile
                20                  25                  30

Lys Ser Ala Leu Leu Ser Thr Asn Lys Ala Val Val Ser Leu Ser Asn
            35                  40                  45

Gly Val Ser Val Leu Thr Ser Lys Val Leu Asp Leu Lys Asn Tyr Ile
        50                  55                  60

Asp Lys Gln Leu Leu Pro Ile Val
65                  70
```

<210> SEQ ID NO 72
<211> LENGTH: 74
<212> TYPE: PRT
<213> ORGANISM: Artificial Sequence
<220> FEATURE:
<223> OTHER INFORMATION: Synthetic peptide RSVA N49IZ-GKG(Glu-Biotinyl-PEG)
<220> FEATURE:
<221> NAME/KEY: MOD_RES
<222> LOCATION: 74
<223> OTHER INFORMATION: (Glu-biotinyl-PEG) directly linked to C terminus
<220> FEATURE:
<221> NAME/KEY: AMIDATION
<222> LOCATION: 74
<223> OTHER INFORMATION: linked to (Glu-biotinyl-PEG)

<400> SEQUENCE: 72

```
Leu Glu Gly Glu Val Asn Lys Ile Lys Ser Ala Leu Leu Ser Thr Asn
1               5                   10                  15

Lys Ala Val Val Ser Leu Ser Asn Gly Val Ser Val Leu Thr Ser Lys
                20                  25                  30

Val Leu Asp Leu Lys Asn Tyr Ile Asp Lys Gln Leu Leu Pro Ile Val
            35                  40                  45

Asn Ile Lys Lys Glu Ile Glu Ala Ile Lys Lys Glu Gln Glu Ala Ile
        50                  55                  60

Lys Lys Lys Ile Glu Ala Ile Gly Lys Gly
65                  70
```

<210> SEQ ID NO 73
<211> LENGTH: 16
<212> TYPE: PRT
<213> ORGANISM: Artificial Sequence
<220> FEATURE:
<223> OTHER INFORMATION: Synthetic peptide X16-16 with amidation
<220> FEATURE:
<221> NAME/KEY: AMIDATION
<222> LOCATION: 16

<400> SEQUENCE: 73

```
Asp Tyr Leu Pro Leu Pro Glu Pro Arg Trp Trp Phe Pro Glu Tyr Gln
1               5                   10                  15
```

<210> SEQ ID NO 74
<211> LENGTH: 16
<212> TYPE: PRT
<213> ORGANISM: Artificial Sequence
<220> FEATURE:
<223> OTHER INFORMATION: Synthetic peptide X16-18 with amidation
<220> FEATURE:
<221> NAME/KEY: AMIDATION
<222> LOCATION: 16

<400> SEQUENCE: 74

Ser Leu Lys Tyr Trp Trp Met Glu Glu Leu Pro Leu Pro Lys Trp Trp
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Synthetic peptide Ac-X16-18
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 75

Ser Leu Lys Tyr Trp Trp Met Glu Glu Leu Pro Leu Pro Lys Trp Trp
1               5                   10                  15

<210> SEQ ID NO 76
<211> LENGTH: 18
<212> TYPE: PRT
<213> ORGANISM: Artificial Sequence
<220> FEATURE:
<223> OTHER INFORMATION: Synthetic peptide X16-18-GG
<220> FEATURE:
<221> NAME/KEY: AMIDATION
<222> LOCATION: 18

<400> SEQUENCE: 76

Ser Leu Lys Tyr Trp Trp Met Glu Glu Leu Pro Leu Pro Lys Trp Trp
1               5                   10                  15

Gly Gly

<210> SEQ ID NO 77
<211> LENGTH: 18
<212> TYPE: PRT
<213> ORGANISM: Artificial Sequence
<220> FEATURE:
<223> OTHER INFORMATION: Synthetic peptide Ac-X16-18-GG
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 77

Ser Leu Lys Tyr Trp Trp Met Glu Glu Leu Pro Leu Pro Lys Trp Trp
1               5                   10                  15

Gly Gly

<210> SEQ ID NO 78
<211> LENGTH: 19
<212> TYPE: PRT
<213> ORGANISM: Artificial Sequence
<220> FEATURE:
<223> OTHER INFORMATION: Synthetic peptide Ac-X16-18-GG(PEG6)K
<220> FEATURE:
<221> NAME/KEY: ACETYLATION
<222> LOCATION: 1
<220> FEATURE:
<221> NAME/KEY: VARIANT
<222> LOCATION: 3, 14
<223> OTHER INFORMATION: Xaa = Lys with DDE protecting group
<220> FEATURE:
<221> NAME/KEY: MOD_RES
<222> LOCATION: 18
<223> OTHER INFORMATION: PEG6 sequence inserted directly into sequence

```
                        between Gly and Lys
<220> FEATURE:
<221> NAME/KEY: AMIDATION
<222> LOCATION: 19

<400> SEQUENCE: 78

Ser Leu Xaa Tyr Trp Trp Met Glu Glu Leu Pro Leu Pro Xaa Trp Trp
1               5                   10                  15

Gly Gly Lys

<210> SEQ ID NO 79
<211> LENGTH: 19
<212> TYPE: PRT
<213> ORGANISM: Artificial Sequence
<220> FEATURE:
<223> OTHER INFORMATION: Synthetic peptide Ac-X16-18-GG(PEG6)K scram
<220> FEATURE:
<221> NAME/KEY: ACETYLATION
<222> LOCATION: 1
<220> FEATURE:
<221> NAME/KEY: VARIANT
<222> LOCATION: 3,10
<223> OTHER INFORMATION: Xaa = Lys with DDE protecting group
<220> FEATURE:
<221> NAME/KEY: MOD_RES
<222> LOCATION: 18
<223> OTHER INFORMATION: PEG6 inserted directly in sequence between Gly
      and Lys
<220> FEATURE:
<221> NAME/KEY: AMIDATION
<222> LOCATION: 19

<400> SEQUENCE: 79

Leu Trp Xaa Ser Trp Glu Trp Leu Glu Xaa Trp Pro Met Tyr Pro Leu
1               5                   10                  15

Gly Gly Lys

<210> SEQ ID NO 80
<211> LENGTH: 18
<212> TYPE: PRT
<213> ORGANISM: Artificial Sequence
<220> FEATURE:
<223> OTHER INFORMATION: Synthetic peptide X16-20-GK
<220> FEATURE:
<221> NAME/KEY: AMIDATION
<222> LOCATION: 18

<400> SEQUENCE: 80

His Trp Leu Pro Leu Gln Pro Trp Trp Asp Asp Ile Pro Val Trp His
1               5                   10                  15

Gly Lys

<210> SEQ ID NO 81
<211> LENGTH: 18
<212> TYPE: PRT
<213> ORGANISM: Artificial Sequence
<220> FEATURE:
<223> OTHER INFORMATION: Synthetic peptide Ac-X16-20-GK
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 81

His Trp Leu Pro Leu Gln Pro Trp Trp Asp Asp Ile Pro Val Trp His
1               5                   10                  15
```

Gly Lys

```
<210> SEQ ID NO 82
<211> LENGTH: 13
<212> TYPE: PRT
<213> ORGANISM: Artificial Sequence
<220> FEATURE:
<223> OTHER INFORMATION: Synthetic peptide Ac-X12-G12-G
<220> FEATURE:
<221> NAME/KEY: ACETYLATION
<222> LOCATION: 1
<220> FEATURE:
<221> NAME/KEY: AMIDATION
<222> LOCATION: 13

<400> SEQUENCE: 82

Lys Val Trp Thr Ile Gln Lys Pro Leu Thr Leu Tyr Gly
1               5                   10

<210> SEQ ID NO 83
<211> LENGTH: 13
<212> TYPE: PRT
<213> ORGANISM: Artificial Sequence
<220> FEATURE:
<223> OTHER INFORMATION: Synthetic peptide Ac-X12-H11-G
<220> FEATURE:
<221> NAME/KEY: ACETYLATION
<222> LOCATION: 1
<220> FEATURE:
<221> NAME/KEY: AMIDATION
<222> LOCATION: 13

<400> SEQUENCE: 83

Thr Met His His Lys Val Trp Leu Ile Pro Lys Ala Gly
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic peptide X12-31
<220> FEATURE:
<221> NAME/KEY: AMIDATION
<222> LOCATION: 12

<400> SEQUENCE: 84

Ala Leu Thr Tyr Thr Leu Pro Val Pro His Trp Trp
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Synthetic peptide X12-45-GK
<220> FEATURE:
<221> NAME/KEY: AMIDATION
<222> LOCATION: 14

<400> SEQUENCE: 85

Ile Ser Leu Pro Thr Pro Thr Trp Trp Pro Ser Thr Gly Lys
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Synthetic peptide Ac-X12-45-GK
```

```
<220> FEATURE:
<221> NAME/KEY: ACETYLATION
<222> LOCATION: 1
<220> FEATURE:
<221> NAME/KEY: AMIDATION
<222> LOCATION: 14

<400> SEQUENCE: 86

Ile Ser Leu Pro Thr Pro Thr Trp Trp Pro Ser Thr Gly Lys
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Synthetic peptide X12-45-GG
<220> FEATURE:
<221> NAME/KEY: AMIDATION
<222> LOCATION: 14

<400> SEQUENCE: 87

Ile Ser Leu Pro Thr Pro Thr Trp Trp Pro Ser Thr Gly Gly
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Synthetic peptide Ac-X12-45-GG
<220> FEATURE:
<221> NAME/KEY: ACETYLATION
<222> LOCATION: 1
<220> FEATURE:
<221> NAME/KEY: AMIDATION
<222> LOCATION: 14

<400> SEQUENCE: 88

Ile Ser Leu Pro Thr Pro Thr Trp Trp Pro Ser Thr Gly Gly
1               5                   10

<210> SEQ ID NO 89
<211> LENGTH: 15
<212> TYPE: PRT
<213> ORGANISM: Artificial Sequence
<220> FEATURE:
<223> OTHER INFORMATION: Synthetic peptide Ac-X12-45-GG(PEG6)K
<220> FEATURE:
<221> NAME/KEY: ACETYLATION
<222> LOCATION: 1
<220> FEATURE:
<221> NAME/KEY: MOD_RES
<222> LOCATION: 14
<223> OTHER INFORMATION: PEG6 inserted directly into sequence between
      Gly and Lys
<220> FEATURE:
<221> NAME/KEY: AMIDATION
<222> LOCATION: 15

<400> SEQUENCE: 89

Ile Ser Leu Pro Thr Pro Thr Trp Trp Pro Ser Thr Gly Gly Lys
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic peptide Ac-X12-45-GG(PEG6)K scram
<220> FEATURE:
```

```
<221> NAME/KEY: ACETYLATION
<222> LOCATION: 1
<220> FEATURE:
<221> NAME/KEY: MOD_RES
<222> LOCATION: 14
<223> OTHER INFORMATION: PEG6 directly inserted into sequence between
      Gly and Lys
<220> FEATURE:
<221> NAME/KEY: AMIDATION
<222> LOCATION: 15

<400> SEQUENCE: 90

Thr Trp Leu Pro Trp Thr Ile Ser Pro Thr Pro Ser Gly Gly Lys
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic peptide Ac-K(PEG6)GG-X12-45
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into sequence between
      Lys and Gly
<220> FEATURE:
<221> NAME/KEY: AMIDATION
<222> LOCATION: 15

<400> SEQUENCE: 91

Lys Gly Gly Ile Ser Leu Pro Thr Pro Thr Trp Trp Pro Ser Thr
1               5                   10                  15

<210> SEQ ID NO 92
<211> LENGTH: 12
<212> TYPE: PRT
<213> ORGANISM: Artificial Sequence
<220> FEATURE:
<223> OTHER INFORMATION: Synthetic peptide X12-47
<220> FEATURE:
<221> NAME/KEY: AMIDATION
<222> LOCATION: 12

<400> SEQUENCE: 92

Ser Lys Val Ile Leu Pro Glu Pro Phe Trp Trp Pro
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Synthetic peptide Ac-X12-47
<220> FEATURE:
<221> NAME/KEY: ACETYLATION
<222> LOCATION: 1
<220> FEATURE:
<221> NAME/KEY: AMIDATION
<222> LOCATION: 12

<400> SEQUENCE: 93

Ser Lys Val Ile Leu Pro Glu Pro Phe Trp Trp Pro
1               5                   10

<210> SEQ ID NO 94
<211> LENGTH: 14
<212> TYPE: PRT
```

```
<213> ORGANISM: Artificial Sequence
<220> FEATURE:
<223> OTHER INFORMATION: Synthetic peptide X12-47-GG
<220> FEATURE:
<221> NAME/KEY: AMIDATION
<222> LOCATION: 14

<400> SEQUENCE: 94

Ser Lys Val Ile Leu Pro Glu Pro Phe Trp Trp Pro Gly Gly
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Synthetic peptide Ac-X12-47-GG
<220> FEATURE:
<221> NAME/KEY: ACETYLATION
<222> LOCATION: 1
<220> FEATURE:
<221> NAME/KEY: AMIDATION
<222> LOCATION: 14

<400> SEQUENCE: 95

Ser Lys Val Ile Leu Pro Glu Pro Phe Trp Trp Pro Gly Gly
1               5                   10

<210> SEQ ID NO 96
<211> LENGTH: 15
<212> TYPE: PRT
<213> ORGANISM: Artificial Sequence
<220> FEATURE:
<223> OTHER INFORMATION: Synthetic peptide Ac-X12-47-GG(PEG6)K
<220> FEATURE:
<221> NAME/KEY: ACETYLATION
<222> LOCATION: 1
<220> FEATURE:
<221> NAME/KEY: VARIANT
<222> LOCATION: 2
<223> OTHER INFORMATION: Xaa = Lys with DDE protecting group
<220> FEATURE:
<221> NAME/KEY: MOD_RES
<222> LOCATION: 14
<223> OTHER INFORMATION: PEG6 inserted directly into sequence between
      Gly and Lys
<220> FEATURE:
<221> NAME/KEY: AMIDATION
<222> LOCATION: 15

<400> SEQUENCE: 96

Ser Xaa Val Ile Leu Pro Glu Pro Phe Trp Trp Pro Gly Gly Lys
1               5                   10                  15

<210> SEQ ID NO 97
<211> LENGTH: 13
<212> TYPE: PRT
<213> ORGANISM: Artificial Sequence
<220> FEATURE:
<223> OTHER INFORMATION: Synthetic peptide RSVP1-G(PEG6)K
<220> FEATURE:
<221> NAME/KEY: MOD_RES
<222> LOCATION: 12
<223> OTHER INFORMATION: PEG6 inserted directly into sequence between
      Gly and Lys
<220> FEATURE:
<221> NAME/KEY: AMIDATION
<222> LOCATION: 13

<400> SEQUENCE: 97

Arg Trp Phe Glu Leu Pro Glu Pro Asp Trp Trp Gly Lys
1               5                   10
```

```
<210> SEQ ID NO 98
<211> LENGTH: 12
<212> TYPE: PRT
<213> ORGANISM: Artificial Sequence
<220> FEATURE:
<223> OTHER INFORMATION: Synthetic peptide RSVP1-G(PEG6)-Tricasso
<220> FEATURE:
<221> NAME/KEY: MOD_RES
<222> LOCATION: 12
<223> OTHER INFORMATION: PEG6 directly linked to C terminus

<400> SEQUENCE: 98

Arg Trp Phe Glu Leu Pro Glu Pro Asp Trp Trp Gly
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic peptide RSVP1-GK(PEG6)-Tricasso
<220> FEATURE:
<221> NAME/KEY: MOD_RES
<222> LOCATION: 13
<223> OTHER INFORMATION: PEG6 directly linked to C terminus

<400> SEQUENCE: 99

Arg Trp Phe Glu Leu Pro Glu Pro Asp Trp Trp Gly Lys
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Synthetic peptide KG-RSVP1-G(PEG6)-Tricasso
<220> FEATURE:
<221> NAME/KEY: MOD_RES
<222> LOCATION: 14
<223> OTHER INFORMATION: PEG6 directly linked to C terminus

<400> SEQUENCE: 100

Lys Gly Arg Trp Phe Glu Leu Pro Glu Pro Asp Trp Trp Gly
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Synthetic peptide RSVP3-G(PEG6)-Tricasso
<220> FEATURE:
<221> NAME/KEY: MOD_RES
<222> LOCATION: 12
<223> OTHER INFORMATION: PEG6 directly linked to C terminus

<400> SEQUENCE: 101

Ser Trp Phe Tyr Leu Pro Glu Pro Asp Trp Trp Gly
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Synthetic peptide KG-RSVP3-G(PEG6)-Tricasso
<220> FEATURE:
<221> NAME/KEY: MOD_RES
<222> LOCATION: 14
```

<223> OTHER INFORMATION: PEG6 directly linked to C terminus

<400> SEQUENCE: 102

Lys Gly Ser Trp Phe Tyr Leu Pro Glu Pro Asp Trp Trp Gly
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Synthetic peptide RSVP4-G(PEG6)-Tricasso
<220> FEATURE:
<221> NAME/KEY: MOD_RES
<222> LOCATION: 12
<223> OTHER INFORMATION: PEG6 linked directly to C terminus

<400> SEQUENCE: 103

Lys Tyr Phe Trp Leu Pro Glu Pro Asp Trp Trp Gly
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic peptide RSVP5-G(PEG6)-Tricasso
<220> FEATURE:
<221> NAME/KEY: MOD_RES
<222> LOCATION: 12
<223> OTHER INFORMATION: PEG6 directly linked to C terminus

<400> SEQUENCE: 104

Glu Trp Phe Tyr Leu Pro Glu Pro Arg Trp Trp Gly
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Synthetic peptide RSVP6-G(PEG6)-Tricasso
<220> FEATURE:
<221> NAME/KEY: MOD_RES
<222> LOCATION: 12
<223> OTHER INFORMATION: PEG6 directly linked to C terminus

<400> SEQUENCE: 105

Gln Trp Tyr Phe Leu Pro Glu Pro Asn Trp Trp Gly
1               5                   10

<210> SEQ ID NO 106
<211> LENGTH: 14
<212> TYPE: PRT
<213> ORGANISM: Artificial Sequence
<220> FEATURE:
<223> OTHER INFORMATION: Synthetic peptide KG-RSVP7-G(PEG6)-Tricasso
<220> FEATURE:
<221> NAME/KEY: MOD_RES
<222> LOCATION: 14
<223> OTHER INFORMATION: PEG6 directly linked to C terminus

<400> SEQUENCE: 106

Lys Gly Arg Trp Phe Glu Leu Pro Glu Pro Glu Trp Trp Gly
1               5                   10

<210> SEQ ID NO 107
<211> LENGTH: 15
<212> TYPE: PRT

```
<213> ORGANISM: Artificial Sequence
<220> FEATURE:
<223> OTHER INFORMATION: Synthetic peptide KKG-RSVP7-G(PEG6)-Tricasso
<220> FEATURE:
<221> NAME/KEY: MOD_RES
<222> LOCATION: 15
<223> OTHER INFORMATION: PEG6 directly linked to C terminus

<400> SEQUENCE: 107

Lys Lys Gly Arg Trp Phe Glu Leu Pro Glu Pro Glu Trp Trp Gly
1               5                   10                  15

<210> SEQ ID NO 108
<211> LENGTH: 14
<212> TYPE: PRT
<213> ORGANISM: Artificial Sequence
<220> FEATURE:
<223> OTHER INFORMATION: Synthetic peptide Ac-KG-RSVP7-G(PEG6)-Tricasso
<220> FEATURE:
<221> NAME/KEY: ACETYLATION
<222> LOCATION: 1
<220> FEATURE:
<221> NAME/KEY: MOD_RES
<222> LOCATION: 14
<223> OTHER INFORMATION: PEG6 directly linked to C terminus

<400> SEQUENCE: 108

Lys Gly Arg Trp Phe Glu Leu Pro Glu Pro Glu Trp Trp Gly
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Synthetic peptide Ac-RSVP7-G(PEG6)K
<220> FEATURE:
<221> NAME/KEY: ACETYLATION
<222> LOCATION: 1
<220> FEATURE:
<221> NAME/KEY: MOD_RES
<222> LOCATION: 12
<223> OTHER INFORMATION: PEG6 directly inserted in seqence between Gly
      and Lys
<220> FEATURE:
<221> NAME/KEY: AMIDATION
<222> LOCATION: 13

<400> SEQUENCE: 109

Arg Trp Phe Glu Leu Pro Glu Pro Glu Trp Trp Gly Lys
1               5                   10

<210> SEQ ID NO 110
<211> LENGTH: 15
<212> TYPE: PRT
<213> ORGANISM: Artificial Sequence
<220> FEATURE:
<223> OTHER INFORMATION: Synthetic peptide Ac-KG-RSVP7-G(PEG6)K
<220> FEATURE:
<221> NAME/KEY: ACETYLATION
<222> LOCATION: 1
<220> FEATURE:
<221> NAME/KEY: VARIANT
<222> LOCATION: 1
<223> OTHER INFORMATION: Xaa = Lys with DDE protecting group
<220> FEATURE:
<221> NAME/KEY: MOD_RES
<222> LOCATION: 14
<223> OTHER INFORMATION: PEG6 directly inserted in sequence between Gly
      and Lys
<220> FEATURE:
<221> NAME/KEY: AMIDATION
<222> LOCATION: 15
```

-continued

<400> SEQUENCE: 110

Xaa Gly Arg Trp Phe Glu Leu Pro Glu Pro Glu Trp Trp Gly Lys
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Synthetic peptide RRG-RSVP7-G(PEG6)K
<220> FEATURE:
<221> NAME/KEY: MOD_RES
<222> LOCATION: 15
<223> OTHER INFORMATION: PEG6 inserted directly into sequence between
      Gly and Lys
<220> FEATURE:
<221> NAME/KEY: AMIDATION
<222> LOCATION: 16

<400> SEQUENCE: 111

Arg Arg Gly Arg Trp Phe Glu Leu Pro Glu Pro Glu Trp Trp Gly Lys
1               5                   10                  15

<210> SEQ ID NO 112
<211> LENGTH: 19
<212> TYPE: PRT
<213> ORGANISM: Artificial Sequence
<220> FEATURE:
<223> OTHER INFORMATION: Synthetic peptide KKGAAAA-RSVP7-G(PEG6)-
      Tricasso
<220> FEATURE:
<221> NAME/KEY: MOD_RES
<222> LOCATION: 16
<223> OTHER INFORMATION: PEG6 linked directly to C terminus

<400> SEQUENCE: 112

Lys Lys Gly Ala Ala Ala Ala Arg Trp Phe Glu Leu Pro Glu Pro Glu
1               5                   10                  15

Trp Trp Gly

<210> SEQ ID NO 113
<211> LENGTH: 22
<212> TYPE: PRT
<213> ORGANISM: Artificial Sequence
<220> FEATURE:
<223> OTHER INFORMATION: Synthetic peptide Ac-RRG-RSVP11-G(PEG6)K
<220> FEATURE:
<221> NAME/KEY: ACETYLATION
<222> LOCATION: 1
<220> FEATURE:
<221> NAME/KEY: MOD_RES
<222> LOCATION: 21
<223> OTHER INFORMATION: PEG6 directly inserted in sequence between Gly
      and Lys
<220> FEATURE:
<221> NAME/KEY: AMIDATION
<222> LOCATION: 22

<400> SEQUENCE: 113

Arg Arg Gly Val Asp His Arg Trp Gln Arg Trp Phe Glu Leu Pro Asp
1               5                   10                  15

Pro Glu Trp Trp Gly Lys
            20

<210> SEQ ID NO 114
<211> LENGTH: 24
<212> TYPE: PRT
<213> ORGANISM: Artificial Sequence

```
<220> FEATURE:
<223> OTHER INFORMATION: Synthetic peptide Ac-RRRRG-RSVP11-G(PEG6)K
<220> FEATURE:
<221> NAME/KEY: ACETYLATION
<222> LOCATION: 1
<220> FEATURE:
<221> NAME/KEY: MOD_RES
<222> LOCATION: 23
<223> OTHER INFORMATION: PEG6 directly inserted in sequence between Gly
      and Lys
<220> FEATURE:
<221> NAME/KEY: AMIDATION
<222> LOCATION: 24

<400> SEQUENCE: 114

Arg Arg Arg Arg Gly Val Asp His Arg Trp Gln Arg Trp Phe Glu Leu
1               5                   10                  15

Pro Asp Pro Glu Trp Trp Gly Lys
            20

<210> SEQ ID NO 115
<211> LENGTH: 18
<212> TYPE: PRT
<213> ORGANISM: Artificial Sequence
<220> FEATURE:
<223> OTHER INFORMATION: Synthetic peptide CX10C-86-GK
<220> FEATURE:
<221> NAME/KEY: AMIDATION
<222> LOCATION: 18

<400> SEQUENCE: 115

Gly Ala Cys His Thr Trp Asp Leu Asn His Leu Asp Val Cys Ala Ala
1               5                   10                  15

Gly Lys

<210> SEQ ID NO 116
<211> LENGTH: 18
<212> TYPE: PRT
<213> ORGANISM: Artificial Sequence
<220> FEATURE:
<223> OTHER INFORMATION: Synthetic peptide Ac-CX10C-86-GK
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 116

Gly Ala Cys His Thr Trp Asp Leu Asn His Leu Asp Val Cys Ala Ala
1               5                   10                  15

Gly Lys

<210> SEQ ID NO 117
<211> LENGTH: 16
<212> TYPE: PRT
<213> ORGANISM: Artificial Sequence
<220> FEATURE:
<223> OTHER INFORMATION: Synthetic peptide CX10C-119
<220> FEATURE:
<221> NAME/KEY: AMIDATION
<222> LOCATION: 16

<400> SEQUENCE: 117

Gly Ala Cys Lys Ile His Asp Leu Phe His Trp His Asp Cys Ala Ala
1               5                   10                  15

<210> SEQ ID NO 118
```

```
<211> LENGTH: 16
<212> TYPE: PRT
<213> ORGANISM: Artificial Sequence
<220> FEATURE:
<223> OTHER INFORMATION: Synthetic peptide Ac-CX10C-119
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 118

Gly Ala Cys Lys Ile His Asp Leu Phe His Trp His Asp Cys Ala Ala
1               5                   10                  15

<210> SEQ ID NO 119
<211> LENGTH: 18
<212> TYPE: PRT
<213> ORGANISM: Artificial Sequence
<220> FEATURE:
<223> OTHER INFORMATION: Synthetic peptide CX10C-119-GG
<220> FEATURE:
<221> NAME/KEY: AMIDATION
<222> LOCATION: 18

<400> SEQUENCE: 119

Gly Ala Cys Lys Ile His Asp Leu Phe His Trp His Asp Cys Ala Ala
1               5                   10                  15

Gly Gly

<210> SEQ ID NO 120
<211> LENGTH: 18
<212> TYPE: PRT
<213> ORGANISM: Artificial Sequence
<220> FEATURE:
<223> OTHER INFORMATION: Synthetic peptide Ac-CX10C-119-GG
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 120

Gly Ala Cys Lys Ile His Asp Leu Phe His Trp His Asp Cys Ala Ala
1               5                   10                  15

Gly Gly

<210> SEQ ID NO 121
<211> LENGTH: 19
<212> TYPE: PRT
<213> ORGANISM: Artificial Sequence
<220> FEATURE:
<223> OTHER INFORMATION: Synthetic peptide Ac-CX10C-119-GG(PEG6)K
<220> FEATURE:
<221> NAME/KEY: ACETYLATION
<222> LOCATION: 1
<220> FEATURE:
<221> NAME/KEY: VARIANT
<222> LOCATION: 4
<223> OTHER INFORMATION: Xaa = Lys with DDE protecting group
<220> FEATURE:
<221> NAME/KEY: MOD_RES
<222> LOCATION: 18
<223> OTHER INFORMATION: PEG6 inserted directly into the sequence
      between Gly and Lys
<220> FEATURE:
<221> NAME/KEY: AMIDATION
<222> LOCATION: 19
```

```
<400> SEQUENCE: 121

Gly Ala Cys Xaa Ile His Asp Leu Phe His Trp His Asp Cys Ala Ala
1               5                   10                  15

Gly Gly Lys

<210> SEQ ID NO 122
<211> LENGTH: 19
<212> TYPE: PRT
<213> ORGANISM: Artificial Sequence
<220> FEATURE:
<223> OTHER INFORMATION: Synthetic peptide KKG-RSVP20-Tricasso
<220> FEATURE:
<221> NAME/KEY: MOD_RES
<222> LOCATION: 19
<223> OTHER INFORMATION: PEG6 directly linked to C terminus

<400> SEQUENCE: 122

Lys Lys Gly Gly Ala Cys Arg Asn Glu Pro His Trp Leu Leu Asp Trp
1               5                   10                  15

Cys Ala Ala

<210> SEQ ID NO 123
<211> LENGTH: 18
<212> TYPE: PRT
<213> ORGANISM: Artificial Sequence
<220> FEATURE:
<223> OTHER INFORMATION: Synthetic peptide Ac-KG-RSVP20
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 123

Lys Gly Gly Ala Cys Arg Asn Glu Pro His Trp Leu Leu Asp Trp Cys
1               5                   10                  15

Ala Ala

<210> SEQ ID NO 124
<211> LENGTH: 17
<212> TYPE: PRT
<213> ORGANISM: Artificial Sequence
<220> FEATURE:
<223> OTHER INFORMATION: Synthetic peptide Ac-K(PEG6)-RSVP20
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into sequence between
      Lys and Gly
<220> FEATURE:
<221> NAME/KEY: AMIDATION
<222> LOCATION: 17

<400> SEQUENCE: 124

Lys Gly Ala Cys Arg Asn Glu Pro His Trp Leu Leu Asp Trp Cys Ala
1               5                   10                  15

Ala

<210> SEQ ID NO 125
<211> LENGTH: 19
<212> TYPE: PRT
<213> ORGANISM: Artificial Sequence
<220> FEATURE:
```

```
<223> OTHER INFORMATION: Synthetic peptide KKG-RSVP21-Tricasso
<220> FEATURE:
<221> NAME/KEY: MOD_RES
<222> LOCATION: 19
<223> OTHER INFORMATION: PEG6 directly linked to C terminus

<400> SEQUENCE: 125

Lys Lys Gly Gly Ala Cys Thr Asn Arg Ala Glu Trp Leu Ile Asp Trp
1               5                   10                  15

Cys Ala Ala

<210> SEQ ID NO 126
<211> LENGTH: 17
<212> TYPE: PRT
<213> ORGANISM: Artificial Sequence
<220> FEATURE:
<223> OTHER INFORMATION: Synthetic peptide Ac-K(PEG6)-RSVP21
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into sequence between
      Lys and Gly
<220> FEATURE:
<221> NAME/KEY: AMIDATION
<222> LOCATION: 17

<400> SEQUENCE: 126

Lys Gly Ala Cys Thr Asn Arg Ala Glu Trp Leu Ile Asp Trp Cys Ala
1               5                   10                  15

Ala

<210> SEQ ID NO 127
<211> LENGTH: 17
<212> TYPE: PRT
<213> ORGANISM: Artificial Sequence
<220> FEATURE:
<223> OTHER INFORMATION: Synthetic peptide Ac-K(PEG6)-RSVP22
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 directly inserted into sequence between
      Lys and Gly
<220> FEATURE:
<221> NAME/KEY: AMIDATION
<222> LOCATION: 17

<400> SEQUENCE: 127

Lys Gly Ala Cys Lys Gln Arg Thr Glu Trp Tyr Phe Asp Trp Cys Ala
1               5                   10                  15

Ala

<210> SEQ ID NO 128
<211> LENGTH: 20
<212> TYPE: PRT
<213> ORGANISM: Artificial Sequence
<220> FEATURE:
<223> OTHER INFORMATION: Synthetic peptide Ac-K(PEG6)DDG-RSVP24
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 directly inserted into sequenced between
```

```
            Lys and Asp
<220> FEATURE:
<221> NAME/KEY: AMIDATION
<222> LOCATION: 20

<400> SEQUENCE: 128

Lys Asp Asp Gly Ser Met Cys Val Asn Arg Pro Glu Trp Leu Leu Asp
1               5                   10                  15

Trp Cys Gly Thr
            20

<210> SEQ ID NO 129
<211> LENGTH: 20
<212> TYPE: PRT
<213> ORGANISM: Artificial Sequence
<220> FEATURE:
<223> OTHER INFORMATION: Synthetic peptide Ac-RSVP24-GDD(PEG6)K
<220> FEATURE:
<221> NAME/KEY: ACETYLATION
<222> LOCATION: 1
<220> FEATURE:
<221> NAME/KEY: MOD_RES
<222> LOCATION: 19
<223> OTHER INFORMATION: PEG6 inserted directly into sequence between
      Asp and Lys
<220> FEATURE:
<221> NAME/KEY: AMIDATION
<222> LOCATION: 20

<400> SEQUENCE: 129

Ser Met Cys Val Asn Arg Pro Glu Trp Leu Leu Asp Trp Cys Gly Thr
1               5                   10                  15

Gly Asp Asp Lys
            20

<210> SEQ ID NO 130
<211> LENGTH: 20
<212> TYPE: PRT
<213> ORGANISM: Artificial Sequence
<220> FEATURE:
<223> OTHER INFORMATION: Synthetic peptide Ac-K(PEG6)RRG-RSVP24
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 directly inserted in sequence between Lys
      and Arg
<220> FEATURE:
<221> NAME/KEY: AMIDATION
<222> LOCATION: 20

<400> SEQUENCE: 130

Lys Arg Arg Gly Ser Met Cys Val Asn Arg Pro Glu Trp Leu Leu Asp
1               5                   10                  15

Trp Cys Gly Thr
            20

<210> SEQ ID NO 131
<211> LENGTH: 20
<212> TYPE: PRT
<213> ORGANISM: Artificial Sequence
<220> FEATURE:
<223> OTHER INFORMATION: Synthetic peptide Ac-K(PEG6)DDG-RSVP25
<220> FEATURE:
<221> NAME/KEY: ACETYLATION
<222> LOCATION: 1
<220> FEATURE:
<221> NAME/KEY: MOD_RES
```

```
<222> LOCATION: 1
<223> OTHER INFORMATION: PEG6 inserted directly into sequence between
      Lys and Asp
<220> FEATURE:
<221> NAME/KEY: AMIDATION
<222> LOCATION: 20

<400> SEQUENCE: 131

Lys Asp Asp Gly Glu Asp Cys Val Asn Arg Ser Tyr Trp Leu Leu Asp
1               5                   10                  15

Trp Cys Asn Ile
            20

<210> SEQ ID NO 132
<211> LENGTH: 20
<212> TYPE: PRT
<213> ORGANISM: Artificial Sequence
<220> FEATURE:
<223> OTHER INFORMATION: Synthetic peptide Ac-K(PEG6)DDG-RSVP26
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into sequence between
      Lys and Asp
<220> FEATURE:
<221> NAME/KEY: AMIDATION
<222> LOCATION: 20

<400> SEQUENCE: 132

Lys Asp Asp Gly His Ala Cys Val Asn Arg Pro Glu Trp Leu Leu Asp
1               5                   10                  15

Trp Cys Gly Arg
            20

<210> SEQ ID NO 133
<211> LENGTH: 21
<212> TYPE: PRT
<213> ORGANISM: Artificial Sequence
<220> FEATURE:
<223> OTHER INFORMATION: Synthetic peptide Ac-K(PEG6)G-RSVP26-GRR
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into sequence between
      Lys and Gly
<220> FEATURE:
<221> NAME/KEY: AMIDATION
<222> LOCATION: 21

<400> SEQUENCE: 133

Lys Gly His Ala Cys Val Asn Arg Pro Glu Trp Leu Leu Asp Trp Cys
1               5                   10                  15

Gly Arg Gly Arg Arg
            20

<210> SEQ ID NO 134
<211> LENGTH: 23
<212> TYPE: PRT
<213> ORGANISM: Artificial Sequence
<220> FEATURE:
<223> OTHER INFORMATION: Synthetic peptide Ac-K(PEG6)G-RSVP26-GRRRR
<220> FEATURE:
<221> NAME/KEY: ACETYLATION
<222> LOCATION: 1
```

```
<220> FEATURE:
<221> NAME/KEY: MOD_RES
<222> LOCATION: 1
<223> OTHER INFORMATION: PEG6 inserted directly into sequence between
      Lys and Gly
<220> FEATURE:
<221> NAME/KEY: AMIDATION
<222> LOCATION: 23

<400> SEQUENCE: 134

Lys Gly His Ala Cys Val Asn Arg Pro Glu Trp Leu Leu Asp Trp Cys
1               5                   10                  15

Gly Arg Gly Arg Arg Arg Arg
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic peptide Ac-K(PEG6)DDG-RSVP27
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into sequence between
      Lys and Asp
<220> FEATURE:
<221> NAME/KEY: AMIDATION
<222> LOCATION: 20

<400> SEQUENCE: 135

Lys Asp Asp Gly His Glu Cys Val Asn Arg Pro Glu Trp Leu Leu Asp
1               5                   10                  15

Trp Cys Glu His
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic peptide Ac-K(PEG6)DDG-RSVP28
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into sequence between
      Lys and Asp
<220> FEATURE:
<221> NAME/KEY: AMIDATION
<222> LOCATION: 20

<400> SEQUENCE: 136

Lys Asp Asp Gly His Ala Cys Val Asn Arg Pro Glu Trp Leu Leu Asp
1               5                   10                  15

Trp Cys Asp His
            20

<210> SEQ ID NO 137
<211> LENGTH: 20
<212> TYPE: PRT
<213> ORGANISM: Artificial Sequence
<220> FEATURE:
<223> OTHER INFORMATION: Synthetic peptide Ac-K(PEG6)DDG-RSVP29
<220> FEATURE:
```

```
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into sequence between
      Lys and Asp
<220> FEATURE:
<221> NAME/KEY: AMIDATION
<222> LOCATION: 20

<400> SEQUENCE: 137

Lys Asp Asp Gly Ser Ala Cys Val Asn Arg Pro Glu Trp Leu Leu Asp
1               5                   10                  15

Trp Cys Gly Thr
            20

<210> SEQ ID NO 138
<211> LENGTH: 20
<212> TYPE: PRT
<213> ORGANISM: Artificial Sequence
<220> FEATURE:
<223> OTHER INFORMATION: Synthetic peptide Ac-K(PEG6)DDG-RSVP30
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into sequence between
      Lys and Asp
<220> FEATURE:
<221> NAME/KEY: AMIDATION
<222> LOCATION: 20

<400> SEQUENCE: 138

Lys Asp Asp Gly Ser Ser Cys Val Asn Arg Pro Glu Trp Leu Leu Asp
1               5                   10                  15

Trp Cys Gly Thr
            20

<210> SEQ ID NO 139
<211> LENGTH: 20
<212> TYPE: PRT
<213> ORGANISM: Artificial Sequence
<220> FEATURE:
<223> OTHER INFORMATION: Synthetic peptide Ac-K(PEG6)DDG-RSVP31
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into seqeunce between
      Lys and Asp
<220> FEATURE:
<221> NAME/KEY: AMIDATION
<222> LOCATION: 20

<400> SEQUENCE: 139

Lys Asp Asp Gly Ala Glu Cys Val Asn Arg Pro Glu Trp Leu Leu Asp
1               5                   10                  15

Trp Cys Gly Thr
            20

<210> SEQ ID NO 140
<211> LENGTH: 20
<212> TYPE: PRT
<213> ORGANISM: Artificial Sequence
<220> FEATURE:
```

```
<223> OTHER INFORMATION: Synthetic peptide Ac-K(PEG6)DDG-RSVP32
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG6 inserted directly into sequence between
      Lys and Asp
<220> FEATURE:
<221> NAME/KEY: AMIDATION
<222> LOCATION: 20

<400> SEQUENCE: 140

Lys Asp Asp Gly Gly Glu Cys Val Asn Arg Pro Glu Trp Leu Leu Asp
1               5                   10                  15

Trp Cys Gly Thr
            20

<210> SEQ ID NO 141
<211> LENGTH: 16
<212> TYPE: PRT
<213> ORGANISM: Artificial Sequence
<220> FEATURE:
<223> OTHER INFORMATION: Synthetic peptide Ac-RSVP32
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 141

Gly Glu Cys Val Asn Arg Pro Glu Trp Leu Leu Asp Trp Cys Gly Thr
1               5                   10                  15

<210> SEQ ID NO 142
<211> LENGTH: 20
<212> TYPE: PRT
<213> ORGANISM: Artificial Sequence
<220> FEATURE:
<223> OTHER INFORMATION: Synthetic peptide Ac-K(PEG4)DDG-RSVP32
<220> FEATURE:
<221> NAME/KEY: ACETYLATION
<222> LOCATION: 1
<220> FEATURE:
<221> NAME/KEY: MOD_RES
<222> LOCATION: 1
<223> OTHER INFORMATION: PEG4 inserted directly into seqeunce between
      Lys and Asp
<220> FEATURE:
<221> NAME/KEY: AMIDATION
<222> LOCATION: 20

<400> SEQUENCE: 142

Lys Asp Asp Gly Gly Glu Cys Val Asn Arg Pro Glu Trp Leu Leu Asp
1               5                   10                  15

Trp Cys Gly Thr
            20

<210> SEQ ID NO 143
<211> LENGTH: 21
<212> TYPE: PRT
<213> ORGANISM: Artificial Sequence
<220> FEATURE:
<223> OTHER INFORMATION: Synthetic peptide Ac-K(PEG8)G-RSVP32-GDD
<220> FEATURE:
<221> NAME/KEY: ACETYLATION
<222> LOCATION: 1
<220> FEATURE:
<221> NAME/KEY: MOD_RES
```

```
<222> LOCATION: 1
<223> OTHER INFORMATION: PEG8 inserted directly into sequence between
      Lys and Gly
<220> FEATURE:
<221> NAME/KEY: AMIDATION
<222> LOCATION: 21

<400> SEQUENCE: 143

Lys Gly Gly Glu Cys Val Asn Arg Pro Glu Trp Leu Leu Asp Trp Cys
1               5                   10                  15

Gly Thr Gly Asp Asp
            20

<210> SEQ ID NO 144
<211> LENGTH: 20
<212> TYPE: PRT
<213> ORGANISM: Artificial Sequence
<220> FEATURE:
<223> OTHER INFORMATION: Synthetic peptide Ac-RSVP32-GDD(PEG6)K
<220> FEATURE:
<221> NAME/KEY: ACETYLATION
<222> LOCATION: 1
<220> FEATURE:
<221> NAME/KEY: MOD_RES
<222> LOCATION: 19
<223> OTHER INFORMATION: PEG6 inserted directly into sequence between
      Asp and Lys
<220> FEATURE:
<221> NAME/KEY: AMIDATION
<222> LOCATION: 20

<400> SEQUENCE: 144

Gly Glu Cys Val Asn Arg Pro Glu Trp Leu Leu Asp Trp Cys Gly Thr
1               5                   10                  15

Gly Asp Asp Lys
            20

<210> SEQ ID NO 145
<211> LENGTH: 20
<212> TYPE: PRT
<213> ORGANISM: Artificial Sequence
<220> FEATURE:
<223> OTHER INFORMATION: Synthetic peptide Ac-RSVP32-GDD(PEG4)K
<220> FEATURE:
<221> NAME/KEY: ACETYLATION
<222> LOCATION: 1
<220> FEATURE:
<221> NAME/KEY: MOD_RES
<222> LOCATION: 19
<223> OTHER INFORMATION: PEG4 inserted directly into sequence between
      Asp and Lys
<220> FEATURE:
<221> NAME/KEY: AMIDATION
<222> LOCATION: 20

<400> SEQUENCE: 145

Gly Glu Cys Val Asn Arg Pro Glu Trp Leu Leu Asp Trp Cys Gly Thr
1               5                   10                  15

Gly Asp Asp Lys
            20

<210> SEQ ID NO 146
<211> LENGTH: 21
<212> TYPE: PRT
<213> ORGANISM: Artificial Sequence
<220> FEATURE:
<223> OTHER INFORMATION: Synthetic peptide Ac-DDG-RSVP32-G(PEG8)K
<220> FEATURE:
<221> NAME/KEY: ACETYLATION
<222> LOCATION: 1
```

```
<220> FEATURE:
<221> NAME/KEY: MOD_RES
<222> LOCATION: 20
<223> OTHER INFORMATION: PEG8 inserted directly into sequence between
      Gly and Lys
<220> FEATURE:
<221> NAME/KEY: AMIDATION
<222> LOCATION: 21

<400> SEQUENCE: 146

Asp Asp Gly Gly Glu Cys Val Asn Arg Pro Glu Trp Leu Leu Asp Trp
1               5                   10                  15

Cys Gly Thr Gly Lys
            20

<210> SEQ ID NO 147
<211> LENGTH: 16
<212> TYPE: PRT
<213> ORGANISM: Artificial Sequence
<220> FEATURE:
<223> OTHER INFORMATION: Synthetic peptide RSVP32-6-HRG
<220> FEATURE:
<221> NAME/KEY: ACETYLATION
<222> LOCATION: 1
<220> FEATURE:
<221> NAME/KEY: VARIANT
<222> LOCATION: 6
<223> OTHER INFORMATION: Xaa = Homoarginine
<220> FEATURE:
<221> NAME/KEY: AMIDATION
<222> LOCATION: 16

<400> SEQUENCE: 147

Gly Glu Cys Val Asn Xaa Pro Glu Trp Leu Leu Asp Trp Cys Gly Thr
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Synthetic peptide RSVP32-6-ASU
<220> FEATURE:
<221> NAME/KEY: ACETYLATION
<222> LOCATION: 1
<220> FEATURE:
<221> NAME/KEY: VARIANT
<222> LOCATION: 6
<223> OTHER INFORMATION: Xaa = Aminosuberic acid
<220> FEATURE:
<221> NAME/KEY: AMIDATION
<222> LOCATION: 16

<400> SEQUENCE: 148

Gly Glu Cys Val Asn Xaa Pro Glu Trp Leu Leu Asp Trp Cys Gly Thr
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Synthetic peptide RSVP32-6-KCX
<220> FEATURE:
<221> NAME/KEY: ACETYLATION
<222> LOCATION: 1
<220> FEATURE:
<221> NAME/KEY: VARIANT
<222> LOCATION: 6
<223> OTHER INFORMATION: Xaa = Lysine Nz-carboxylic acid
<220> FEATURE:
<221> NAME/KEY: AMIDATION
```

<222> LOCATION: 16

<400> SEQUENCE: 149

Gly Glu Cys Val Asn Xaa Pro Glu Trp Leu Leu Asp Trp Cys Gly Thr
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Synthetic peptide RSVP32-6-HHK
<220> FEATURE:
<221> NAME/KEY: ACETYLATION
<222> LOCATION: 1
<220> FEATURE:
<221> NAME/KEY: VARIANT
<222> LOCATION: 6
<223> OTHER INFORMATION: Xaa = 2,8-Diaminooctanoic acid
<220> FEATURE:
<221> NAME/KEY: ACETYLATION
<222> LOCATION: 16

<400> SEQUENCE: 150

Gly Glu Cys Val Asn Xaa Pro Glu Trp Leu Leu Asp Trp Cys Gly Thr
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Synthetic peptide RSVP32-6-Gln
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 151

Gly Glu Cys Val Asn Gln Pro Glu Trp Leu Leu Asp Trp Cys Gly Thr
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Synthetic peptide RSVP32-6-Glu
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 152

Gly Glu Cys Val Asn Glu Pro Glu Trp Leu Leu Asp Trp Cys Gly Thr
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Synthetic peptide RSVP32-6-Lys
<220> FEATURE:
<221> NAME/KEY: ACETYLATION
<222> LOCATION: 1
<220> FEATURE:

<221> NAME/KEY: AMIDATION
<222> LOCATION: 16

<400> SEQUENCE: 153

Gly Glu Cys Val Asn Lys Pro Glu Trp Leu Leu Asp Trp Cys Gly Thr
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Synthetic peptide RSVP32-6-UN1
<220> FEATURE:
<221> NAME/KEY: ACETYLATION
<222> LOCATION: 1
<220> FEATURE:
<221> NAME/KEY: VARIANT
<222> LOCATION: 8
<223> OTHER INFORMATION: Xaa = 2-Aminoadipic acid, Homoglutamate
<220> FEATURE:
<221> NAME/KEY: AMIDATION
<222> LOCATION: 16

<400> SEQUENCE: 154

Gly Glu Cys Val Asn Arg Pro Xaa Trp Leu Leu Asp Trp Cys Gly Thr
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: Synthetic peptide RSVP32-6-CCS
<220> FEATURE:
<221> NAME/KEY: ACETYLATION
<222> LOCATION: 1
<220> FEATURE:
<221> NAME/KEY: VARIANT
<222> LOCATION: 8
<223> OTHER INFORMATION: Xaa = carboxymethylated cysteine
<220> FEATURE:
<221> NAME/KEY: AMIDATION
<222> LOCATION: 16

<400> SEQUENCE: 155

Gly Glu Cys Val Asn Arg Pro Xaa Trp Leu Leu Asp Trp Cys Gly Thr
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: Synthetic peptide RSVP32-8-ASU
<220> FEATURE:
<221> NAME/KEY: ACETYLATION
<222> LOCATION: 1
<220> FEATURE:
<221> NAME/KEY: VARIANT
<222> LOCATION: 8
<223> OTHER INFORMATION: Xaa = Aminosuberic acid
<220> FEATURE:
<221> NAME/KEY: AMIDATION
<222> LOCATION: 16

<400> SEQUENCE: 156

Gly Glu Cys Val Asn Arg Pro Xaa Trp Leu Leu Asp Trp Cys Gly Thr
1               5                   10                  15

<210> SEQ ID NO 157

```
<211> LENGTH: 16
<212> TYPE: PRT
<213> ORGANISM: Artificial Sequence
<220> FEATURE:
<223> OTHER INFORMATION: Synthetic peptide RSVP32-11-HLE
<220> FEATURE:
<221> NAME/KEY: ACETYLATION
<222> LOCATION: 1
<220> FEATURE:
<221> NAME/KEY: VARIANT
<222> LOCATION: 11
<223> OTHER INFORMATION: Xaa = Homoleucine
<220> FEATURE:
<221> NAME/KEY: AMIDATION
<222> LOCATION: 16

<400> SEQUENCE: 157

Gly Glu Cys Val Asn Arg Pro Glu Trp Leu Xaa Asp Trp Cys Gly Thr
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Synthetic peptide RSVP32-11-NLE
<220> FEATURE:
<221> NAME/KEY: ACETYLATION
<222> LOCATION: 1
<220> FEATURE:
<221> NAME/KEY: VARIANT
<222> LOCATION: 11
<223> OTHER INFORMATION: Xaa = Norlucine
<220> FEATURE:
<221> NAME/KEY: AMIDATION
<222> LOCATION: 16

<400> SEQUENCE: 158

Gly Glu Cys Val Asn Arg Pro Glu Trp Leu Xaa Asp Trp Cys Gly Thr
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Synthetic peptide RSVP32-multiple-Shortened
      disulfide
<220> FEATURE:
<221> NAME/KEY: ACETYLATION
<222> LOCATION: 1
<220> FEATURE:
<221> NAME/KEY: AMIDATION
<222> LOCATION: 15

<400> SEQUENCE: 159

Gly Glu Val Cys Arg Pro Glu Trp Leu Leu Asp Trp Cys Gly Thr
1               5                   10                  15

<210> SEQ ID NO 160
<211> LENGTH: 14
<212> TYPE: PRT
<213> ORGANISM: Artificial Sequence
<220> FEATURE:
<223> OTHER INFORMATION: Synthetic peptide Library N1-IZN21-C1
<220> FEATURE:
<221> NAME/KEY: VARIANT
<222> LOCATION: 1,2,4,5,10,13,14
<223> OTHER INFORMATION: Xaa = Gly or any of the other 19 natural amino
      acids in the D-configuration

<400> SEQUENCE: 160
```

Xaa Xaa Cys Xaa Xaa Thr Gly Tyr Phe Xaa Trp Cys Xaa Xaa
1               5                   10

<210> SEQ ID NO 161
<211> LENGTH: 14
<212> TYPE: PRT
<213> ORGANISM: Artificial Sequence
<220> FEATURE:
<223> OTHER INFORMATION: Synthetic peptide Library Library N1-IZN21-C2
<220> FEATURE:
<221> NAME/KEY: VARIANT
<222> LOCATION: 1,4,5,8,9,13,14
<223> OTHER INFORMATION: Xaa = Gly or any of the other 19 natural amino
      acids in the D-configuration

<400> SEQUENCE: 161

Xaa His Cys Xaa Xaa His Trp Xaa Xaa Asp Trp Cys Xaa Xaa
1               5                   10

<210> SEQ ID NO 162
<211> LENGTH: 14
<212> TYPE: PRT
<213> ORGANISM: Artificial Sequence
<220> FEATURE:
<223> OTHER INFORMATION: Synthetic peptide Library N1-IZN45-C1
<220> FEATURE:
<221> NAME/KEY: VARIANT
<222> LOCATION: 1,2,4,5,10,13,14
<223> OTHER INFORMATION: Xaa = Gly or any of the other 19 natural amino
      acids in the D-configuration

<400> SEQUENCE: 162

Xaa Xaa Cys Xaa Xaa Thr Gly Tyr Phe Xaa Trp Cys Xaa Xaa
1               5                   10

<210> SEQ ID NO 163
<211> LENGTH: 18
<212> TYPE: PRT
<213> ORGANISM: Artificial Sequence
<220> FEATURE:
<223> OTHER INFORMATION: Synthetic peptide Library N2-IZN45-C1
<220> FEATURE:
<221> NAME/KEY: VARIANT
<222> LOCATION: 3,7,14,17
<223> OTHER INFORMATION: Xaa = Gly or any of the other 19 natural amino
      acids in the D-configuration
<220> FEATURE:
<221> NAME/KEY: VARIANT
<222> LOCATION: 9
<223> OTHER INFORMATION: Xaa = Asp or Glu

<400> SEQUENCE: 163

Ala Leu Xaa Lys Lys Asp Xaa Glu Xaa Leu Lys Lys Phe Xaa Glu Trp
1               5                   10                  15

Xaa Gly

<210> SEQ ID NO 164
<211> LENGTH: 18
<212> TYPE: PRT
<213> ORGANISM: Artificial Sequence
<220> FEATURE:
<223> OTHER INFORMATION: Synthetic peptide Library N2-IZN45-C2
<220> FEATURE:
<221> NAME/KEY: VARIANT
<222> LOCATION: 3,6,7,9,13,14,17
<223> OTHER INFORMATION: Xaa = Gly or any of the other 19 natural amino
      acids in the D-configuration

<400> SEQUENCE: 164

Ala His Xaa Lys Ile Xaa Xaa Glu Xaa Trp Lys Lys Xaa Xaa Glu His

```
1               5                   10                  15

Xaa Gly

<210> SEQ ID NO 165
<211> LENGTH: 18
<212> TYPE: PRT
<213> ORGANISM: Artificial Sequence
<220> FEATURE:
<223> OTHER INFORMATION: Synthetic peptide Library N2-IZN45-C3
<220> FEATURE:
<221> NAME/KEY: VARIANT
<222> LOCATION: 6,7,9,10,14,16,17
<223> OTHER INFORMATION: Xaa = Gly or any of the other 19 natural amino
      acids in the D-configuration

<400> SEQUENCE: 165

Ala Trp Asp Lys Lys Xaa Xaa Glu Xaa Xaa Lys Lys Phe Xaa Glu Xaa
1               5                   10                  15

Xaa Gly

<210> SEQ ID NO 166
<211> LENGTH: 13
<212> TYPE: PRT
<213> ORGANISM: Artificial Sequence
<220> FEATURE:
<223> OTHER INFORMATION: Synthetic peptide Library N1-IZN21-C3
<220> FEATURE:
<221> NAME/KEY: VARIANT
<222> LOCATION: 1,2,9,12,13
<223> OTHER INFORMATION: Xaa = Gly or any of the other 19 natural amino
      acids in the D-configuration

<400> SEQUENCE: 166

Xaa Xaa Cys Asp Trp Ser His Tyr Xaa Gly Cys Xaa Xaa
1               5                   10

<210> SEQ ID NO 167
<211> LENGTH: 14
<212> TYPE: PRT
<213> ORGANISM: Artificial Sequence
<220> FEATURE:
<223> OTHER INFORMATION: Synthetic peptide

<400> SEQUENCE: 167

Ser His Cys Tyr Ser Thr Gly Tyr Phe His Trp Cys Asp Gln
1               5                   10

<210> SEQ ID NO 168
<211> LENGTH: 14
<212> TYPE: PRT
<213> ORGANISM: Artificial Sequence
<220> FEATURE:
<223> OTHER INFORMATION: Synthetic peptide

<400> SEQUENCE: 168

Gln His Cys Ile Asn Thr Gly Tyr Phe Asp Trp Cys Glu Lys
1               5                   10

<210> SEQ ID NO 169
<211> LENGTH: 14
<212> TYPE: PRT
<213> ORGANISM: Artificial Sequence
<220> FEATURE:
<223> OTHER INFORMATION: Synthetic peptide

<400> SEQUENCE: 169

His Gln Cys Gln Val His Gly Tyr Phe Asn Trp Cys Pro Thr
```

<210> SEQ ID NO 170
<211> LENGTH: 14
<212> TYPE: PRT
<213> ORGANISM: Artificial Sequence
<220> FEATURE:
<223> OTHER INFORMATION: Synthetic peptide

<400> SEQUENCE: 170

Asp His Cys Ile Thr Thr Gly Tyr Phe Lys Trp Cys Asp Asp
1               5                   10

<210> SEQ ID NO 171
<211> LENGTH: 14
<212> TYPE: PRT
<213> ORGANISM: Artificial Sequence
<220> FEATURE:
<223> OTHER INFORMATION: Synthetic peptide

<400> SEQUENCE: 171

Thr His Cys Val Ser Thr Gly Tyr Phe Gln Trp Cys Pro Tyr
1               5                   10

<210> SEQ ID NO 172
<211> LENGTH: 14
<212> TYPE: PRT
<213> ORGANISM: Artificial Sequence
<220> FEATURE:
<223> OTHER INFORMATION: Synthetic peptide

<400> SEQUENCE: 172

Asp Asn Cys Ile Thr Thr Gly Tyr Phe His Trp Cys Asp Ser
1               5                   10

<210> SEQ ID NO 173
<211> LENGTH: 14
<212> TYPE: PRT
<213> ORGANISM: Artificial Sequence
<220> FEATURE:
<223> OTHER INFORMATION: Synthetic peptide

<400> SEQUENCE: 173

Ile Asp Cys Tyr Ser Thr Gly Tyr Phe Arg Trp Cys Asp Lys
1               5                   10

<210> SEQ ID NO 174
<211> LENGTH: 14
<212> TYPE: PRT
<213> ORGANISM: Artificial Sequence
<220> FEATURE:
<223> OTHER INFORMATION: Synthetic peptide

<400> SEQUENCE: 174

Glu Leu Cys Tyr Thr Thr Gly Tyr Phe Thr Trp Cys Pro Gln
1               5                   10

<210> SEQ ID NO 175
<211> LENGTH: 14
<212> TYPE: PRT
<213> ORGANISM: Artificial Sequence
<220> FEATURE:
<223> OTHER INFORMATION: Synthetic peptide

<400> SEQUENCE: 175

His Ala Cys Ser Val His Gly Phe Phe Asn Trp Cys Pro Glu
1               5                   10

```
<210> SEQ ID NO 176
<211> LENGTH: 14
<212> TYPE: PRT
<213> ORGANISM: Artificial Sequence
<220> FEATURE:
<223> OTHER INFORMATION: Synthetic peptide

<400> SEQUENCE: 176

Val Glu Cys Tyr Arg Thr Gly Tyr Phe Gln Trp Cys Lys His
1               5                   10

<210> SEQ ID NO 177
<211> LENGTH: 14
<212> TYPE: PRT
<213> ORGANISM: Artificial Sequence
<220> FEATURE:
<223> OTHER INFORMATION: Synthetic peptide

<400> SEQUENCE: 177

His Ala Cys Ser Val His Gly Phe Phe Asn Trp Cys Pro Glu
1               5                   10

<210> SEQ ID NO 178
<211> LENGTH: 14
<212> TYPE: PRT
<213> ORGANISM: Artificial Sequence
<220> FEATURE:
<223> OTHER INFORMATION: Synthetic peptide

<400> SEQUENCE: 178

Ala His Cys Asp Tyr His Trp Met Leu Asp Trp Cys Asn Leu
1               5                   10

<210> SEQ ID NO 179
<211> LENGTH: 14
<212> TYPE: PRT
<213> ORGANISM: Artificial Sequence
<220> FEATURE:
<223> OTHER INFORMATION: Synthetic peptide

<400> SEQUENCE: 179

Ser His Cys Asp Thr His Trp Met Leu Asp Trp Cys Pro Gln
1               5                   10

<210> SEQ ID NO 180
<211> LENGTH: 14
<212> TYPE: PRT
<213> ORGANISM: Artificial Sequence
<220> FEATURE:
<223> OTHER INFORMATION: Synthetic peptide

<400> SEQUENCE: 180

Gln His Cys His Glu His Trp Trp Phe Asp Trp Cys Pro Glu
1               5                   10

<210> SEQ ID NO 181
<211> LENGTH: 14
<212> TYPE: PRT
<213> ORGANISM: Artificial Sequence
<220> FEATURE:
<223> OTHER INFORMATION: Synthetic peptide

<400> SEQUENCE: 181

Glu His Cys Asp Leu His Trp Asn Phe Asp Trp Cys Thr Val
1               5                   10
```

```
<210> SEQ ID NO 182
<211> LENGTH: 14
<212> TYPE: PRT
<213> ORGANISM: Artificial Sequence
<220> FEATURE:
<223> OTHER INFORMATION: Synthetic peptide

<400> SEQUENCE: 182

Ser His Cys Glu Met His Trp Glu Met Asp Trp Cys Gln Lys
1               5                   10

<210> SEQ ID NO 183
<211> LENGTH: 14
<212> TYPE: PRT
<213> ORGANISM: Artificial Sequence
<220> FEATURE:
<223> OTHER INFORMATION: Synthetic peptide

<400> SEQUENCE: 183

Tyr Leu Cys Asp Pro Thr Trp Leu Leu Asp Trp Cys His Thr
1               5                   10

<210> SEQ ID NO 184
<211> LENGTH: 14
<212> TYPE: PRT
<213> ORGANISM: Artificial Sequence
<220> FEATURE:
<223> OTHER INFORMATION: Synthetic peptide

<400> SEQUENCE: 184

Val His Cys Pro Phe His Trp Glu Met Asn Trp Cys Gln Ser
1               5                   10

<210> SEQ ID NO 185
<211> LENGTH: 14
<212> TYPE: PRT
<213> ORGANISM: Artificial Sequence
<220> FEATURE:
<223> OTHER INFORMATION: Synthetic peptide

<400> SEQUENCE: 185

Gly His Cys Pro Tyr His Trp Ser Leu Asp Trp Cys Val Asp
1               5                   10

<210> SEQ ID NO 186
<211> LENGTH: 14
<212> TYPE: PRT
<213> ORGANISM: Artificial Sequence
<220> FEATURE:
<223> OTHER INFORMATION: Synthetic peptide

<400> SEQUENCE: 186

Asp His Cys Pro Met His Trp Asn Phe Ser Trp Cys Glu Asp
1               5                   10

<210> SEQ ID NO 187
<211> LENGTH: 14
<212> TYPE: PRT
<213> ORGANISM: Artificial Sequence
<220> FEATURE:
<223> OTHER INFORMATION: Synthetic peptide

<400> SEQUENCE: 187

Ser His Cys Pro Ala His Trp Leu Met Asp Trp Cys Val Gln
1               5                   10
```

<210> SEQ ID NO 188
<211> LENGTH: 14
<212> TYPE: PRT
<213> ORGANISM: Artificial Sequence
<220> FEATURE:
<223> OTHER INFORMATION: Synthetic peptide

<400> SEQUENCE: 188

Asn His Cys Asp Leu His Trp Glu Met Asp Trp Cys Lys Ser
1               5                   10

<210> SEQ ID NO 189
<211> LENGTH: 14
<212> TYPE: PRT
<213> ORGANISM: Artificial Sequence
<220> FEATURE:
<223> OTHER INFORMATION: Synthetic peptide

<400> SEQUENCE: 189

Gln Trp Cys Asp Trp Ser His Tyr Trp Gly Lys Cys Gly Thr
1               5                   10

<210> SEQ ID NO 190
<211> LENGTH: 14
<212> TYPE: PRT
<213> ORGANISM: Artificial Sequence
<220> FEATURE:
<223> OTHER INFORMATION: Synthetic peptide

<400> SEQUENCE: 190

Thr Phe Cys Asp Trp Ser His Tyr Trp Gly Gln Cys Lys Ile
1               5                   10

<210> SEQ ID NO 191
<211> LENGTH: 14
<212> TYPE: PRT
<213> ORGANISM: Artificial Sequence
<220> FEATURE:
<223> OTHER INFORMATION: Synthetic peptide

<400> SEQUENCE: 191

Phe Tyr Cys Asp Trp Ser His Tyr Gly Gly Gln Cys Lys Ile
1               5                   10

<210> SEQ ID NO 192
<211> LENGTH: 14
<212> TYPE: PRT
<213> ORGANISM: Artificial Sequence
<220> FEATURE:
<223> OTHER INFORMATION: Synthetic peptide

<400> SEQUENCE: 192

Ile Asp Cys Tyr Ser Thr Gly Tyr Phe Arg Trp Cys Asp Lys
1               5                   10

<210> SEQ ID NO 193
<211> LENGTH: 14
<212> TYPE: PRT
<213> ORGANISM: Artificial Sequence
<220> FEATURE:
<223> OTHER INFORMATION: Synthetic peptide

<400> SEQUENCE: 193

Gln His Cys Ile Asn Thr Gly Tyr Phe Asp Trp Cys Glu Lys
1               5                   10

<210> SEQ ID NO 194

```
<211> LENGTH: 14
<212> TYPE: PRT
<213> ORGANISM: Artificial Sequence
<220> FEATURE:
<223> OTHER INFORMATION: Synthetic peptide

<400> SEQUENCE: 194

Ser His Cys Tyr Ser Thr Gly Tyr Phe His Trp Cys Asp Gln
1               5                   10

<210> SEQ ID NO 195
<211> LENGTH: 18
<212> TYPE: PRT
<213> ORGANISM: Artificial Sequence
<220> FEATURE:
<223> OTHER INFORMATION: Synthetic peptide

<400> SEQUENCE: 195

Ala Met Asp Lys Lys Phe Tyr Glu Asp Leu Lys Lys Phe Asn Glu Trp
1               5                   10                  15

Trp Gly

<210> SEQ ID NO 196
<211> LENGTH: 18
<212> TYPE: PRT
<213> ORGANISM: Artificial Sequence
<220> FEATURE:
<223> OTHER INFORMATION: Synthetic peptide

<400> SEQUENCE: 196

Ala Leu His Lys Lys Asp Tyr Glu Glu Leu Lys Lys Phe Trp Glu Trp
1               5                   10                  15

Ala Gly

<210> SEQ ID NO 197
<211> LENGTH: 18
<212> TYPE: PRT
<213> ORGANISM: Artificial Sequence
<220> FEATURE:
<223> OTHER INFORMATION: Synthetic peptide

<400> SEQUENCE: 197

Ala Leu His Lys Lys Asp Tyr Glu Glu Leu Lys Lys Phe Tyr Glu Trp
1               5                   10                  15

Ala Gly

<210> SEQ ID NO 198
<211> LENGTH: 18
<212> TYPE: PRT
<213> ORGANISM: Artificial Sequence
<220> FEATURE:
<223> OTHER INFORMATION: Synthetic peptide

<400> SEQUENCE: 198

Ala Leu His Lys Lys Asp Tyr Glu Glu Leu Lys Lys Phe His Glu Trp
1               5                   10                  15

Trp Gly

<210> SEQ ID NO 199
<211> LENGTH: 18
<212> TYPE: PRT
<213> ORGANISM: Artificial Sequence
<220> FEATURE:
<223> OTHER INFORMATION: Synthetic peptide
```

```
<400> SEQUENCE: 199

Ala Leu Asp Lys Lys Asp Met Glu Asp Leu Lys Lys Tyr Trp Glu Trp
1               5                   10                  15

Leu Gly

<210> SEQ ID NO 200
<211> LENGTH: 18
<212> TYPE: PRT
<213> ORGANISM: Artificial Sequence
<220> FEATURE:
<223> OTHER INFORMATION: Synthetic peptide

<400> SEQUENCE: 200

Ala Leu Asp Lys Lys Asp Tyr Glu Asp Leu Lys Lys Phe Trp Glu Trp
1               5                   10                  15

Val Gly

<210> SEQ ID NO 201
<211> LENGTH: 18
<212> TYPE: PRT
<213> ORGANISM: Artificial Sequence
<220> FEATURE:
<223> OTHER INFORMATION: Synthetic peptide

<400> SEQUENCE: 201

Ala Leu Glu Lys Lys Asp Trp Glu Asp Leu Lys Lys Phe Gln Glu Trp
1               5                   10                  15

Trp Gly

<210> SEQ ID NO 202
<211> LENGTH: 18
<212> TYPE: PRT
<213> ORGANISM: Artificial Sequence
<220> FEATURE:
<223> OTHER INFORMATION: Synthetic peptide

<400> SEQUENCE: 202

Ala Leu Asn Lys Lys Asp Leu Glu Asp Leu Lys Lys Phe Tyr Glu Trp
1               5                   10                  15

Ala Gly

<210> SEQ ID NO 203
<211> LENGTH: 18
<212> TYPE: PRT
<213> ORGANISM: Artificial Sequence
<220> FEATURE:
<223> OTHER INFORMATION: Synthetic peptide

<400> SEQUENCE: 203

Ala Leu Asn Lys Lys Asp His Glu Asp Leu Lys Lys Phe Tyr Glu Trp
1               5                   10                  15

Met Gly

<210> SEQ ID NO 204
<211> LENGTH: 18
<212> TYPE: PRT
<213> ORGANISM: Artificial Sequence
<220> FEATURE:
<223> OTHER INFORMATION: Synthetic peptide

<400> SEQUENCE: 204

Ala Leu Asn Lys Lys Asp Tyr Glu Asp Leu Lys Lys Tyr Tyr Glu Trp
1               5                   10                  15
```

Phe Gly

```
<210> SEQ ID NO 205
<211> LENGTH: 18
<212> TYPE: PRT
<213> ORGANISM: Artificial Sequence
<220> FEATURE:
<223> OTHER INFORMATION: Synthetic peptide

<400> SEQUENCE: 205

Ala Leu Thr Lys Lys Asp Ala Glu Asp Leu Lys Lys Phe Tyr Glu Trp
1               5                   10                  15

Phe Gly

<210> SEQ ID NO 206
<211> LENGTH: 18
<212> TYPE: PRT
<213> ORGANISM: Artificial Sequence
<220> FEATURE:
<223> OTHER INFORMATION: Synthetic peptide

<400> SEQUENCE: 206

Ala His Glu Lys Thr Leu Leu Glu Trp Glu Lys Lys Trp Leu Glu His
1               5                   10                  15

Phe Gly

<210> SEQ ID NO 207
<211> LENGTH: 18
<212> TYPE: PRT
<213> ORGANISM: Artificial Sequence
<220> FEATURE:
<223> OTHER INFORMATION: Synthetic peptide

<400> SEQUENCE: 207

Ala Gln Lys Ile Glu Glu Glu Phe Trp Lys Lys Leu Trp Glu His
1               5                   10                  15

Ser Gly

<210> SEQ ID NO 208
<211> LENGTH: 18
<212> TYPE: PRT
<213> ORGANISM: Artificial Sequence
<220> FEATURE:
<223> OTHER INFORMATION: Synthetic peptide

<400> SEQUENCE: 208

Ala His His Lys Ile Glu Asp Glu Phe Trp Lys Lys Val Ser Glu His
1               5                   10                  15

Trp Gly

<210> SEQ ID NO 209
<211> LENGTH: 18
<212> TYPE: PRT
<213> ORGANISM: Artificial Sequence
<220> FEATURE:
<223> OTHER INFORMATION: Synthetic peptide

<400> SEQUENCE: 209

Ala His His Lys Ile Gln Asp Glu Tyr Trp Lys Lys Val Leu Glu His
1               5                   10                  15

Val Gly
```

```
<210> SEQ ID NO 210
<211> LENGTH: 18
<212> TYPE: PRT
<213> ORGANISM: Artificial Sequence
<220> FEATURE:
<223> OTHER INFORMATION: Synthetic peptide

<400> SEQUENCE: 210

Ala Trp Asp Lys Lys Glu Thr Glu Phe Trp Lys Lys Phe Glu Glu Phe
1               5                   10                  15

Tyr Gly

<210> SEQ ID NO 211
<211> LENGTH: 18
<212> TYPE: PRT
<213> ORGANISM: Artificial Sequence
<220> FEATURE:
<223> OTHER INFORMATION: Synthetic peptide

<400> SEQUENCE: 211

Ala Trp Asp Lys Lys Gln Val Glu Asp Tyr Lys Lys Phe Tyr Glu Ile
1               5                   10                  15

Phe Gly

<210> SEQ ID NO 212
<211> LENGTH: 18
<212> TYPE: PRT
<213> ORGANISM: Artificial Sequence
<220> FEATURE:
<223> OTHER INFORMATION: Synthetic peptide

<400> SEQUENCE: 212

Ala Trp Asp Lys Lys Asp Trp Glu Asp Trp Lys Lys Phe Glu Glu Thr
1               5                   10                  15

Phe Gly

<210> SEQ ID NO 213
<211> LENGTH: 18
<212> TYPE: PRT
<213> ORGANISM: Artificial Sequence
<220> FEATURE:
<223> OTHER INFORMATION: Synthetic peptide

<400> SEQUENCE: 213

Ala Trp Asp Lys Lys Glu Leu Glu Phe Trp Lys Asn Tyr Glu Glu Trp
1               5                   10                  15

Tyr Gly

<210> SEQ ID NO 214
<211> LENGTH: 20
<212> TYPE: PRT
<213> ORGANISM: Artificial Sequence
<220> FEATURE:
<223> OTHER INFORMATION: Synthetic peptide Ac-K(P4)-EEG-RSVP32
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 1
<223> OTHER INFORMATION: PEG4 inserted directly into the sequence
      between Lys and Glu
<220> FEATURE:
<221> NAME/KEY: MOD_RES
<222> LOCATION: 20
<223> OTHER INFORMATION: AMIDATION
```

<400> SEQUENCE: 214

Lys Glu Glu Gly Gly Glu Cys Val Asn Arg Pro Glu Trp Leu Leu Asp
1               5                   10                  15

Trp Cys Gly Thr
            20

<210> SEQ ID NO 215
<211> LENGTH: 18
<212> TYPE: PRT
<213> ORGANISM: Artificial Sequence
<220> FEATURE:
<223> OTHER INFORMATION: Synthetic Peptide Ac-K(P6)-E-RSVP32
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 1
<223> OTHER INFORMATION: PEG6 inserted directly into sequence between
      Lys and Glu
<220> FEATURE:
<221> NAME/KEY: MOD_RES
<222> LOCATION: 18
<223> OTHER INFORMATION: AMIDATION

<400> SEQUENCE: 215

Lys Glu Gly Glu Cys Val Asn Arg Pro Glu Trp Leu Leu Asp Trp Cys
1               5                   10                  15

Gly Thr

<210> SEQ ID NO 216
<211> LENGTH: 16
<212> TYPE: PRT
<213> ORGANISM: Artificial Sequence
<220> FEATURE:
<223> OTHER INFORMATION: Synthetic peptide PEG8-RSVP32
<220> FEATURE:
<221> NAME/KEY: MOD_RES
<222> LOCATION: 1
<223> OTHER INFORMATION: PEG8 attached at N-Terminal
<220> FEATURE:
<221> NAME/KEY: MOD_RES
<222> LOCATION: 16
<223> OTHER INFORMATION: AMIDATION

<400> SEQUENCE: 216

Gly Glu Cys Val Asn Arg Pro Glu Trp Leu Leu Asp Trp Cys Gly Thr
1               5                   10                  15

<210> SEQ ID NO 217
<211> LENGTH: 14
<212> TYPE: PRT
<213> ORGANISM: Artificial Sequence
<220> FEATURE:
<223> OTHER INFORMATION: Synthetic peptide

<400> SEQUENCE: 217

His His Cys Glu Gly Gly Leu Leu His Tyr Trp Cys Asp Ile
1               5                   10

<210> SEQ ID NO 218
<211> LENGTH: 14
<212> TYPE: PRT
<213> ORGANISM: Artificial Sequence
<220> FEATURE:
<223> OTHER INFORMATION: Synthetic peptide

<400> SEQUENCE: 218

Arg Val Cys Trp Asp Glu Glu Val Thr Trp Arg Cys Phe His
1               5                   10

<210> SEQ ID NO 219
<211> LENGTH: 14
<212> TYPE: PRT
<213> ORGANISM: Artificial Sequence
<220> FEATURE:
<223> OTHER INFORMATION: Synthetic peptide

<400> SEQUENCE: 219

Asn His Cys Pro Lys Asp His Trp Gly Trp Leu Cys Trp Asp
1               5                   10

<210> SEQ ID NO 220
<211> LENGTH: 44
<212> TYPE: PRT
<213> ORGANISM: Respiratory Syncytial Virus A2 strain
<220> FEATURE:
<223> OTHER INFORMATION: N-trimer groove of F protein

<400> SEQUENCE: 220

Val Asn Lys Ile Lys Ser Ala Leu Leu Ser Thr Asn Lys Ala Val Val
1               5                   10                  15

Ser Leu Ser Asn Gly Val Ser Val Leu Thr Ser Lys Val Leu Asp Leu
            20                  25                  30

Lys Asn Tyr Ile Asp Lys Cys Leu Leu Pro Ile Val
            35                  40

<210> SEQ ID NO 221
<211> LENGTH: 44
<212> TYPE: PRT
<213> ORGANISM: Respiratory Syncytial Virus B strain
<220> FEATURE:
<223> OTHER INFORMATION: N-trimer groove of F protein

<400> SEQUENCE: 221

Val Asn Lys Ile Lys Asn Ala Leu Leu Ser Thr Asn Lys Ala Val Val
1               5                   10                  15

Ser Leu Ser Asn Gly Val Ser Val Leu Thr Ser Lys Val Leu Asp Leu
            20                  25                  30

Lys Asn Tyr Ile Asn Asn Gln Leu Leu Pro Ile Val
            35                  40

<210> SEQ ID NO 222
<211> LENGTH: 18
<212> TYPE: PRT
<213> ORGANISM: Artificial Sequence
<220> FEATURE:
<223> OTHER INFORMATION: Synthetic peptide

<400> SEQUENCE: 222

Ala Leu Asp Lys Lys Asp Thr Glu Asp Leu Lys Lys Phe Trp Glu Trp
1               5                   10                  15

Val Gly

<210> SEQ ID NO 223
<211> LENGTH: 18
<212> TYPE: PRT
<213> ORGANISM: Artificial Sequence
<220> FEATURE:
<223> OTHER INFORMATION: Synthetic peptide -continued

```
<400> SEQUENCE: 223

Ala His Phe Lys Lys Asp Thr Glu Asp Trp Lys Lys Leu Val Glu Ile
1               5                   10                  15

Phe Gly

<210> SEQ ID NO 224
<211> LENGTH: 44
<212> TYPE: PRT
<213> ORGANISM: Respiratory Syncytial Virus A strain 8510A

<400> SEQUENCE: 224

Val Asn Lys Ile Lys Ser Ala Leu Phe Phe Thr Asn Lys Ala Val Val
1               5                   10                  15

Ser Leu Ser Asn Gly Val Ser Val Leu Thr Ser Lys Val Leu Asp Leu
            20                  25                  30

Lys Asn Tyr Ile Asp Lys Cys Leu Leu Pro Ile Val
        35                  40

<210> SEQ ID NO 225
<211> LENGTH: 44
<212> TYPE: PRT
<213> ORGANISM: Respiratory Syncytial Virus B strain 8508B

<400> SEQUENCE: 225

Val Asn Lys Ile Lys Asn Ala Leu Leu Ser Thr Asn Lys Ala Val Val
1               5                   10                  15

Ser Leu Ser Asn Gly Val Ser Val Leu Thr Ser Lys Val Leu Asp Leu
            20                  25                  30

Lys Asn Tyr Arg Asn Asn Gln Leu Leu Pro Ile Val
        35                  40

<210> SEQ ID NO 226
<211> LENGTH: 44
<212> TYPE: PRT
<213> ORGANISM: Respiratory Syncytial Virus B strain 30730B

<400> SEQUENCE: 226

Val Asn Lys Ile Lys Asn Ala Leu Leu Ser Thr Asn Lys Ala Val Val
1               5                   10                  15

Ser Leu Ser Asn Gly Val Ser Val Leu Thr Asn Lys Val Leu Asp Leu
            20                  25                  30

Lys Asn Tyr Ile Asn Asn Gln Leu Leu Pro Ile Val
        35                  40

<210> SEQ ID NO 227
<211> LENGTH: 44
<212> TYPE: PRT
<213> ORGANISM: Respiratory Syncytial Virus B strain 31775B

<400> SEQUENCE: 227

Val Asn Lys Ile Lys Asn Ala Leu Gln Ser Thr Asn Lys Ala Val Val
1               5                   10                  15

Ser Leu Ser Asn Gly Val Ser Val Leu Thr Ser Lys Val Leu Asp Leu
            20                  25                  30

Lys Asn Tyr Ile Asn Asn Gln Leu Leu Pro Ile Val
        35                  40

<210> SEQ ID NO 228
<211> LENGTH: 44
<212> TYPE: PRT
```

```
<213> ORGANISM: Respiratory Syncytial Virus B strain 32075B
<220> FEATURE:
<221> NAME/KEY: VARIANT
<222> LOCATION: (1)...(44)
<223> OTHER INFORMATION: Xaa = unknown

<400> SEQUENCE: 228

Val Asn Lys Ile Lys Asn Ala Leu Leu Ser Thr Asn Lys Xaa Val Val
1               5                   10                  15

Ser Leu Ser Asn Gly Val Ser Val Leu Thr Ser Lys Val Leu Asp Leu
            20                  25                  30

Lys Asn Tyr Ile Asn Asn Gln Leu Leu Pro Ile Val
            35                  40

<210> SEQ ID NO 229
<211> LENGTH: 44
<212> TYPE: PRT
<213> ORGANISM: Respiratory Syncytial Virus B strain 35098B

<400> SEQUENCE: 229

Val Asn Lys Ile Lys Asn Ala Leu Leu Ser Thr Asn Ile Val Val Val
1               5                   10                  15

Ser Leu Ser Asn Gly Val Ser Val Leu Thr Ser Lys Val Leu Asp Leu
            20                  25                  30

Lys Asn Tyr Ile Asn Asn Gln Leu Leu Pro Ile Val
            35                  40
```